United States Patent
Sievernich et al.

(10) Patent No.: US 9,999,223 B2
(45) Date of Patent: Jun. 19, 2018

(54) HERBICIDAL COMPOSITION COMPRISING GLYPHOSATE, GLUFOSINATE OR THEIR SALTS

(71) Applicant: BASF SE, Ludwigshafen (DE)

(72) Inventors: Bernd Sievernich, Hassloch (DE); William Karl Moberg, Hassloch (DE); Anja Simon, Weinheim (DE); Helmut Walter, Obrigheim (DE); Richard R. Evans, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/336,983

(22) Filed: Oct. 28, 2016

(65) Prior Publication Data

US 2017/0042159 A1 Feb. 16, 2017

Related U.S. Application Data

(63) Continuation of application No. 12/992,096, filed as application No. PCT/EP2009/056105 on May 20, 2009, now Pat. No. 9,629,366.

(60) Provisional application No. 61/055,040, filed on May 21, 2008, provisional application No. 61/056,622, filed on May 28, 2008, provisional application No. 61/118,895, filed on Dec. 1, 2008.

(51) Int. Cl.
| | |
|---|---|
| *A01N 43/80* | (2006.01) |
| *A01N 43/54* | (2006.01) |
| *A01N 43/50* | (2006.01) |
| *A01N 43/40* | (2006.01) |
| *A01N 37/40* | (2006.01) |
| *A01N 33/18* | (2006.01) |
| *A01N 43/68* | (2006.01) |
| *A01N 43/84* | (2006.01) |
| *A01N 43/10* | (2006.01) |
| *A01N 57/20* | (2006.01) |

(52) U.S. Cl.
CPC .............. *A01N 43/80* (2013.01); *A01N 33/18* (2013.01); *A01N 37/40* (2013.01); *A01N 43/10* (2013.01); *A01N 43/40* (2013.01); *A01N 43/50* (2013.01); *A01N 43/54* (2013.01); *A01N 43/68* (2013.01); *A01N 43/84* (2013.01); *A01N 57/20* (2013.01)

(58) Field of Classification Search
None
See application file for complete search history.

(56) References Cited

U.S. PATENT DOCUMENTS

| | | | |
|---|---|---|---|
| 6,277,787 B1 * | 8/2001 | Malefyt | A01N 57/20 504/127 |
| 6,413,909 B1 | 7/2002 | Walker | |
| 6,677,276 B1 | 1/2004 | Hacker et al. | |
| 2005/0256004 A1 * | 11/2005 | Takahashi | A01N 43/80 504/271 |
| 2008/0108072 A1 * | 5/2008 | Chicoine | C12N 15/8275 435/6.13 |
| 2011/0009265 A1 | 1/2011 | Sievernich et al. | |
| 2011/0009266 A1 | 1/2011 | Sievernich et al. | |
| 2011/0015067 A1 | 1/2011 | Sievernich et al. | |
| 2011/0015068 A1 | 1/2011 | Sievernich et al. | |
| 2011/0015069 A1 | 1/2011 | Sievernich et al. | |
| 2011/0021356 A1 | 1/2011 | Sievernich et al. | |
| 2011/0028325 A1 | 2/2011 | Sievernich et al. | |

FOREIGN PATENT DOCUMENTS

| | | |
|---|---|---|
| WO | WO 00/08938 | 2/2000 |
| WO | WO 03/028468 | 4/2003 |
| WO | WO 2006/097322 | 9/2006 |

OTHER PUBLICATIONS

King, S.R. et al., "Annual Broadleaf Control with KIH-485 in Glyphosate-Resistant Furrow-Irrigated Corn" Weed Technology, vol. 22, No. 3, 2008, 420-424, XP002585038.

(Continued)

*Primary Examiner* — Robert A Wax
*Assistant Examiner* — Thor Nielsen
(74) *Attorney, Agent, or Firm* — Brinks Gilson & Lione

(57) ABSTRACT

The present invention relates to a herbicidal composition which comprises:
a) at least one herbicide A selected from glyphosate, glufosinate and their salts, and
b) a herbicide B which is 3-[5-(difluoromethoxy)-1-methyl-3-(trifluoromethyl)pyrazol-4-ylmethylsulfonyl]-4,5-dihydro-5,5-dimethyl-1,2-oxazole [common name: pyroxasulfone].

The present invention relates in particular to a herbicidal composition comprising:
a) at least one herbicide A selected from glyphosate, glufosinate and their salts,
b) a herbicide B which is 3-[5-(difluoromethoxy)-1-methyl-3-(trifluoromethyl)pyrazol-4-ylmethylsulfonyl]-4,5-dihydro-5,5-dimethyl-1,2-oxazole [common name: pyroxasulfone], and
c) at least one further herbicide C, which is selected from the herbicide groups C.1 to C.8:
  C.1 herbicides of the group of acetolactate synthase inhibitors (ALS inhibitors),
  C.2 herbicides of the group of protoporphyrinogen oxidase inhibitors (PPO inhibitors),
  C.3 herbicides of the group of auxines,
  C.4 herbicides of the group of 4-hydroxyphenyl-pyruvate-dioxygenase inhibitors (HPPD inhibitors),
  C.5 herbicides of the group of phytoene desaturase inhibitors (PDS inhibitors),
  C.6 herbicides of the group of photosystem II inhibitors (PSII inhibitors),
  C.7 herbicides of the group of microtubulin inhibitors, and
  C.8 herbicides of the group of inhibitors of the synthesis of very long chain fatty acids (VLCFA inhibitors).

4 Claims, No Drawings

(56) References Cited

OTHER PUBLICATIONS

King, R.L. et al., "Control of acetolactate synthas-resistant shattercane (*Sorghum bicolor*) in field corn with KIH-485", Weed Technology, vol. 21, No. 3, 2007, 587-582, XP002585036.
Koger, C.H. et al., "Evaluation of new herbicide chemistry: Does KIH-485 have a fit in the southern cotton producing region", National Cotton Council, Beltwide Cotton Conferences, 2008, XP002585037.
Tanetani, Y. et al.: "Action mechanism of a novel herbicide, pyroxasulfone", Pesticide Biochemistry and Physiology, Academic Press, US LNKDDOI10.1016/J.PESTBP.2009.6.003, vol. 95, No. 1, 2009, pp. 47-55, XP026305571.
Y. Yamaji et al., Application timing and field performance of KIH-485, Conference Abstract I-1-ii-12B of 11. IUPAC International Congress of Pesticide Chemistry, 2006 Kobe, Japan.

* cited by examiner

US 9,999,223 B2

HERBICIDAL COMPOSITION COMPRISING GLYPHOSATE, GLUFOSINATE OR THEIR SALTS

CROSS REFERENCE TO RELATED APPLICATIONS

This application is a continuation of U.S. application Ser. No. 12/992,096, filed Nov. 11, 2010, the entire contents of which is hereby incorporated herein by reference. U.S. application Ser. No. 12/992,096 is a National Stage application of PCT/EP2009/056105, filed May 20, 2009, which claims the benefit of U.S. Provisional Application No. 61/055,040, filed May 21, 2008; U.S. Provisional Application No. 61/056,622, filed May 28, 2008; and U.S. Provisional Application No. 61/118,895, filed Dec. 1, 2008, the entire contents of each are hereby incorporated herein by reference.

The present invention relates to a herbicidal composition which comprises at least one herbicide A selected from glyphosate, glufosinate and their salts. The composition is particularly useful for preplant burndown.

Burndown, i.e. the complete removal of weeds from the soil by application of herbicides prior to planting or emergence of a crop, is an important tool of modern weed management. Weeds present at planting will generally grow much quicker than crop plants and thus compete very early in the growing season thereby damaging the crop plants and reducing crop yield. Thus, it is desirable to plant the crop in a weed-free seed bed or to assure that essentially no weeds are present when the crop emerges.

Glyphosate and its salts are non-selective systemic herbicides having a good post-emergence activity against numerous grass weeds. So far, glyphosate is one of the most commonly used burndown herbicides. Likewise, glufosinate and its salts are non-selective systemic herbicides having a good post-emergence activity against numerous grass weeds and thus can be used in burndown programs. However, solo application of glyphosate or glufosinate often yields unsatisfactory weed control, and several applications and/or high dosage rates are often required. Moreover, the effectiveness of glyphosate and glufosinate against difficult-to-control broadleaf species (hereinafter broadleaves) and rhizomatous grasses is poor. Therefore, it is frequently recommended to apply glyphosate or glufosinate in combination with at least one second herbicide, such as 2,4-D, dicamba, triazines such as atrazine or metribuzin, chloroacetanilides such as metolachlor or dimethenamid (including dimethenamid-P), linuron and/or pendimethalin. However, the effectiveness of such combinations is often not satisfactory and high application rates are still required to achieve an acceptable control of grass weeds and broadleaves. Moreover, the reliability of such combinations depends strongly on the weathering conditions and certain difficult to control weed species may escape. In addition, the herbicidal activity of these compositions persists only for a short time, which allows effective burndown only within a small timeframe prior to planting a crop. Moreover, the persistence of the herbicidal activity strongly depends upon the weathering conditions.

U.S. Pat. No. 6,413,909 suggests a composition comprising ametryn, atrazin and paraquat for burndown treatment. Paraquat, however is rather toxic to mammals and thus its use is restricted by legal regulations.

US 2005/0256004 discloses a herbicidal composition comprising an isoxazoline derivatives and at least one further herbicide. Neither the combination of glyphosate and pyroxasulfone nor the use of such compositions in a burndown program have been described therein.

Thus, it is an object of the present invention to provide a herbicidal composition, which allows efficient and reliable control of grass and broadleaf weeds in a burndown program. Moreover, the persistence of the herbicidal activity of the composition should be sufficiently long in order to achieve control of the weeds over a sufficient long time period thus allowing a more flexible application. The composition should also have a low toxicity to humans or other mammals. The compositions should also show an accelerated action on harmful plants, i.e. they should effect damaging of the harmful plants more quickly in comparison with application of the individual herbicides.

These and further objects are achieved by the compositions described hereinafter.

Therefore the present invention relates to a herbicidal composition comprising:
a) at least one herbicide A selected from glyphosate, glufosinate and their salts, and
b) a herbicide B which is 3-[5-(difluoromethoxy)-1-methyl-3-(trifluoromethyl)pyrazol-4-ylmethylsulfonyl]-4,5-dihydro-5,5-dimethyl-1,2-oxazole [common name: pyroxasulfone].

It has been proven particular advantageous to combine the herbicides A and B with at least one further herbicide C, which is selected from
C.1 herbicides of the group of acetolactate synthase inhibitors (ALS inhibitors),
C.2 herbicides of the group of protoporphyrinogen oxidase inhibitors (PPO inhibitors),
C.3 herbicides of the group of auxins,
C.4 herbicides of the group of 4-hydroxyphenylpyruvate dioxygenase inhibitors (HPPD inhibitors),
C.5 herbicides of the group of phytoene desaturase inhibitors (PDS inhibitors),
C.6 herbicides of the group of photosystem II inhibitors (PSII inhibitors),
C.7 herbicides of the group of microtubulin inhibitors, and
C.8 herbicides of the group of inhibitors of the synthesis of very long chain fatty acids (VLCFA inhibitors).

Therefore, the present invention relates in particular to a herbicidal composition comprising:
a) at least one herbicide A selected from glyphosate, glufosinate and their salts,
b) a herbicide B which is 3-[5-(difluoromethoxy)-1-methyl-3-(trifluoromethyl)pyrazol-4-ylmethylsulfonyl]-4,5-dihydro-5,5-dimethyl-1,2-oxazole [common name: pyroxasulfone], and
c) at least one further herbicide C, which is selected from the herbicide groups C.1 to C.8 as defined herein.

The invention furthermore relates to the use of a composition as defined herein for controlling undesirable vegetation. When using the compositions of the invention for this purpose the at least one herbicide A and the herbicide B and optionally C can be applied simultaneously or in succession, where undesirable vegetation may occur.

The invention furthermore relates to the use of a composition as defined herein for controlling undesirable vegetation for burndown, i.e. for controlling undesirable vegetation in a locus, e.g. a field, where crops will be planted, before planting or emergence of the crop.

The invention furthermore relates to the use of a composition as defined herein for controlling undesirable vegetation in crops which, by genetic engineering or by breeding, are resistant to one or more herbicides and/or pathogens such as plant-pathogenous fungi, and/or to attack by insects;

preferably resistant to glyphosate or glufosinate, and optionally resistant to the one or more optional herbicides C.

The invention furthermore relates to a method for controlling undesirable vegetation, which comprises applying an herbicidal composition according to the present invention to the undesirable vegetation. Application can be done before, during and/or after, preferably during and/or after, the emergence of the undesirable vegetation. The at least one herbicide A, the herbicide B and the optional at least one herbicide C can be applied simultaneously or in succession.

The invention in particular relates to a method for controlling undesirable vegetation in crops, which comprises applying a) at least one herbicide A selected from glyphosate, glufosinate and their salts, and optionally
b) a herbicide B which is 3-[5-(difluoromethoxy)-1-methyl-3-(trifluoromethyl)pyrazol-4-ylmethylsulfonyl]-4,5-dihydro-5,5-dimethyl-1,2-oxazole,
c) one or more herbicides C, selected from the herbicides of the groups C.1 to C.8 as defined herein, to a locus of planted crops where undesirable vegetation occurs or might occur or to a locus where crops will be planted before planting or emergence of the crop.

In the methods of the present invention it is immaterial whether the at least one herbicide A and the herbicide B and the one or more optional herbicides C are formulated jointly or separately and applied jointly or separately, and, in the case of separate application, in which order the application takes place. It is only necessary, that the at least one herbicide A and the herbicide B and the one or more optional herbicides C are applied in a time frame, which allows simultaneous action of the active ingredients on the undesirable plants.

The invention also relates to an herbicide formulation, which comprises a herbicidally active composition as defined herein and at least one carrier material, including liquid and/or solid carrier materials.

The compositions of the present invention have several advantages over solo application of either glyphosate/glufosinate or pyroxasulfone. The composition of the present invention show enhanced herbicide action in comparison with the herbicide action of solo action glyphosate or pyroxasulfone against undesirable vegetation, in particular against difficult to control species such as *Alopecurus myosuroides, Avena fatua, Bromus* spec., *Echinocloa* spec. *Ipomea* spec., *Lolium* spec., *Phalaris* spec., *Setaria* spec., *Digitaria* spec., *Brachiaria* spec., *Amaranthus* spec., *Chenopodium* spec., *Abutilon theophrasti, Galium aparine, Veronica* spec., or *Solanum* spec. Moreover, the compositions of the invention show a persistent herbicidal activity, even under difficult weathering conditions, which allows a more flexible application in burndown applications and minimizes the risk of weeds escaping. The compositions are generally non-toxic or of low toxicity against mammals. Apart form that, the compositions of the present invention show superior crop compatibility with certain conventional crop plants and with herbicide tolerant crop plants, i.e. their use in these crops leads to a reduced damage of the crop plants and/or does not result in increased damage of the crop plants. Thus, the compositions of the invention can also be applied after the emergence of the crop plants. The compositions of the present invention may also show an accelerated action on harmful plants, i.e. they may effect damage of the harmful plants more quickly in comparison with solo application of the individual herbicides.

Although, these advantages may be achieved by combining glyphosate and/or glufosinate with pyroxasulfone, it is particularly beneficial to further combine these herbicides A and B with at least one further herbicide C of the herbicide groups C.1 to C.8. These compositions show enhanced herbicide action in comparison with the herbicide action of combinations of herbicides A+B against undesirable vegetation, in particular against difficult to control species, and/or show superior crop compatibility with certain conventional crop plants and with herbicide tolerant crop plants, i.e. their use in these crops leads to a reduced damage of the crop plants and/or does not result in increased damage of the crop plants. Apart from that, these compositions may also show an accelerated action on harmful plants, i.e. they may effect damage of the harmful plants more quickly in comparison with solo application of the individual herbicides.

As used herein, the terms "controlling" and "combating" are synonyms.

As used herein, the terms "undesirable vegetation", "undesirable species", "undesirable plants", "harmful plants", "undesirable weeds", or "harmful weeds" are synonyms.

Glyphosate [common name of N-(phosphonomethyl)glycine] is a well known non-selective systemic herbicide, which has been described e.g. in U.S. Pat. No. 3,799,758 and U.S. Pat. No. 4,4505,531. Glyphosate is commercially available e.g. from Monsanto under the tradenames Roundup™ and Touchdown™. Glyphosate is also available and marketed in the form of its agriculturally acceptable salts such as glyphosate-diammonium [69254-40-6], glyphosate-isopropylammonium [38641-94-0], glyphosate-monoammonium [40465-66-5], glyphosate-potassium [70901-20-1], glyphosate-sesquisodium [70393-85-0], glyphosate-trimesium [81591-81-3]. Preferably, glyphosate is used in the form of its monoammonium, diammonium, isopropylammonium or trimesium salt.

Glufosinate [common name of DL-4-[hydroxyl(methyl)phosphinoyl]-DL-homoalaninate] and its salts such as glufosinate ammonium and its herbicidal activity have been described e.g. by F. Schwerdtle et al. Z. Pflanzenkr. Pflanzenschutz, 1981, Sonderheft IX, pp. 431-440. Glufosinate and its salts are commercially available, e.g. from Bayer CropScience under the tradenames Basta™ and Liberty™.

3-[5-(Difluoromethoxy)-1-methyl-3-(trifluoromethyl)pyrazol-4-ylmethylsulfonyl]-4,5-dihydro-5,5-dimethyl-1,2-oxazole [common name: pyroxasulfone] has been described as a preemergent herbicide in EP-A 1364946.

In the compositions of the invention the weight ratio of herbicide A to herbicide B is preferably from 2000:1 to 1:10, in particular from 500:1 to 1:6 and more preferably from 100:1 to 1:2.

In the compositions of the invention, wherein at least one herbicide C is present, the weight ratio of herbicide A to herbicide B+C is preferably from 1500:1 to 1:100, in particular from 1000:1 to 1:50 and more preferably from 500:1 to 1:20.

If the compounds of herbicide compounds mentioned as herbicides A, herbicides C and safeners D (see below) have functional groups, which can be ionized, they can also be used in the form of their agriculturally acceptable salts. In general, the salts of those cations are suitable whose cations have no adverse effect on the action of the active compounds ("agricultural acceptable").

In general, the salts of those cations are suitable whose cations have no adverse effect on the action of the active compounds ("agricultural acceptable"). Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, pentylammonium, hexylammonium, heptylammonium, 2-hydroxyethylammonium, 2-(2-hydroxyethoxy)eth-1-ylammonium, (diglycolamine salts), di(2-hydroxyeth-1-yl)ammonium (diolamine salts), tris((2-hydroxyeth-1-yl) ammonium (trolamine salts), tris(3-propanol)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

In the compositions according to the invention, the compounds C or D that carry a carboxyl group can also be employed in the form of agriculturally acceptable derivatives, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester. Preferred derivatives are the esters.

According to a first preferred embodiment of the invention (embodiment 1), the herbicidal compositions of the invention additionally comprise at least one further herbicide C selected from the group of acetolactate synthase inhibitors, also termed as ALS inhibitors (also termed AHAS inhibitors or inhibitors of acetohydroxy acid synthase). ALS inhibitors are compounds, which have a mode of action comprising the inhibition of a step of the branched chain amino acids biosynthesis in plants and which belong to the group B of the HRAC classification system (see HRAC, Classification of Herbicides According to Mode of Action, http://www.plantprotection.org/hrac/MOA.html).

According to the present invention the ALS inhibitor is preferably selected from the group consisting of:
C.1.1 imidazolinone herbicides;
C.1.2 sulfonylurea herbicides;
C.1.3 triazolopyrimidine herbicides;
C.1.4 pyrimidinylbenzoate herbicides; and
C.1.5 sulfonylaminocarbonyltriazolinone herbicides.

Imidazolinone herbicides (C.1.1) include e.g. imazapic, imazamethabenz-methyl, imazamox, imazapyr, imazaquin, and imazethapyr and the salts thereof.

Sulfonylurea herbicides (C.1.2) include e.g. amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron prosulfuron, pyrazosulfuron, rimsulfuron, sulfometuron, sulfosulfuron, thifensulfuron, triasulfuron, tribenuron, trifloxysulfuron, triflusulforon and tritosulfuron and the salts, and esters thereof.

Triazolopyrimidine herbicides (C.1.3) include e.g. cloransulam-methyl, diclosulam, florasulam, flumetsulam, metosulam, penoxsulam and pyroxsulam.

Pyrimidinylbenzoate herbicides (C.1.4) include e.g. bispyribac, pyribenzoxim, pyriftalid, pyrithiobac and pyriminobac and the salts and esters thereof such as bispyribac-sodium, pyrithiobac-sodium and pyriminobac-methyl.

Sulfonylaminocarbonyltriazolinone herbicides (C.1.5) include e.g. flucarbazone, propxycarbazone and thiencarbazone, and the salts and esters thereof such as flucarbazone-sodium, propxycarbazone-sodium and thiencarbazone-methyl.

In the compositions of this preferred embodiment 1 the relative weight ratio of pyroxasulfone to herbicide C.1 is preferably in the range from 1:500 to 500:1, in particular in the range from 1:250 to 250:1 and more preferably from 100:1 to 1:100. The relative weight ratio of herbicide A to herbicide B+herbicide C.1 is preferably in the range from 1500:1 to 1:20, in particular from 1000:1 to 1:10 and more preferably from 500:1 to 1:5.

According to a particular preferred embodiment of the invention, the component c) comprises at least one imidazolinone herbicide (embodiment 1.1). Imidazolinone herbicides (group C.1.1) are known e.g. from Shaner, D. L. O'Conner, S. L The Imidazolinone Herbicides, CRC Press Inc., Boca Raton, Fla. 1991 and also from The Compendium of Pesticide Common Names http://www.alanwood.net/pesticides/.

Imidazolinone herbicides include imazamethabenz, imazamox, imazapic, imazapyr, imazaquin and imazethapyr, their salts, in particular their sodium salts, potassium salts, ammonium salts or substituted ammonium salts as defined above, in particular mono-, di and tri-$C_1$-$C_8$-alkylammonium salts such as isopropylammonium salts and their esters, in particular their $C_1$-$C_8$-alkyl esters, such as methylesters, ethylesters, iso propyl esters. Suitable examples of such salts include imazamox-ammonium, imazapic-ammonium, imazapyr-isopropylammonium, imazaquin-ammonium, imazaquin-sodium and imazethapyr-ammonium. Suitable examples of such esters include imazamethabenz-methyl and imazaquin-methyl.

Preferred imidazolinone herbicides include imazamox, imazapic, imazapyr, imazaquin, imazethapyr, their salts and their esters, as well as mixtures thereof, in particular imazamox, imazapic, imazapyr and imazethapyr, their salts and their esters, as well as mixtures thereof, in particular mixtures of imazamox with imazapyr and/or imazethapyr and mixtures of imazapic with imazapyr and/or imazethapyr.

The imidazolinones may be present in the form of their racemate or in the form of the pure R- or S-enantiomers (including salts and esters as defined above). Very suitable Imidazolinones are the R-isomers, e.g. R-imazamethabenz-methyl, R-imazamox, R-imazapic, R-imazapyr, R-imazaquin, R-imazethapyr, in particular R-imazamox. These compounds are known e.g. from U.S. Pat. No. 5,973,154 B (American Cyanamid Company) and U.S. Pat. No. 6,339,158 B1 (American Cyanamid Company).

In particular preferred compositions of the embodiment 1.1, the herbicide C comprises or in particular is imazamox or a salt thereof such as imazamox-ammonium.

In other particular preferred compositions of the embodiment 1.1, the herbicide C comprises or in particular is imazapic or a salt thereof such as imazapic-ammonium.

In further particular preferred compositions of the embodiment 1.1, the herbicide C comprises or in particular is imazapyr or a salt thereof such as imazapyr-ammonium or imazapyr-isopropylammonium.

In further particular preferred compositions of the embodiment 1.1, the herbicide C comprises or in particular is imazethapyr or a salt thereof such as imazethapyr-ammonium.

In further particular preferred compositions of the embodiment 1.1, the herbicide C comprises or in particular is imazaquin or a salt or ester thereof such as imazaquin-ammonium, imazaquin-sodium or imazaquin-methyl.

In further particular preferred compositions of the embodiment 1.1, the herbicide C comprises or in particular is a mixture of imazamox and imazethapyr or salts thereof.

In further particular preferred compositions of the embodiment 1.1, the herbicide C comprises or in particular is a mixture of imazapic and imazethapyr or salts thereof.

In further particular preferred compositions of this embodiment 1.1, the herbicide C comprises or in particular is a mixture of imazamox and imazapyr or salts thereof.

In a further particular preferred compositions of the embodiment 1.1, the herbicide C comprises or in particular is a mixture of imazapic and imazapyr or salts thereof.

In the embodiment 1.1 the relative weight ratio of pyroxasulfone and imidazolinone herbicide is preferably from 1:500 to 500:1, in particular in the range from 1:250 to 250:1 and more preferably from 100:1 to 1:100. The relative weight ratio of herbicide A to herbicide B+herbicide C.1.1 is preferably in the range from 1500:1 to 1:20, in particular from 1000:1 to 1:10 and more preferably from 500:1 to 1:5.

According to a second preferred embodiment of the invention (embodiment 2), the herbicidal compositions of the invention additionally comprise at least one further herbicide C.2 which is an inhibitor of protoporphyrinogen-IX-oxidase (PPO inhibitor). PPO inhibitors are compounds, which have a mode of action comprising the inhibition of a step of the chlorophyll biosynthesis in plants and which belong to the group E of the HRAC classification system (see HRAC, Classification of Herbicides According to Mode of Action, http://www.plantprotection.org/hrac/MOA.html).

According to the present invention the PPO inhibitor of the group C.2 is preferably selected from the group consisting of:
C.2.1 phenyluracil herbicides;
C.2.2 dicarboximide herbicides;
C.2.3 triazolone and oxadiazolone herbicides;
C.2.4 nitrophenylether herbicides;
C.2.5 pyrazole herbicides;
C.2.6 triazindione herbicides; and
C.2.7 dicarboxamide herbicides.

Phenyluracil herbicides, which are also termed as pyrimidinedione herbicides (group C.2.1) include benzfendizone and compounds of the formula C.2.1 and the salts thereof,

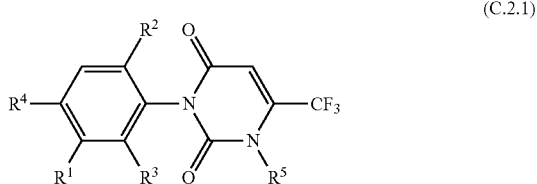

(C.2.1)

wherein
$R^1$ is selected from the group consisting of the radicals propargyloxy, allyloxy, isopropyloxy, $C(=O)NHSO_2NR^{1a}R^{1b}$, $C(=O)N-NR^{1a}R^{1b}$, $O-CR^{1a}R^{1c}-C(=O)-OR^{1e}$, $C(=O)O-CR^{1a}R^{1c}-C(=O)-OR^{1e}$, $C(=O)O-R^{1b}$, $C(=O)O-CHR^{1c}-C(=O)NHSO_2NR^{1a}R^{1b}$, $NHSO_2NR^{1a}R^{1b}$, $SO_2NHC(=O)NR^{1a}R^{1b}$, $CH_2-CH(Cl)CO_2-R^{1d}$ and the radical of the formula $OC(CH_3)_2-C(=O)-OR^{1e}$; where
$R^{1a}$ is hydrogen or $C_1-C_4$-alkyl;
$R^{1b}$ is $C_1-C_4$-alkyl;
$R^{1c}$ is hydrogen or $C_1-C_4$-alkyl;
$R^{1d}$ is hydrogen or $C_1-C_4$-alkyl or a agriculturally acceptable cation; and
$R^{1e}$ is $C_1-C_4$-alkyl, propargyl or allyl;
$R^2$ is hydrogen, fluorine or chlorine;
$R^3$ is hydrogen or together with $R^1$ forms a moiety $-O-C(R^{3a})=N-$ or $-N=C(R^{3b})-NH-$
where $R^{3a}$ and $R^{3b}$ are selected, independently of each other, from hydrogen, $C_1-C_6$-alkyl, $C_1-C_6$-haloalkyl, $C_3-C_6$-alkenyl, $C_3-C_6$-haloalkenyl, $C_3-C_6$-alkylnyl, $C_3-C_6$-haloalkylnyl, $C_1-C_6$-alkoxy, $C_3-C_6$-cycloalkyl and $C_1-C_2$-alkyl substituted by a $C_3-C_6$-cycloalkyl radical; with $R^{3a}$ and $R^{3b}$ preferably being selected, independently of each other, from $C_1-C_4$-alkyl, $C_1-C_2$-haloalkyl, and $C_1-C_2$-alkyl substituted by a $C_3-C_6$-cycloalkyl radical with $R^{3a}$ and $R^{3b}$ more preferably being selected, independently of each other, from methyl, ethyl, n-propyl, isoprobly, n-butyl, 2-methylpropyl, trifluoromethyl and cyclopropylmethyl;
$R^4$ is halogen or cyano, in particular chlorine or fluorine; and
$R^5$ is selected from hydrogen amino, methyl or propargyl and wherein $R^5$ is preferably methyl.

The organic moieties mentioned in the above definitions of the variables are—like the term halogen—collective terms for individual listings of the individual group members. The prefix $C_n-C_m$ indicates in each case the possible number of carbon atoms in the group.

The term halogen denotes in each case fluorine, bromine, chlorine or iodine, in particular fluorine, chlorine or bromine.

The term "alkyl" as used herein denotes in each case a straight-chain or branched alkyl group having usually from 1 to 6 carbon atoms, preferably from 1 to 4 carbon atoms, more preferably from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term "haloalkyl" as used herein denotes in each case a straight-chain or branched alkyl group having usually from 1 to 6 carbon atoms, preferably from 1 to 4 carbon atoms, wherein the hydrogen atoms of this group are partially or totally replaced with halogen atoms. Preferred haloalkyl moieties are selected from $C_1-C_4$-haloalkyl, more preferably from $C_1-C_2$-haloalkyl, in particular from $C_1-C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl and the like.

The term "alkoxy" as used herein denotes in each case a straight-chain or branched alkyl group which is bound via an oxygen atom at any position in the alkyl group and has usually from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy and the like.

The term "haloalkoxy" as used herein denotes in each case a straight-chain or branched alkoxy group having from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2dichloro-2-fluoroethoxy, 2,2,2-trichloroethoxy, pentafluoroethoxy and the like.

The term "cycloalkyl" as used herein and in the cycloalkyl moieties of cycloalkyl-alkyl denotes in each case a monocyclic saturated carbocyclic radical having usually from 3 to 6 carbon atoms, such as cyclopropyl, cyclobutyl, cyclopentyl and cyclohexyl.

The term "alkenyl" as used herein denotes in each case a singly unsaturated hydrocarbon radical having usually 3 to 6, or preferably 3 to 4 carbon atoms, such as vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein denotes in each case a straight-chain or branched alkenyl group, as defined above, having usually from 3 to 6 carbon atoms, preferably from 3 to 4 carbon atoms, wherein the hydrogen atoms of this group are partially or totally replaced with halogen atoms.

The term "alkynyl" as used herein denotes in each case a singly unsaturated hydrocarbon radical having usually from 3 to 6 carbon atoms, such as ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein denotes in each case a straight-chain or branched alkynyl group, as defined above, having usually from 3 to 6 carbon atoms, preferably from 3 to 4 carbon atoms, wherein the hydrogen atoms of this group are partially or totally replaced with halogen atoms.

The term "alkyl substituted by an alkoxy radical" as used herein refers to linear or branched alkyl having usually 1 to 4 carbon atoms, wherein 1 of those carbon atoms carries an alkoxy radical usually having 1 to 4 carbon atoms. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methylpropoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "alkyl substituted by cycloalkyl radical" as used herein refers to linear or branched alkyl having usually 1 to 2 carbon atoms, wherein 1 of those carbon atoms carries a cycloalkyl radical usually having 3 to 6 carbon atoms. Examples are $CH_2$-cylcopropyl (=cyclopropylmethyl), $CH_2$-cyclobutyl (=cyclobutylmethyl), $CH_2$-cylcopentyl (=cyclopentylmethyl), $CH_2$-cyclohexyl (=cyclohexylmethyl), $CH_2CH_2$-cylcopropyl (=2-cyclopropylethyl), $CH_2CH_2$-cyclobutyl (=2-cyclobutylethyl), $CH_2CH_2$-cylcopentyl (=2-cyclopentylethyl), $CH_2CH_2$-cyclohexyl (=2-cyclohexylethyl), $CH(CH_3)$-cylcopropyl (=1-cyclopropylethyl), $CH(CH_3)$-cyclobutyl (=1-cyclobutylethyl), $CH(CH_3)$-cylcopentyl (=1-cyclopentylethyl) or $CH(CH_3)$-cyclohexyl (=1-cyclohexylethyl).

According to a preferred embodiment of the invention, the phenyluracil herbicides (group C.2.1) are selected from benzfendizone and compounds of the formula C.2.1a and the salts thereof,

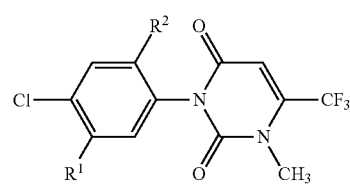

(C.2.1a)

wherein $R^1$ is selected from the group consisting of the radicals propargyloxy, allyloxy, isopropyloxy, C(=O)NHSO_2NR^{1a}R^{1b}, C(=O)N—NR^{1a}R^{1b}, C(=O)O—CR^{1a}R^{1c}—C(=O)—OR^{1e}, C(=O)O—R^{1b}, C(=O)O—CHR^{1c}—C(=O)NHSO_2NR^{1a}R^{1b}, NHSO_2NR^{1a}R^{1b}, SO_2NHC(=O)NR^{1a}R^{1b}, $CH_2$—CH(Cl)CO_2—R^{1d} and the radical of the formula OC(CH_3)_2—C(=O)—OR^{1e}; where $R^{1a}$ is hydrogen or $C_1$-$C_4$-alkyl;

$R^{1b}$ is $C_1$-$C_4$-alkyl;

$R^{1c}$ is hydrogen or $C_1$-$C_4$-alkyl;

$R^{1d}$ is hydrogen or $C_1$-$C_4$-alkyl or a agriculturally acceptable cation; and $R^{1e}$ is $C_1$-$C_4$-alkyl, propargyl or allyl; and $R^2$ is hydrogen, fluorine or chlorine.

Examples of particularly preferred compounds of formula C.2.1a include butafenacil ($R^1$=C(=O)O—C(CH_3)_2—C(=O)—OCH_2CH=CH_2, $R^2$=H), flupropacil ($R^1$=C(=O)O—CH(CH_3)_2, $R^2$=H), and saflufenacil ($R^1$=C(=O)NHSO_2N(CH_3)(CH(CH_3)_2), $R^2$=F), with a particular preference given to saflufenacil.

According to another preferred embodiment of the invention the phenyluracil herbicides (group C.2.1) are selected from compounds of the formula C.2.1b and the salts thereof, (C.2.1b)

[Chemical structure showing a benzoxazole ring system fused with a pyrimidinedione, with substituents R², R⁴, R³ᵃ, R⁵, and CF₃]

wherein R², R³ᵃ, R⁴ and R⁵ are as defined herein, and wherein R², R³ᵃ, R⁴ and R⁵, independently of each other, and more preferably in combination have one of the following meanings R² is preferably fluorine or chlorine,
R⁴ is preferably chlorine,
R⁵ is preferably methyl and
R³ᵃ is preferably selected from $C_1$-$C_4$-alkyl, $C_1$-$C_2$-haloalkyl, and $C_1$-$C_2$-alkyl substituted by a $C_3$-$C_6$-cycloalkyl radical with R³ᵃ being more preferably selected from methyl, ethyl, n-propyl, isoprobly, n-butyl, 2-methylpropyl, trifluoromethyl and cyclopropylmethyl.

Examples of particularly preferred compounds of formula C.2.1b are selected from the group of compounds of the formula C.2.1b, wherein R² is fluorine, R⁴ is chlorine, R⁵ is methyl and R³ᵃ is cyclopropylmethyl,
R² is chlorine, R⁴ is chlorine, R⁵ is methyl and R³ᵃ is cyclopropylmethyl,
R² is fluorine, R⁴ is chlorine, R⁵ is methyl and R³ᵃ is methyl,
R² is chlorine, R⁴ is chlorine, R⁵ is methyl and R³ᵃ is methyl,
R² is fluorine, R⁴ is chlorine, R⁵ is methyl and R³ᵃ is ethyl,
R² is chlorine, R⁴ is chlorine, R⁵ is methyl and R³ᵃ is ethyl,
R² is fluorine, R⁴ is chlorine, R⁵ is methyl and R³ᵃ is trifluoromethyl or
R² is chlorine, R⁴ is chlorine, R⁵ is methyl and R³ᵃ is trifluoromethyl.

An especially preferred compound of this embodiment is a compound of the formula C.2.1b, wherein R² is fluorine, R⁴ is chlorine, R⁵ is methyl and R³ᵃ is cyclopropylmethyl.

According to another preferred embodiment of the invention the phenyluracil herbicides (group C.2.1) are selected from compounds of the formula C.2.1c and the salts thereof, (C.2.1c)

[Chemical structure showing a benzimidazole fused with pyrimidinedione, with substituents R², R⁴, R³ᵇ, R⁵, HN, and CF₃]

wherein R², R³ᵇ, R⁴ and R⁵ are as defined herein, and wherein R², R³ᵃ, R⁴ and R⁵, independently of each other, and more preferably in combination have one of the following meanings R² is preferably fluorine or chlorine,
R⁴ is preferably chlorine,
R⁵ is preferably methyl and
R³ᵇ is preferably selected from $C_1$-$C_4$-alkyl, $C_1$-$C_2$-haloalkyl, and $C_1$-$C_2$-alkyl substituted by a $C_3$-$C_6$-cycloalkyl radical with R³ᵇ being more preferably selected from methyl, ethyl, n-propyl, isoprobly, n-butyl, 2-methylpropyl, trifluoromethyl and cyclopropylmethyl.

Examples of particularly preferred compounds of formula C.2.1c are selected from the group of compounds of the formula C.2.1c, wherein R² is fluorine, R⁴ is chlorine, R⁵ is methyl and R³ᵇ is cyclopropylmethyl,
R² is chlorine, R⁴ is chlorine, R⁵ is methyl and R³ᵇ is cyclopropylmethyl,
R² is fluorine, R⁴ is chlorine, R⁵ is methyl and R³ᵇ is methyl,
R² is chlorine, R⁴ is chlorine, R⁵ is methyl and R³ᵇ is methyl,
R² is fluorine, R⁴ is chlorine, R⁵ is methyl and R³ᵇ is ethyl,
R² is chlorine, R⁴ is chlorine, R⁵ is methyl and R³ᵇ is ethyl,
R² is fluorine, R⁴ is chlorine, R⁵ is methyl and R³ᵇ is trifluoromethyl or
R² is chlorine, R⁴ is chlorine, R⁵ is methyl and R³ᵇ is trifluoromethyl.

An especially preferred compound is a compound of the formula C.2.1c, wherein R² is fluorine, R⁴ is chlorine, R⁵ is methyl and R³ᵇ is trifluoromethyl.

Phenyluracil herbicides herbicides (group C.2.1) are known from e.g. G. Theodoridis "Protoporphyrinogen-IX-oxidase Inhibitors" in "Modern Crop Protection Compounds" Vol. 1, Wiley-VHC 2007, pp 153-186; C. D. S. Tomlin, "The Pesticide Manual", 13th Edition, BCPC (2003), and also from The Compendium of Pesticide Common Names http://www.alanwood.net/pesticides/.

Dicarboximide herbicides (C.2.2) include compounds of the formula C.2.2, (C.2.2)

[Chemical structure showing a phenyl ring connected to a tetrahydroisoindole-1,3-dione, with substituents R¹³, R¹⁴, R¹⁵]

wherein
R¹³ is hydrogen, fluorine or chlorine;
R¹⁴ is selected from the group consisting of propargyloxy, allyloxy, 1-methyl-2-propinyloxy, O—$CH_2CO_2$—R¹⁶, CH=C(Cl)$CO_2$—R¹⁶ and isopropyloxy;
R¹⁵ is fluorine or chlorine; or
R¹⁴ and R¹⁵ together form a moiety O—$CH_2$—C(=O)—NR¹⁷, where R¹⁷ is a propargyl radical and where the oxygen atom is meta with regard to the position of R¹³;
R¹⁶ is hydrogen, $C_1$-$C_6$-alkyl or an agriculturally acceptable cation.

Examples of compounds of formula C.2.2 include cinidon, flumioxazin, flumiclorac and flumipropyn. Also included are the salts of cinidon and flumiclorac, in particular their sodium salts, potassium salts, ammonium salts or substituted ammonium salts as defined above, in particular mono-, di and tri-$C_1$-$C_8$-alkylammonium salts such as isopropylammonium salts, and the esters of cinidon and flumiclorac, in particular their $C_1$-$C_8$-alkyl esters, such as methylesters, ethylesters, iso propyl esters. Suitable examples of such esters are cinidon-ethyl and flumiclorac-pentyl.

Dicarboximide herbicides (group C.2.2) are known from e.g. G. Theodoridis "Protoporphyrinogen-IX-oxidase Inhibitors" in "Modern Crop Protection Compounds" Vol. 1, Wiley-VHC 2007, pp 153-186; C. D. S. Tomlin, "The Pesticide Manual", 13th Edition, BCPC (2003), and also from The Compendium of Pesticide Common Names http://www.alanwood.net/pesticides/.

Triazolone and oxadiazolone herbicides (C.2.3) include in particular compounds of the formula C.2.3 and their salts,

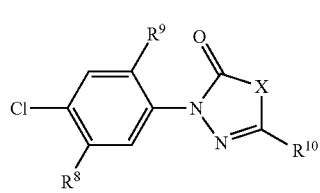

(C.2.3)

wherein

X is O or $NR^{11}$, $R^8$ is selected from the group consisting of propargyloxy, allyloxy, isopropyloxy, the radical of the formula $CH_2$—$CH(Cl)CO_2$—$R^{12}$ and the radical of the formula $NH$—$SO_2$—$CH_3$;

$R^9$ is fluorine or chlorine;

$R^{10}$ is $CH_3$, tert.-butyl;

$R^{11}$ is $CHF_2$, or together with $R^{10}$ may for 1,4-butandiyl;

$R^{12}$ is hydrogen, $C_1$-$C_6$-alkyl or a agriculturally acceptable cation.

Examples of the compounds of formula C.2.3 include azafenidin, carfentrazone, sulfentrazone, oxadiazon and oxadiargyl. Also included are the salts of carfentrazone, in particular its sodium salt, potassium salt, ammonium salt or substituted ammonium salts as defined above, in particular mono-, di and tri-$C_1$-$C_8$-alkylammonium salts such as isopropylammonium salts and the esters of carfentrazone, in particular its $C_1$-$C_8$-alkyl esters, such as methylesters, ethylesters, iso propyl esters. A suitable example of such an ester is carfentrazone-ethyl.

Triazolone and oxadiazolone herbicides (group C.2.3) are known from e.g. G. Theodoridis "Protoporphyrinogen-IX-oxidase Inhibitors" in "Modern Crop Protection Compounds" Vol. 1, Wiley-VHC 2007, pp 153-186; C. D. S. Tomlin, "The Pesticide Manual", 13th Edition, BCPC (2003), and also from The Compendium of Pesticide Common Names http://www.alanwood.net/pesticides/.

Nitrophenylether herbicides (C.2.4) include furyloxyphen and compounds of the formula C.2.4,

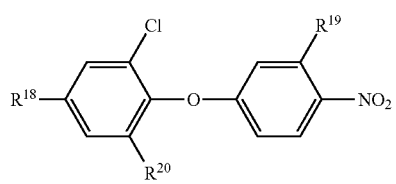

(C.2.4)

wherein $R^{18}$ is chlorine or trifluoromethyl;

$R^{19}$ is selected from the group consisting of hydrogen, $C_1$-$C_4$-alkoxy, $CO_2$—$R^{21}$, $C(=O)O$—$CH_2CO_2$—$R^{21}$, $C(=O)O$—$CH(CH_3)CO_2$—$R^{21}$, $C(=O)NH$—$SO_2$—$R^{22}$;

$R^{20}$ is hydrogen, fluorine or chlorine;

$R^{21}$ is hydrogen, $C_1$-$C_6$-alkyl or a agriculturally acceptable cation; and $R^{22}$ is $C_1$-$C_4$-alkyl.

Examples of compounds of formula C.2.4 include nitrofen, bifenox, oxyfluorfen, acifluorfen, fluoroglycofen, fluorodifen, fomesafen, lactofen, halosafen, chlornitrofen, fluornitrofen, chlomethoxyfen and nitrofluorfen and their salts and esters. In particular included are the salts of acifluorfen and fluoroglycofen, in particular the sodium salts, potassium salts, ammonium salts or substituted ammonium salts as defined above, in particular mono-, di and tri-$C_1$-$C_8$-alkylammonium salts such as isopropylammonium salts and the esters of acifluorfen and fluoroglycofen, in particular their $C_1$-$C_8$-alkyl esters, such as methylesters, ethylesters, iso propyl esters. A suitable example of such a salt is acifluorfen-sodium. Suitable examples of such esters are acifluorfen-methyl and fluoroglycofen-ethyl.

Nitrophenylether herbicides (group C.2.4) are known from e.g. G. Theodoridis "Protoporphyrinogen-IX-oxidase Inhibitors" in "Modern Crop Protection Compounds" Vol. 1, Wiley-VHC 2007, pp 153-186; C. D. S. Tomlin, "The Pesticide Manual", 13th Edition, BCPC (2003), and also from The Compendium of Pesticide Common Names http://www.alanwood.net/pesticides/.

Pyrazole type herbicides (group C.2.5) include compounds of the formula C.2.5 and the salts thereof,

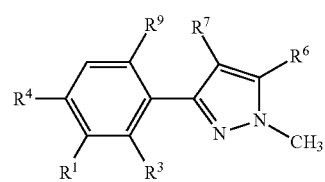

(C.2.5)

wherein $R^1$, $R^2$, $R^3$ and $R^4$ are as defined for formula C.2.1 and wherein $R^6$ is selected from difluoromethoxy, trifluoromethyl and methylsulfonyl;

$R^7$ is selected from halogen or methyl, in particular from chlorine or bromine.

According to another preferred embodiment of the invention the pyrazole type herbicides (group C.2.5) are selected from compounds of the formula C.2.5a and the salts thereof,

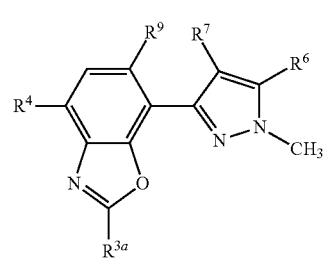

(C.2.5a)

wherein $R^2$, $R^{3a}$, $R^4$, $R^6$ and $R^7$ are as defined herein, and wherein $R^2$, $R^{3a}$, $R^4$, $R^6$ and $R^7$, independently of each other, and more preferably in combination have one of the following meanings $R^2$ is preferably fluorine or chlorine,
$R^4$ is preferably chlorine,
$R^6$ is preferably difluoromethoxy,
$R^7$ is preferably chlorine or bromine and
$R^{3a}$ is preferably selected from $C_1$-$C_4$-alkyl, $C_1$-$C_2$-haloalkyl, and $C_1$-$C_2$-alkyl substituted by a $C_3$-$C_6$-cycloalkyl radical with $R^{3a}$ being more preferably selected from methyl, ethyl, n-propyl, isoprobly, n-butyl, 2-methylpropyl, trifluoromethyl and cyclopropylmethyl.

Examples of particularly preferred compounds of formula C.2.5 are selected from the group of compounds of the formula C.2.5a, wherein $R^2$ is fluorine, $R^4$ is chlorine, $R^5$ is methyl, $R^6$ is difluoromethoxy, $R^7$ is chlorine and $R^{3a}$ is ethyl, $R^2$ is chlorine, $R^4$ is chlorine, $R^5$ is methyl, $R^6$ is difluoromethoxy, $R^7$ is chlorine and $R^{3a}$ is ethyl, $R^2$ is fluorine, $R^4$ is chlorine, $R^5$ is methyl, $R^6$ is difluoromethoxy, $R^7$ is bromine and $R^{3a}$ is ethyl, or $R^2$ is chlorine, $R^4$ is chlorine, $R^5$ is methyl, $R^6$ is difluoromethoxy, $R^7$ is bromine and $R^{3a}$ is ethyl.

According to a further preferred embodiment of the invention, the pyrazole type herbicides (group C.2.5) are selected from compounds of the formula C.2.5b and the salts thereof,

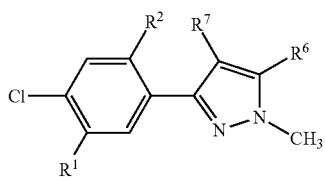

(C.2.5b)

wherein
$R^1$ is selected from the group consisting of the radicals propargyloxy, allyloxy, isopropyloxy, C(=O)NHSO$_2$NR$^{1a}$R$^{1b}$, C(=O)N—NR$^{1a}$R$^{1b}$, O—CR$^{1a}$R$^{1c}$—C(=O)—OR$^{1e}$, C(=O)O—CR$^{1a}$R$^{1c}$—C(=O)—OR$^{1e}$, C(=O)O—R$^{1b}$, C(=O)O—CHR$^{1c}$—C(=O)NHSO$_2$NR$^{1a}$R$^{1b}$, NHSO$_2$NR$^{1a}$R$^{1b}$, SO$_2$NHC(=O)NR$^{1a}$R$^{1b}$, CH$_2$—CH(Cl)CO$_2$—R$^{1d}$ and the radical of the formula OC(CH$_3$)$_2$—C(=O)—OR$^{1e}$; where $R^{1a}$ is hydrogen or $C_1$-$C_4$-alkyl;
$R^{1b}$ is $C_1$-$C_4$-alkyl;
$R^{1c}$ is hydrogen or $C_1$-$C_4$-alkyl;
$R^{1d}$ is hydrogen or $C_1$-$C_4$-alkyl or a agriculturally acceptable cation; and
$R^{1e}$ is $C_1$-$C_4$-alkyl, propargyl or allyl;
$R^2$ is hydrogen, fluorine or chlorine;
$R^6$ is selected from difluoromethoxy, trifluoromethyl and methylsulfonyl; and
$R^7$ is selected from halogen or methyl, in particular from chlorine or bromine.

Examples of particularly preferred compounds of formula C.2.5b include
fluazolate ($R^1$=C(=O)O—CH(CH$_3$)$_2$, $R^2$=F, $R^6$=trifluoromethyl, $R^7$=bromine), and
pyraflufen-ethyl ($R^1$=O—CH$_2$—C(=O)O—CH$_2$CH$_3$, $R^2$=F, $R^6$=difluoromethoxy, $R^7$=chlorine).

Triazinedione type herbicides (group C.2.6) include e.g. compounds of the formula C.2.6 and the salts thereof,

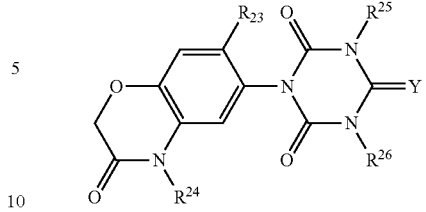

(C.2.6)

wherein
$R^{23}$ is hydrogen, fluorine or chlorine;
$R^{24}$ is selected from hydrogen, $C_1$-$C_6$-alkyl, $C_1$-$C_6$-haloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy, $C_3$-$C_6$-cycloalkyl and $C_1$-$C_2$-alkyl substituted by a $C_3$-$C_6$-cycloalkyl radical;
$R^{25}$ is selected from hydrogen, amino, methyl and propargyl;
$R^{26}$ is selected from hydrogen and methyl;
and Y is O or S.

Preference is given to compounds of the formula C.2.6, wherein Y, $R^{23}$, $R^{24}$, $R^{25}$ and $R^{26}$, independently of each other, and more preferably in combination have one of the following meanings:
Y is S,
$R^{23}$ is preferably fluorine or chlorine,
$R^{24}$ is preferably $C_3$-$C_6$-alkyl, $C_3$-$C_6$-alkenyl, or $C_3$-$C_6$-alkynyl, in particular $C_3$-$C_6$-alkynyl, and especially propargyl,
$R^{25}$ is preferably methyl, and
$R^{26}$ is preferably methyl.

In a particular preferred compound of the formula C.2.6 the variable Y is S, $R^{23}$ is fluorine, $R^{24}$ is propargyl, $R^{26}$ is methyl and $R^{26}$ is methyl.

Dicarboxamide type herbicides (group C.2.7) include e.g. compounds of the formula C.2.7 and the salts thereof,

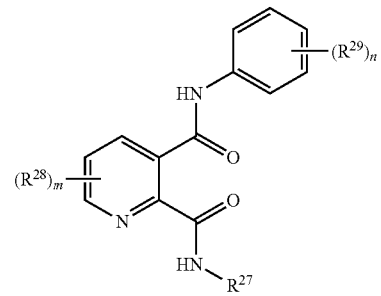

(C.2.7)

wherein
m is 0, 1, 2, or 3, in particular 1 or 2;
is 0, 1, 2, 3 or 4, in particular 1 or 2;
$R^{27}$ is selected from $C_1$-$C_6$-alkyl, $C_1$-$C_6$-haloalkyl, $C_3$-$C_6$-alkenyl, $C_3$-$C_6$-haloalkenyl, $C_3$-$C_6$-alkylnyl, $C_3$-$C_6$-haloalkylnyl, $C_3$-$C_6$-cycloalkyl, $C_1$-$C_4$-alkyl substituted by a $C_1$-$C_4$-alkoxy radical, and $C_1$-$C_2$-alkyl substituted by a $C_3$-$C_6$-cycloalkyl radical;
$R^{28}$ is selected from halogen, $C_1$-$C_3$-alkyl, $C_1$-$C_3$-haloalkyl, $C_1$-$C_3$-alkoxy, and $C_1$-$C_3$-alkyl substituted by a $C_1$-$C_3$-alkoxy radical, it being possible for m=2 or 3 that the radicals $R^{28}$ are identical or different from each other,
$R^{29}$ is selected from halogen, cyano, nitro, $C_1$-$C_4$-alkyl, $C_1$-$C_4$-haloalkyl, $C_1$-$C_4$-alkylsulfonyl, $C_1$-$C_4$-alkoxy, $C_1$-$C_4$-alkyl substituted by a $C_1$-$C_4$-alkoxy radical, $C_1$-$C_2$-alkyl substituted by a $C_3$-$C_6$-cycloalkyl radical and a radical $CO_2R^{30}$, it being possible for n=2, 3 or 4 that the radicals $R^{29}$ are identical or different from each other;

$R^{30}$ is selected from $C_1$-$C_6$-alkyl, $C_1$-$C_6$-haloalkyl, $C_3$-$C_6$-alkenyl, $C_3$-$C_6$-haloalkenyl, $C_3$-$C_6$-alkylnyl, $C_3$-$C_6$-haloalkylnyl, $C_3$-$C_6$-cycloalkyl, $C_1$-$C_4$-alkyl substituted by a $C_1$-$C_4$-alkoxy radical and $C_1$-$C_2$-alkyl substituted by a $C_3$-$C_6$-cycloalkyl radical.

Preference is given to compounds of the formula C.2.7, wherein m, n, $R^{27}$, $R^{27}$, $R^{29}$ and $R^{30}$, independently of each other, and more preferably in combination have one of the following meanings:

m is 1;
is 1, 2 or 3;
$R^{27}$ is selected from $C_1$-$C_6$-alkyl, $C_3$-$C_6$-cycloalkyl, and $C_1$-$C_2$-alkyl substituted by a $C_3$-$C_6$-cycloalkyl radical, in particular cyclopropylmethyl;
$R^{28}$ is selected from halogen and $C_1$-$C_3$-alkyl, in particular methyl;
$R^{29}$ is selected from halogen, $C_1$-$C_4$-alkyl and a radical $CO_2R^{39}$, it being possible for n=2 or 3 that the radicals $R^{29}$ are identical or different from each other;
$R^{30}$ is $C_1$-$C_6$-alkyl.

A particular preferred compound of the formula C.2.7 is the compound of the following formula C.2.7a:

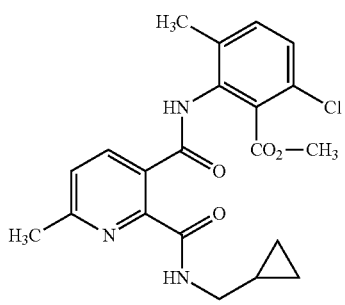

(C.2.7a)

Preferred PPO inhibitors include
pyrimidinedione herbicides (also termed as phenyluracil herbicides), in particular benzfendizone and compounds of the formula C.2.1a such as butafenacil, flupropacil and saflufenacil,
triazolinones such as azafenidin, carfentrazone and the salts and esters thereof such as carfentrazone-ethyl and sulfentrazone,
oxadiazoles such as oxadiazon and oxadiargyl,
thiadiazoles such as fluthiazet and thidiazimin,
N-phenylphthalimide herbicides (also termed as dicarboximide herbicides) such as cinidon, flumioxazin, flumiclorac, and flumipropyn,
nitrobiphenylethers such as nitrofen, bifenox, oxyfluorfen, acifluorfen, fluoroglycofen, fluorodifen, fomesafen, lactofen, halosafen, chlornitrofen, fluornitrofen, chlomethoxyfen and nitrofluorfen and the salts and esters of the aforementioned compounds.

Preferred PPO inhibitors also include
pyrimidinedione herbicides of the formulae C.2.1b and C.2.1c, in particular compounds of the formula C.2.1b, wherein
$R^2$ is fluorine, $R^4$ is chlorine, $R^5$ is methyl and $R^{3a}$ is cyclopropylmethyl,
$R^2$ is chlorine, $R^4$ is chlorine, $R^5$ is methyl and $R^{3a}$ is cyclopropylmethyl,
$R^2$ is fluorine, $R^4$ is chlorine, $R^5$ is methyl and $R^{3a}$ is methyl,
$R^2$ is chlorine, $R^4$ is chlorine, $R^5$ is methyl and $R^{3a}$ is methyl,
$R^2$ is fluorine, $R^4$ is chlorine, $R^5$ is methyl and $R^{3a}$ is ethyl,
$R^2$ is chlorine, $R^4$ is chlorine, $R^5$ is methyl and $R^{3a}$ is ethyl,
$R^2$ is fluorine, $R^4$ is chlorine, $R^5$ is methyl and $R^{3a}$ is trifluoromethyl or
$R^2$ is chlorine, $R^4$ is chlorine, $R^5$ is methyl and $R^{3a}$ is trifluoromethyl; and compounds of formula C.2.1c, wherein
$R^2$ is fluorine, $R^4$ is chlorine, $R^5$ is methyl and $R^{3b}$ is cyclopropylmethyl,
$R^2$ is chlorine, $R^4$ is chlorine, $R^5$ is methyl and $R^{3b}$ is cyclopropylmethyl,
$R^2$ is fluorine, $R^4$ is chlorine, $R^5$ is methyl and $R^{3b}$ is methyl,
$R^2$ is chlorine, $R^4$ is chlorine, $R^5$ is methyl and $R^{3b}$ is methyl,
$R^2$ is fluorine, $R^4$ is chlorine, $R^5$ is methyl and $R^{3b}$ is ethyl,
$R^2$ is chlorine, $R^4$ is chlorine, $R^5$ is methyl and $R^{3b}$ is ethyl,
$R^2$ is fluorine, $R^4$ is chlorine, $R^5$ is methyl and $R^{3b}$ is trifluoromethyl or
$R^2$ is chlorine, $R^4$ is chlorine, $R^5$ is methyl and $R^{3b}$ is trifluoromethyl.

Preferred PPO inhibitors also include pyrazole type herbicides, in particular
compounds of the formula C.2.5a, wherein
$R^2$ is fluorine, $R^4$ is chlorine, $R^5$ is methyl, $R^6$ is difluoromethoxy, $R^7$ is chlorine and $R^{3a}$ is ethyl,
$R^2$ is chlorine, $R^4$ is chlorine, $R^5$ is methyl, $R^6$ is difluoromethoxy, $R^7$ is chlorine and $R^{3a}$ is ethyl,
$R^2$ is fluorine, $R^4$ is chlorine, $R^5$ is methyl, $R^6$ is difluoromethoxy, $R^7$ is bromine and $R^{3a}$ is ethyl, or
$R^2$ is chlorine, $R^4$ is chlorine, $R^5$ is methyl, $R^6$ is difluoromethoxy, $R^7$ is bromine and $R^{3a}$ is ethyl, and
compounds of the formula C.2.5b, which are selected from fluazolate and pyraflufen-ethyl.

Preferred PPO inhibitors also include triazinedione type herbicides, in particular compounds of the formula C.2.6 and more preferably those, wherein the variable Y is S, $R^{23}$ is fluorine, $R^{24}$ is propargyl, $R^{25}$ is methyl and $R^{26}$ is methyl.

Preferred PPO inhibitors also include dicarboxamide type herbicides, in particular compounds of the formula C.2.7 and more preferably the compound of the formula C.2.7a.

The PPO inhibitor is more preferably selected from the group consisting of:
C.2.1 pyrimidinedione herbicides (also termed as phenyluracil herbicides), in particular compounds of the formulae C.2.1a, C.2.1b and C.2.1c and
C.2.2 N-phenylphthalimide herbicides (also termed as dicarboximide herbicides), in particular compounds of the formula C.2.2.

Likewise, the PPO inhibitor is more preferably selected from the group consisting of:
C.2.5 pyrazole herbicides, in particular compounds of the formula C.2.5 and most preferably of the formula C.2.5a, especially compounds of the formula C.2.5a, wherein
$R^2$ is fluorine, $R^4$ is chlorine, $R^5$ is methyl, $R^6$ is difluoromethoxy, $R^7$ is chlorine and $R^{3a}$ is ethyl, R² is chlorine, R⁴ is chlorine, R⁵ is methyl, R⁶ is difluoromethoxy, R⁷ is chlorine and R³ᵃ is ethyl,
R² is fluorine, R⁴ is chlorine, R⁵ is methyl, R⁶ is difluoromethoxy, R⁷ is bromine and R³ᵃ is ethyl, or
R² is chlorine, R⁴ is chlorine, R⁵ is methyl, R⁶ is difluoromethoxy, R⁷ is bromine and R³ᵃ is ethyl;

C.2.6 triazinedione herbicides, in particular compounds of the formula C.2.6, and most preferably a compound of the formula C.2.6, wherein the variable Y is S, R²³ is fluorine, R²⁴ is propargyl, R²⁵ is methyl and R²⁶ is methyl;

C.2.7 dicarboxamide herbicides, in particular of the formula C.2.7 and most preferably of the formula C.2.7a.

In this embodiment 2, the relative weight ratio of pyroxasulfone to herbicide C.2 is preferably in the range from 1:500 to 500:1, in particular in the range from 1:250 to 250:1 and more preferably from 100:1 to 1:100. The relative weight ratio of herbicide A to herbicide B+herbicide C.2 is preferably in the range from 1500:1 to 1:20, in particular from 1000:1 to 1:10 and more preferably from 500:1 to 1:5.

According to a particular preferred embodiment of the invention, the component c) comprises at least one pyrimidindione herbicide C.2.1 (embodiment 2.1). Preferred pyrimidindione herbicides C.2.1 are butafenacil and saflufenacil. Likewise preferred pyrimidindione herbicides C.2.1 are compounds of the formula C.2.1b, wherein R² is fluorine, R⁴ is chlorine, R⁵ is methyl and R³ᵃ is cyclopropylmethyl. Likewise preferred pyrimidindione herbicides C.2.1 are compounds of the formula C.2.1c, wherein R² is fluorine, R⁴ is chlorine, R⁵ is methyl and R³ᵃ is trifluoromethyl.

In particular preferred compositions of this embodiment 2.1, the herbicide C comprises or in particular is butafenacil.

In other particular preferred compositions of this embodiment 2.1, the herbicide C comprises or in particular is saflufenacil.

In other particular preferred compositions of this embodiment 2.1, the herbicide C comprises or in particular is a compound of the formula C.2.1 b, wherein R² is fluorine, R⁴ is chlorine, R⁵ is methyl and R³ᵃ is cyclopropylmethyl.

In other particular preferred compositions of this embodiment 2.1, the herbicide C comprises or in particular is a compound of the formula C.2.1c, wherein R² is fluorine, R⁴ is chlorine, R⁵ is methyl and R³ᵃ is trifluoromethyl.

In this embodiment 2.1 the relative weight ratio of pyroxasulfone and an herbicide of the group C.2.1 is preferably from 1:100 to 100:1 and more preferably from 50:1 to 1:50. The relative weight ratio of herbicide A to herbicide B+herbicide C.2.1 is preferably in the range from 1000:1 to 1:10 and more preferably from 500:1 to 1:5.

According to another particular preferred embodiment of the invention, the component c) comprises at least one dicarboximide herbicide of the group C.2.2 (embodiment 2.2). Preferred dicarboximide herbicides include cinidon, flumioxazin, flumiclorac, and flumipropyn. Also included are the salts of cinidon and flumiclorac, in particular their sodium salts, potassium salts, ammonium salts or substituted ammonium salts as defined above, in particular mono-, di and tri-$C_1$-$C_8$-alkylammonium salts such as isopropylammonium salts, and the esters of cinidon and flumiclorac, in particular their $C_1$-$C_8$-alkyl esters, such as methylesters, ethylesters, iso propyl esters. Suitable examples of such esters are cinidon-ethyl and flumiclorac-pentyl.

In preferred compositions of this embodiment 2.2, the herbicide C comprises or in particular is cinidon, flumioxazin, flumiclorac, or flumipropyn, or a salt or an ester of cinidon or flumiclorac.

In a particular preferred composition of this embodiment 2.2, the herbicide C comprises or in particular is flumioxazin.

In another particular preferred composition of this embodiment 2.2, the herbicide C comprises or in particular is flumiclorac.

In a further particular preferred composition of this embodiment 2.2, the herbicide C comprises or in particular is flumipropyn.

In this embodiment 2.2 the relative weight ratio of pyroxasulfone and an herbicide of the group C.2.2 is preferably from 100:1 to 1:100, in particular from 50:1 to 1:50. The relative weight ratio of herbicide A to herbicide B+herbicide C.2.2 is preferably in the range from 1000:1 to 1:10 and more preferably from 500:1 to 1:5.

According to another particular preferred embodiment of the invention, the component c) comprises at least one pyrazole herbicide of the group C.2.5 (embodiment 2.5). Preferred pyrazole herbicides include compounds of the formula C.2.5a and compounds of the formula C.2.5b, which are preferably selected from fluazolate and pyraflufen-ethyl In preferred compositions of this embodiment 2.5, the herbicide C comprises or in particular is compound of the formula C.2.5a, which is selected from the compounds, wherein R² is fluorine, R⁴ is chlorine, R⁵ is methyl, R⁶ is difluoromethoxy, R⁷ is chlorine and R³ᵃ is ethyl,
R² is chlorine, R⁴ is chlorine, R⁵ is methyl, R⁶ is difluoromethoxy, R⁷ is chlorine and R³ᵃ is ethyl,
R² is fluorine, R⁴ is chlorine, R⁵ is methyl, R⁶ is difluoromethoxy, R⁷ is bromine and R³ᵃ is ethyl, or
R² is chlorine, R⁴ is chlorine, R⁵ is methyl, R⁶ is difluoromethoxy, R⁷ is bromine and R³ᵃ is ethyl.

In a particular preferred composition of this embodiment 2.5, the herbicide C comprises or in particular is a compound of the formula C.2.5a, wherein R² is fluorine, R⁴ is chlorine, R⁵ is methyl, R⁶ is difluoromethoxy, R⁷ is chlorine and R³ᵃ is ethyl, In another particular preferred composition of this embodiment 2.5, the herbicide C comprises or in particular is a compound of the formula C.2.5a, wherein R² is chlorine, R⁴ is chlorine, R⁵ is methyl, R⁶ is difluoromethoxy, R⁷ is bromine and R³ᵃ is ethyl.

In this embodiment 2.5 the relative weight ratio of pyroxasulfone and an herbicide of the group C.2.5 is preferably from 100:1 to 1:100, in particular from 50:1 to 1:50. The relative weight ratio of herbicide A to herbicide B+herbicide C.2.5 is preferably in the range from 1000:1 to 1:50 and more preferably from 500:1 to 1:10.

According to another particular preferred embodiment of the invention, the component c) comprises at least one triazinedione herbicide of the group C.2.6 (embodiment 2.6). Preferred triazindione herbicides include compounds of the formula C.2.6, wherein wherein the variable Y is S, R²³ is fluorine, R²⁴ is propargyl, R²⁵ is methyl and R²⁶ is methyl.

In a particular preferred composition of this embodiment 2.6, the herbicide C comprises or in particular is a compound of the formula C.2.6 wherein the variable Y is S, R²³ is fluorine, R²⁴ is propargyl, R²⁵ is methyl and R²⁶ is methyl.

In this embodiment 2.6 the relative weight ratio of pyroxasulfone and an herbicide of the group C.2.6 is preferably from 100:1 to 1:100, in particular from 50:1 to 1:50. The relative weight ratio of herbicide A to herbicide B+herbicide C.2.6 is preferably in the range from 1000:1 to 1:50 and more preferably from 500:1 to 1:10.

According to another particular preferred embodiment of the invention, the component c) comprises at least one triazindione herbicide of the group C.2.7 (embodiment 2.7). Preferred triazindione herbicides include the compound of the formula C.2.7a.

In a particular preferred composition of this embodiment 2.7, the herbicide C comprises or in particular is a compound of the formula C.2.7a.

In this embodiment 2.7 the relative weight ratio of pyroxasulfone and an herbicide of the group C.2.7 is preferably from 100:1 to 1:100, in particular from 50:1 to 1:50. The relative weight ratio of herbicide A to herbicide B+herbicide C.2.7 is preferably in the range from 1000:1 to 1:50 and more preferably from 500:1 to 1:10.

According to a third preferred embodiment of the invention (embodiment 3), the herbicidal compositions of the invention additionally comprise at least one further herbicide C.3 which is a synthetic auxin. Synthetic auxins are compounds which act like the phytohormones auxins such as indole-3-acetic acid. Synthetic auxins belong to the group 0 of the HRAC classification system (see HRAC, Classification of Herbicides According to Mode of Action, http://www.plantprotection.org/hrac/MOA.html).

Herbicide compounds belonging to the group of synthetic auxins include e.g.
C.3.1 benzoic acid herbicides;
C.3.2 quinolinecarboxylic acid herbicides;
C.3.3 pyridine carboxylic acid herbicides;
C.3.4 phenoxycarboxylic acid herbicides;

Benzoic acid herbicides herbicides (C.3.1) include e.g. dicamba, tricamba, chloramben and 2,3,6-TBA (2,3,6-trichlorobenzoic acid) and the salts and esters thereof.

Quinolinecarboxylic acid herbicides herbicides (C.3.2) include e.g. quinclorac and quinmerac and the salts and esters thereof.

Pyridinecarboxylic acid herbicides herbicides (C.3.3) include e.g. aminopyralid, clopyralid, picloram, triclopyr and fluroxypyr and their salts and their esters.

Phenoxycarboxylic acid herbicides (C.3.4) include, e.g. phenoxyacetic acid herbicides such as 2,4-D, 3,4-DA, MCPA, 2,4,5-T, phenoxypropionic acid herbicides such as 2,4-DP (dichlorprop), 2,4-DP-P, 4-CPP, 3,4-DP, fenoprop, CMPP (mecoprop), CMPP-P, and phenoxybutyric acid herbicides such as 4-CPB, 2,4-DB, 3,4-DB, 2,4,5-TB, MCPB, their salts and their esters. Phenoxycarboxylic acid herbicides (b4) include 2,4-D, MCPA, 2,4-DP (dichlorprop), 2,4-DP-P, CMPP (mecoprop), CMPP-P, MCPB, their salts and their esters.

In this embodiment 3, the relative weight ratio of pyroxasulfone to herbicide of the group C.3 is preferably in the range from 1:500 to 500:1, in particular in the range from 1:250 to 250:1 and more preferably from 100:1 to 1:100. The relative weight ratio of herbicide A to herbicide B+herbicide C.3 is preferably in the range from 1500:1 to 1:20, in particular from 1000:1 to 1:10 and more preferably from 500:1 to 1:5.

According to a particular preferred embodiment of the invention, the component c) comprises at least one benzoic acid herbicide C.3.1 (embodiment 3.1).

Preferred benzoic acid herbicides C.3.1 include dicamba, tricamba, chloramben and 2,3,6-TBA (2,3,6-trichlorobenzoic acid) and the salts the esters thereof, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyl-ethylammonium, tri(hydroxyethyl)ammonium, hydroxypropylammonium, di(hydroxypropyl)ammonium and tri(hydroxypropyl) ammonium salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts are dicamba-sodium, dicamba-potassium, dicamba-methylammonium, dicamba-isopropylammonium, dicamba-olamine, dicamba-diolamine, dicamba-trolamine, tricamba-sodium, tricamba-potassium, tricamba-methylammonium, tricamba-isopropylammonium, tricamba-olamine, tricamba-diolamine, tricamba-trolamine, chloramben-ammonium, chloramben-methylammonium, chloramben-sodium, chloramben-diolamine, 2,3,6-T-sodium, 2,3,6-dimethylammonium. Suitable examples of such esters are dicamba-methyl and chloramben-methyl.

In particular preferred compositions of this embodiment 3.1, the herbicide C comprises or in particular is dicamba or a salt thereof.

In this embodiment 3.1 the relative weight ratio of pyroxasulfone and a benzoic acid herbicide is preferably from 1:250 to 250:1, in particular from 100:1 to 1:100. The relative weight ratio of herbicide A to herbicide B+herbicide C.3.1 is preferably in the range from 1000:1 to 1:10 and more preferably from 500:1 to 1:5.

According to another particular preferred embodiment of the invention, the component c) comprises at least one quinolinecarboxylic acid herbicide C.3.2 (embodiment 3.2). Quinolinecarboxylic acid herbicides (group C.2.2) are known e.g. from C. D. S. Tomlin, "The Pesticide Manual", 13th Edition, BCPC (2003), and also from The Compendium of Pesticide Common Names, http://www.alanwood.net/pesticides/.

Preferred quinolinecarboxylic acid herbicides include quinclorac, quinmerac, their salts and their esters, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters.

In particular preferred compositions of this embodiment 3.2, the herbicide B comprises or in particular is quinclorac or a salt or ester thereof.

In other particular preferred compositions of this embodiment 3.2, the herbicide B comprises or in particular is quinmerac or a salt or ester thereof.

In this embodiment 3.2 the relative weight ratio of pyroxasulfone and quinolinecarboxylic acid herbicide is preferably from 1:250 to 250:1, in particular from 100:1 to 1:100. The relative weight ratio of herbicide A to herbicide B+herbicide C.3.2 is preferably in the range from 1000:1 to 1:10 and more preferably from 500:1 to 1:5.

According to another particular preferred embodiment of the invention, the component c) comprises at least one pyridinecarboxylic acid herbicide C.3.3 (embodiment 3.3). Pyridinecarboxylic acid herbicides (group C.3.3) are known e.g. fC. D. S. Tomlin, "The Pesticide Manual", 13th Edition, BCPC (2003), and also from The Compendium of Pesticide Common Names, http://www.alanwood.net/pesticides/.

Pyridinecarboxylic acid herbicides include aminopyralid, clopyralid, picloram, triclopyr and fluroxypyr and their salts and their esters, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts and esters are aminopyralid-potassium, aminopyralid-tris(2-hydroxypropyl)ammonium, clopyralid-potassium, clopyralid-olamine, clopyralid-tris(2-hydroxypropyl)ammonium, clopyralid-methyl, picloram-potassium, picloram-triethylammonium, picloram-tris(2-hydroxypropyl)ammonium, picloram-methyl, picloram-2-ethylhexyl, picloram-isooctyl, fluroxypyr-meptyl, fluroxypyrbutomethyl, triclopyr-triethylammonium, triclopyr-ethyl and triclopyr-butotyl.

In particular preferred compositions of this embodiment 3.3, the herbicide C comprises or in particular is fluroxypyr or a salt or ester thereof.

In this embodiment 3.3 the relative weight ratio of pyroxasulfone and pyridinecarboxylic acid herbicide is preferably from 250:1 to 1:250, in particular from 100:1 to 1:100. The relative weight ratio of herbicide A to herbicide B+herbicide C.3.3 is preferably in the range from 1000:1 to 1:10 and more preferably from 500:1 to 1:5.

According to a further embodiment of the invention, the component c) comprises at least one phenoxycarboxylic acid herbicide C.3.4 (embodiment 3.4). Phenoxycarboxylic herbicides (group C.3.4) are known e.g. from C. D. S. Tomlin, "The Pesticide Manual", 13th Edition, BCPC (2003), and also from The Compendium of Pesticide Common Names, http://www.alanwood.net/pesticides/.

Preferred phenoxycarboxylic acid herbicides include 2,4-D, 2,4-DP (dichlorprop), 2,4-DP-P, CMPP (mecoprop), CMPP-P, MCPA, MCPB, their salts and their esters, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts and esters are When this substance is used as an ester or a salt, its identity should be stated, for example 2,4-D-ammonium, 2,4-D-butotyl, 2,4-D-2-butoxypropyl, 2,4-D-3-butoxypropyl, 2,4-D-butyl, 2,4-D-diethylammonium, 2,4-D-dimethylammonium, 2,4-D-diolamine, 2,4-D-dodecylammonium, 2,4-D-ethyl, 2,4-D-2-ethylhexyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, MCPA-butotyl, MCPA-butyl, MCPA-dimethylammonium, MCPA-diolamine, MCPA-ethyl, MCPA-2-ethylhexyl, MCPA-isobutyl, MCPA-isoctyl, MCPA-isopropyl, MCPA-methyl, MCPA-olamine, MCPA-potassium, MCPA-sodium, MCPA-trolamine, dichlorprop-butotyl, dichlorprop-dimethylammonium, dichlorprop-ethylammonium, dichlorprop-2-ethylhexyl, dichlorprop-isoctyl, dichlorprop-methyl, dichlorprop-potassium, dichlorprop-sodium, dicloprop-P-dimethylammonium, mecoprop-dimethylammonium, mecoprop-diolamine, mecoprop-ethadyl, mecoprop-isoctyl, mecoprop-methyl, mecoprop-potassium, mecoprop-sodium, mecoprop-trolamine, mecoprop-P-dimethylammonium, mecoprop-P-isobutyl, mecoprop-P-potassium, MCPB-methyl, MCPB-ethyl and MCPB-sodium.

In particular preferred compositions of this embodiment, the herbicide C comprises or in particular is 2,4-D or a salt or ester thereof.

In particular preferred compositions of this embodiment, the herbicide C comprises or in particular is MCPA or a salt or ester thereof.

In particular preferred compositions of this embodiment, the herbicide C comprises or in particular is dicloprop, dicloprop-P or a salt or ester thereof.

In particular preferred compositions of this embodiment, the herbicide C comprises or in particular is mecoprop, mecoprop-P or a salt or ester thereof.

In particular preferred compositions of this embodiment, the herbicide C comprises or in particular is MCPB or a salt or ester thereof.

In this embodiment 3.4 the relative weight ratio of pyroxasulfone and phenoxycarboxylic acid herbicide is preferably from 500:1 to 1:500, in particular from 250:1 to 1:250. The relative weight ratio of herbicide A to herbicide B+herbicide C.3.4 is preferably in the range from 1000:1 to 1:10 and more preferably from 500:1 to 1:5.

According to a fourth preferred embodiment of the invention (embodiment 4), the herbicidal compositions of the invention additionally comprise at least one further herbicide C.4 which is an inhibitor of 4-hydroxyphenylpyruvate dioxygenase (HPPD inhibitor). HPPD inhibitors belong to the group F2 of the HRAC classification system (see HRAC, Classification of Herbicides According to Mode of Action, http://www.plantprotection.org/hrac/MOA.html).

Herbicide compounds belonging to the group of HPPD inhibitors include topramezone, tembotrione, isoxaflutole, mesotrione and sulcotrione.

Isoxaflutole is a well known herbicide and commercially available, e.g. under the trade name BALANCE® and MERLIN®. Mesotrione is a well known herbicide and commercially available, e.g. under the trade name CALLISTO®. Sulcotrione is a well known herbicide and commercially available, e.g. under the trade name MIKADO®. Tropramzeone is a well known herbicide and commercially available, e.g. under the trade names IMPACT® and CLIO®.

In a particular preferred compositions of this embodiment 4, the herbicide C comprises or in particular is isoxaflutole.

In another particular preferred compositions of this embodiment 4, the herbicide C comprises or in particular is mesotrione.

In a further particular preferred compositions of this embodiment 4, the herbicide C comprises or in particular is sulcotrione.

In a further particular preferred compositions of this embodiment 4, the herbicide C comprises or in particular is tembotrione.

In another particular preferred compositions of this embodiment 4, the herbicide C comprises or in particular is topramezone.

In the compositions of this embodiment 4, the relative weight ratio of pyroxasulfone to herbicide C.4 is preferably in the range from 1:100 to 100:1 and more preferably from 50:1 to 1:50. The relative weight ratio of herbicide A to herbicide B+herbicide C.4 is preferably in the range from 1500:1 to 1:20, in particular from 1000:1 to 1:10 and more preferably from 500:1 to 1:5.

According to a fifth preferred embodiment of the invention (embodiment 5), the herbicidal compositions of the invention additionally comprise at least one further herbicide C.5 which is an inhibitor of the phytoene desaturase (PDS inhibitor). PDS inhibitors are compounds which have a mode of action comprising the inhibition of the carotenoid biosynthesis in plants at the phytoene desaturase step and which belong to the group F1 of the HRAC classification system (see HRAC, Classification of Herbicides According to Mode of Action, http://www.plantprotection.org/hrac/MOA.html).

Suitable PDS inhibitors of the group C.5 are known from e.g. G. Hamprecht et al. "Phytoene Desaturase Inhibitors" in "Modern Crop Protection Compounds" Vol. 1, Wiley-VHC 2007, pp 187-211; from EP 723960 [C. D. S. Tomlin, "The Pesticide Manual", 13th Edition, BCPC (2003) and also from The Compendium of Pesticide Common Names http://www.alanwood.net/pesticides/.

Suitable PDS inhibitors of the group C.5 include e.g. pyridazinone herbicides, such as norflurazon, pyridinecarboxamide herbicides, such as flufenican, diflufenican and picolinafen, as well as herbicides not belonging to a common group, such as beflubutamid, fluridone, flurochloridone and flurtamone. Preferred PDS inhibitors according to the present invention are selected from the group consisting of pyridinecarboxamide herbicides, such as flufenican, diflufenican and picolinafen.

In particular preferred compositions of this embodiment 5, the herbicide C comprises or in particular is picolinafen. This compound is known e.g. from EP 447004 (Shell Int. Res.).

In other particular preferred compositions of this embodiment, the herbicide C comprises or in particular is diflufenican. This compound is known e.g. from EP 53011 (May & Baker Ltd.).

In the compositions of the embodiment 5 the relative weight ratio of pyroxasulfone to herbicide C.5 is preferably in the range from 1:200 to 200:1 and more preferably from 100:1 to 1:100. The relative weight ratio of herbicide A to herbicide B+herbicide C.5 is preferably in the range from 1500:1 to 1:20, in particular from 1000:1 to 1:10 and more preferably from 500:1 to 1:5.

According to a sixth preferred embodiment of the invention (embodiment 6), the herbicidal compositions of the invention additionally comprise at least one further herbicide C.6 which is an inhibitor of electron transfer in photosynthesis in plants. These compounds have a mode of action comprising the inhibition of the electron transfer in photosystem II of the photosynthesis in plants (PSII inhibitors). They belong to the groups C1 to C3 of the HRAC classification system (see HRAC, Classification of Herbicides According to Mode of Action, http://www.plantprotection.org/hrac/MOA.html).

Suitable PSII inhibitors are selected from the group consisting of:
C.6.1 arylurea herbicides;
C.6.2 triazin(di)one herbicides;
C.6.3 chlorotriazine herbicides;
C.6.4 pyridazinone herbicides;
C.6.5 phenylcarbamate herbicides;
C.6.6 nitrile herbicides;
C.6.7 bentazone and its salts such as bentazone sodium; and
C.6.8 methylthiotriazine herbicides.

PSII inhibitors are known e.g. from K.-W. Winks and K.-H. Müller "Photosynthesis Inhibitors" in "Modern Crop Protection Compounds" Vol. 1, Wiley-VHC 2007, pp 359-400; C. D. S. Tomlin, "The Pesticide Manual", 13th Edition, BCPC (2003) and also from The Compendium of Pesticide Common Names, http://www.alanwood.net/pesticides/.

Arylurea herbicides herbicides (C.6.1) include e.g. chlorbromuron, chlorotoluron, chloroxuron, dimefuron, diuron, ethidimuron, fenuron, fluometuron, isoproturon, isuron, linuron, methabenzthiazuron, metobromuron, metoxuron, monolinuron, neburon, siduron, tetrafluron and thebuthiuron. Preferred arylurea herbicides herbicides (C.6.1) include chlortoluron, diuron, linuron, isoproturon and tebuthiuron.

Triazin(di)one herbicides (C.6.2) (i.e. triazinone and triazindione herbicides) include e.g. ametridione, amibuzin, hexazinone, isomethiozin, metamitron and metribuzin. Preferred triazin(di)one herbicides (C.6.2) include hexazinon, metamitron and metribuzin.

Chlorotriazine herbicides (C.6.3) include e.g. atrazine, chlorazine, cyanazine, cyprazine, eglinazine, ipazine, mesoprazine, procyazine, proglinazine, propazine, sebuthylazine, simazine, terbuthylazine and trietazine. Preferred chlorotriazine herbicides (C.6.3) include atrazine, terbuthylazine and simazine.

Pyridazinone herbicides (C.6.4) include e.g. brompyrazon, chloridazon, dimidazon, metflurazon, norflurazon, oxapyrazon and pydanon. A preferred pyridazinone herbicide is chloridazon.

Phenylcarbamate herbicides (C.6.5) include e.g. desmedipham, phenisopham, phenmedipham and phenmedipham-ethyl.

Nitrile herbicides (C.6.6) include e.g. bromobonil, bromoxynil, chloroxynil, dichlobenil, iodobonil and ioxynil and their salts and esters, in particular in case of bromoxynil, chloroxynil and ioxynil. A preferred nitrile herbicide is bromoxynil.

Benzothiadiazinone herbicides (C.6.7) include bentazone and its salts, in particular its alkalimetal salts such as bentazone-sodium.

Methylthiotriazine herbicides (C.6.8) include e.g. ametryn, aziprotryne, cyanatryn, desmetryn, dimethametryn, methoprotryne, prometryn, simetryn and terbutryn. A preferred methylthiotriazine herbicide is ametryn.

In the compositions of the embodiment 6 the relative weight ratio of pyroxasulfone to herbicide C.6 is preferably in the range from 1:500 to 500:1, in particular in the range from 1:250 to 250:1 and more preferably from 100:1 to 1:100. The relative weight ratio of herbicide A to herbicide B+herbicide C.16 is preferably in the range from 1500:1 to 1:20, in particular from 1000:1 to 1:10 and more preferably from 500:1 to 1:5.

Particular preference is given to PSII inhibitors of the herbicide groups

C.6.1, in particular chlortoluron, diuron, linuron, isoproturon and/or tebuthiuron C.6.2, in particular hexazinon, metamitron and/or metribuzin, C.6.3, in particular atrazine and/or terbuthylazine and C.6.8, in particular ametryn, and mixtures thereof.

More preference is given to compostions of the embodiment 6, where the PSII inhibitor is selected from the group of atrazine, terbuthylazin, ametryn, hexazinone, metribuzin, diuron, isoproturon and their agriculturally acceptable salts and mixtures thereof.

In particular preferred compositions of this embodiment 6, the herbicide C comprises or in particular is hexazinone.

In other particular preferred compositions of this embodiment 6, the herbicide C comprises or in particular is metribuzin.

In other particular preferred compositions of this embodiment 6, the herbicide C comprises or in particular is diuron.

In other particular preferred compositions of this embodiment 6, the herbicide C comprises or in particular is isoproturon.

In other particular preferred compositions of this embodiment 6, the herbicide C comprises or in particular is atrazine.

In other particular preferred compositions of this embodiment 6, the herbicide C comprises or in particular is ametryn.

In other particular preferred compositions of this embodiment 6, the herbicide C comprises or in particular is terbuthylazin.

In other particular preferred compositions of this embodiment 6, the herbicide C comprises or in particular is a mixture of atrazine and ametryn.

In other particular preferred compositions of this embodiment 6, the herbicide C comprises or in particular is a mixture of atrazine and metribuzin.

According to a seventh preferred embodiment of the invention (embodiment 7), the herbicidal compositions of the invention additionally comprise at least one further herbicide C.7 which is an inhibitor of microtubule assembly (MTA inhibitor). MTA inhibitors are compounds which have a mode of action comprising the inhibition of the microtubule assembly in plants and which belong to the group K1 of the HRAC classification system (see HRAC, Classification of Herbicides According to Mode of Action, http://www.plantprotection.org/hrac/MOA.html).

MTA inhibitors include e.g. dinitroanilide herbicides, such as benfluralin, butralin, dinitramine, ethalfluralin, oryzalin, pendimethalin, and trifluralin, phosphoroamidate herbicides, such as amiprophos-methyl and butamiphos, pyridine herbicides, such as dithiopyr and thiazopyr, benzamide herbicides, such as propyzamide and tebutam, and benzoic acid herbicides, such as chlorthal. The term "MTA inhibitor" is meant herein to also include the respective salts, isomers and esters of the above mentioned compounds. Suitable salts are e.g. salts of alkaline or earth alkaline metals or ammonium or organoammonium salts, for instance, sodium, potassium, ammonium, isopropyl ammonium etc. Suitable isomers are e.g. stereo isomers such as the enantiomers. Suitable esters are e.g. $C_1$-$C_8$-(branched or non-branched) alkyl esters, such as methylesters, ethylesters, iso propyl esters.

Preferred MTA inhibitors according to the present invention are selected from the group consisting of dinitroaniline herbicides, in particular benfluralin, butralin, dinitramine, ethalfluralin, fluchloralin, isopropalin, methalpropalin, nitralin, oryzalin, pendimethalin, prodiamine, profluralin and trifluralin, more preferably oryzalin, pendimethalin and trifluralin. Dinitroaniline herbicides are known e.g. from U.S. Pat. No. 3,257,190; U.S. Pat. No. 3,321,292; U.S. Pat. No. 3,367,949; C. D. S. Tomlin, "The Pesticide Manual", 13th Edition, BCPC (2003) and also from The Compendium of Pesticide Common Names, http://www.alanwood.net/pesticides/.

In the compositions of the embodiment 7 the relative weight ratio of pyroxasulfone to herbicide C.7 is preferably in the range from 1:500 to 100:1 and more preferably from 50:1 to 1:300. The relative weight ratio of herbicide A to herbicide B+herbicide C.7 is preferably in the range from 1500:1 to 1:100, in particular from 1000:1 to 1:80 and more preferably from 500:1 to 1:50.

In particular preferred compositions of this embodiment 7, the herbicide C comprises or in particular is oryzalin.

In further particular preferred compositions of this embodiment 7, the herbicide C comprises or in particular is pendimethalin.

In the particular preferred compositions of embodiment 7 the relative weight ratio of pyroxasulfone and dinitroaniline herbicide is preferably from 100:1 to 1:500 and more preferably from 50:1 to 1:300. The relative weight ratio of herbicide A to herbicide B+herbicide C.7 is preferably in the range from 1500:1 to 1:100, in particular from 1000:1 to 1:80 and more preferably from 500:1 to 1:80.

According to a eighth preferred embodiment of the invention (embodiment 8), the herbicidal compositions of the invention additionally comprise at least one further herbicide C.8 which is an inhibitor of the VLCFA synthesis (VLCFA inhibitor). VLCFA inhibitors are compounds which have a mode of action comprising the inhibition of the VLCA synthesis and/or the inhibition of cell division in plants and which belong to the group K3 of the HRAC classification system (see HRAC, Classification of Herbicides According to Mode of Action, http://www.plantprotection.org/hrac/MOA.html).

VLCFA inhibitors include e.g.

C.8.1 chloroacetamide herbicides, such as acetochlor, alachlor, butachlor, dimethachlor, dimethenamid, dimethenamid-P, metazachlor, metolachlor, S-metolachlor, pethoxamid, pretilachlor, propachlor, propisochlor and thenylchlor, C.8.1 oxyacetamide herbicides, such as flufenacet and mefenacet, C.8.3 acetamide herbicides, such as diphenamid, napropamide and naproanilide, C.8.3 tetrazolinone herbicides, such as fentrazamide as well as C.8.4 VLCFA-herbicides not belonging to a common group, such as anilofos, cafenstrole and piperophos.

The term "VLCFA inhibitor" is meant herein to also include the respective salts, isomers and esters of the above mentioned compounds. Suitable salts are e.g. salts of alkaline or earth alkaline metals or ammonium or organoammonium salts, for instance, sodium, potassium, ammonium, isopropyl ammonium etc. Suitable isomers are e.g. stereo isomers such as the enantiomers. Suitable esters are e.g. $C_1$-$C_8$-(branched or non-branched) alkyl esters, such as methylesters, ethylesters, iso propyl esters.

Preferred VLCFA inhibitors according to the embodiment 8 are selected from the group consisting of chloroacetamide herbicides (embodiment 8.1), in particular acetochlor, dimethachlor, dimethenamid, dimethenamid-P, metazachlor, propisochlor, pethoxamide, metolachlor, and metolachlor-S and oxyacetamide herbicides (embodiment 8.2), in particular flufenacet.

In the compositions of the embodiment 8 (and likewise in embodiments 8.1 and 8.2) the relative weight ratio of pyroxasulfone to herbicide C.8 is preferably in the range from 1:250 to 250:1, in particular in the range of 1:200 to 200:1 and more preferably from 150:1 to 1:150. The relative weight ratio of herbicide A to herbicide B+herbicide C.8 is preferably in the range from 1500:1 to 1:20 and more preferably from 1000:1 to 1:10.

In particular preferred compositions of this embodiment 8.1, the herbicide C comprises or in particular is acetochlor.

In other particular preferred compositions of this embodiment 8.1, the herbicide C comprises or in particular is dimethachlor.

In further particular preferred compositions of this embodiment 8.1, the herbicide C comprises or in particular is dimethenamid.

In further particular preferred compositions of this embodiment 8.1, the herbicide C comprises or in particular is dimethenamid-P.

In further particular preferred compositions of this embodiment 8.1, the herbicide C comprises or in particular is metazachlor.

In further particular preferred compositions of this embodiment 8.1, the herbicide C comprises or in particular is propisochlor.

In further particular preferred compositions of this embodiment 8.2, the herbicide C comprises or in particular is flufenacet.

In further preferred compositions of this embodiment 8, the herbicide C comprises or in particular is a mixture of at least one VLCFA inhibitor herbicide, in particular at least one chloroacetamide herbicide and/or at least one oxyacetamide, with at least one herbicides of the group C.3, in particular of the group C.3.1 such as dicamba or a salt thereof, or of the group C.3.2 such as quinmerac or a salt thereof (embodiment 8.3) and/or with clomazone (embodiment 8.4). In these preferred compositions of the embodiments 8.3 and 8.4 the chloroacetamide herbicide is preferably selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In further particular preferred compositions of this embodiment 8.3, the herbicide C comprises or in particular is a mixture of quinmerac or a salt thereof and metazachlor.

In further particular preferred compositions of this embodiment 8.3, the herbicide C comprises or in particular is a mixture of dicamba or a salt thereof and metazachlor.

In further particular preferred compositions of this embodiment 8.3, the herbicide C comprises or in particular is a mixture of dicamba or a salt thereof and flufenacet.

In further particular preferred compositions of this embodiment 8.3, the herbicide C comprises or in particular is a mixture of dicamba or a salt thereof and dimethenamid-P, optionally comprising a PSII inhibitor herbicide such as atrazine or metribuzin.

In further particular preferred compositions of this embodiment 8.4, the herbicide C comprises or in particular is a mixture of clomazone and metazachlor.

In further particular preferred compositions of this embodiment 8.4, the herbicide C comprises or in particular is a mixture of clomazone and dimethenamid-P.

In the embodiment 8.3 the relative weight ratio of pyroxasulfone and herbicide C.8+C.3 is preferably from 500:1 to 1:500 and more preferably from 250:1 to 1:250. The relative weight ratio of herbicide A to herbicide B+herbicide C.3+herbicide C.8 is preferably in the range from 1000:1 to 1:50 and more preferably from 500:1 to 1:30.

In the embodiment 8.4 the relative weight ratio of pyroxasulfone and herbicide C.8+clomazone is preferably from 500:1 to 1:500 and more preferably from 250:1 to 1:250. The relative weight ratio of herbicide A to herbicide B+clomazone+herbicide C.8 is preferably in the range from 1000:1 to 1:50 and more preferably from 500:1 to 1:30.

In further preferred compositions of the invention, the herbicide C comprises or in particular is a mixture of an VLCFA inhibitor, in particular an oxyacetamide and/or a chloroacetamide, and at least one PSII inhibitor, in particular selected from the groups C.6.1, C.6.2, C.6.3 and C.6.8 (embodiment 8.5).

In the preferred compositions of the embodiment 8.5 the chloroacetamide herbicide is preferably selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In the preferred compositions of the embodiment 8.5 the PSII-inhibitor is preferably selected from atrazine, terbuthylazin, ametryn, hexazinone, metribuzin, diuron, isoproturon.

In particular preferred compositions of this embodiment 8.5, the herbicide C comprises or in particular is a mixture of dimethenamid-P and at least one PSII inhibitor selected from atrazine, metribuzine and terbuthylazine.

In further particular preferred compositions of this embodiment 8.5, the herbicide C comprises or in particular is a mixture of metazachlor and at least one PSII inhibitor selected from atrazine, metribuzine and terbuthylazine.

In further particular preferred compositions of this embodiment 8.5, the herbicide C comprises or in particular is a mixture of alachlor and at least one PSII inhibitor selected from atrazine, metribuzine and terbuthylazine.

In further particular preferred compositions of this embodiment 8.5, the herbicide C comprises or in particular is a mixture of flufenacet and at least one PSII inhibitor selected from atrazine, metribuzine and terbuthylazine.

In the embodiment 8.5 the relative weight ratio of pyroxasulfone and herbicide C.8+C.6 is preferably from 500:1 to 1:500 and more preferably from 250:1 to 1:250. The relative weight ratio of herbicide A to herbicide B+herbicide C.6+herbicide C.8 is preferably in the range from 1000:1 to 1:50 and more preferably from 500:1 to 1:30.

In further preferred compositions of the invention, the herbicide C comprises or in particular is a mixture of an VLCFA inhibitor, in particular an oxyacetamide and/or a chloroacetamide, at least one auxin herbicide C.3, in particular a herbicide of the groups C.3.1, C.3.2 and/or C.3.4, and at least one PSII inhibitor, in particular selected from the groups C.6.1, C.6.2, C.6.3 and C.6.8 (embodiment 8.6).

In the preferred compositions of the embodiment 8.6 the auxin herbicide C.3 is at least one benzoic acid herbicide of the group C.3.1, such as dicamba or a salt thereof, or quinolinecarboxylic acid herbicide of the group C.3.2 such as quinmerac or a salt thereof.

In the preferred compositions of the embodiment 8.6 the chloroacetamide herbicide is preferably selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In the preferred compositions of the embodiment 8.6 the PSII-inhibitor is preferably selected from atrazine, terbuthylazin, ametryn, hexazinone, metribuzin, diuron, isoproturon.

In particular preferred compositions of this embodiment 8.6, the herbicide C comprises or in particular is a mixture of dimethenamid-P, at least one PSII inhibitor selected from atrazine, metribuzine and terbuthylazine, and an auxin herbicide, in particular a benzoic acid herbicide such as dicamba.

In particular preferred compositions of this embodiment 8.6, the herbicide C comprises or in particular is a mixture of metazachlor, at least one PSII inhibitor selected from atrazine, metribuzine and terbuthylazine, and an auxin herbicide, in particular a benzoic acid herbicide such as dicamba.

In particular preferred compositions of this embodiment 8.6, the herbicide C comprises or in particular is a mixture of alachlor, at least one PSII inhibitor selected from atrazine, metribuzine and terbuthylazine, and an auxin herbicide, in particular a benzoic acid herbicide such as dicamba.

In particular preferred compositions of this embodiment 8.6, the herbicide C comprises or in particular is a mixture of flufenacet, at least one PSII inhibitor selected from atrazine, metribuzine and terbuthylazine, and an auxin herbicide, in particular a benzoic acid herbicide such as dicamba.

In the embodiment 8.6 the relative weight ratio of pyroxasulfone and herbicide C.8+C.6+C.3 is preferably from 500:1 to 1:500 and more preferably from 250:1 to 1:250. The relative weight ratio of herbicide A to herbicide B+herbicide C.3+herbicide C.6+herbicide C.8 is preferably in the range from 1000:1 to 1:50 and more preferably from 500:1 to 1:30.

In further preferred compositions of the invention, the herbicide C comprises or in particular is a mixture of an VLCFA inhibitor, in particular an oxyacetamide and/or a chloroacetamide, and at least one protoporphyrinogen oxidase inhibitor which is in particular selected from the groups C.2.1 and C.2.2 (embodiment 8.7).

In the preferred compositions of the embodiment 8.7 the PPO inhibitor herbicide is select from the group of pyrimidinedione herbicides, in particular saflufenacil or a salt thereof.

In the preferred compositions of the embodiment 8.7 the chloroacetamide herbicide is preferably selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In the embodiment 8.7 the relative weight ratio of pyroxasulfone and herbicide C.2+C.8 is preferably from 200:1 to 1:200 and more preferably from 100:1 to 1:100. The relative weight ratio of herbicide A to herbicide B+herbicide C.2+herbicide C.8 is preferably in the range from 1000:1 to 1:10 and more preferably from 500:1 to 1:10.

In further preferred compositions of the invention, the herbicide C comprises or in particular is a mixture of an VLCFA inhibitor, in particular an oxyacetamide and/or a chloroacetamide, and at least one HPPD inhibitor (embodiment 8.8).

In the preferred compositions of the embodiment 8.8 the HPPD inhibitor herbicide is select from the group of topramezone, tembotrione, isoxaflutole, mesotrione and sulcotrione or a salt thereof.

In the preferred compositions of the embodiment 8.8 the chloroacetamide herbicide is preferably selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In the embodiment 8.8 the relative weight ratio of pyroxasulfone and herbicide C.4+C.8 is preferably from 200:1 to 1:200 and more preferably from 100:1 to 1:100. The relative weight ratio of herbicide A to herbicide B+herbicide C.4+herbicide C.8 is preferably in the range from 1500:1 to 1:20 and more preferably from 1000:1 to 1:10.

In further preferred compositions of the invention, the herbicide C comprises or in particular is a mixture of an VLCFA inhibitor, in particular an oxyacetamide and/or a chloroacetamide, at least one HPPD inhibitor herbicide C.4 and at least one PSII inhibitor, in particular selected from the groups C.6.1, C.6.2, C.6.3 and C.6.8 (embodiment 8.9).

In the preferred compositions of the embodiment 8.9 the HPPD inhibitor herbicide is select from the group of topramezone, tembotrione, isoxaflutole, mesotrione and sulcotrione or a salt thereof.

In the preferred compositions of the embodiment 8.9 the chloroacetamide herbicide is preferably selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In the preferred compositions of the embodiment 8.9 the PSII-inhibitor is preferably selected from atrazine, terbuthylazin, ametryn, hexazinone, metribuzin, diuron, isoproturon and terbuthiuron.

In particular preferred compositions of this embodiment 8.9, the herbicide C comprises or in particular is a mixture of dimethenamid-P, at least one PSII inhibitor selected from atrazine, metribuzine and terbuthylazine, and a HPPD inhibitor herbicide, in particular topramezone.

In particular preferred compositions of this embodiment 8.9, the herbicide C comprises or in particular is a mixture of metazachlor, at least one PSII inhibitor selected from atrazine, metribuzine and terbuthylazine, and a HPPD inhibitor herbicide, in particular topramezone.

In particular preferred compositions of this embodiment 8.9, the herbicide C comprises or in particular is a mixture of alachlor, at least one PSII inhibitor selected from atrazine, metribuzine and terbuthylazine, and a HPPD inhibitor herbicide, in particular topramezone.

In particular preferred compositions of this embodiment 8.9, the herbicide C comprises or in particular is a mixture of flufenacet, at least one PSII inhibitor selected from atrazine, metribuzine and terbuthylazine, and a HPPD inhibitor herbicide, in particular topramezone.

In the embodiment 8.9 the relative weight ratio of pyroxasulfone and herbicide C.8+C.6+C.4 is preferably from 200:1 to 1:500 and more preferably from 100:1 to 1:250. The relative weight ratio of herbicide A to herbicide B+herbicide C.4+herbicide C.6+herbicide C.8 is preferably in the range from 1500:1 to 1:50 and more preferably from 500:1 to 1:30.

In further preferred compositions of the invention, the herbicide C comprises or in particular is a mixture of an VLCFA inhibitor, in particular an oxyacetamide and/or a chloroacetamide, and at least one herbicide of the group of microtubulin inhibitors (embodiment 8.10).

In the preferred compositions of the embodiment 8.10 the MTA inhibitor herbicide (herbicide C.7) is select from the group of dinitroanilines, in particular pendimethalin.

In the preferred compositions of the embodiment 8.10 the chloroacetamide herbicide is preferably selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In the embodiment 8.10 the relative weight ratio of pyroxasulfone and herbicide C.7+C.8 is preferably from 500:1 to 1:500 and more preferably from 250:1 to 1:250. The relative weight ratio of herbicide A to herbicide B+herbicide C.7+herbicide C.8 is preferably in the range from 1500:1 to 1:50 and more preferably from 1000:1 to 1:30.

In further preferred compositions of the invention, the herbicide C comprises or in particular is a mixture of an imidazolinone herbicide or a salt thereof and at least one PSII inhibitor, in particular selected from the groups C.6.1, C.6.2, C.6.3 and C.6.8 (embodiment 9).

In the preferred compositions of the embodiment 9 the imidazolinone herbicide is preferably selected from imazamox, imazapic, imazapyr, imazaquin, imazethapyr, their salts and their esters, as well as mixtures thereof, in particular imazamox, imazapic, imazapyr and imazethapyr, their salts and their esters, as well as mixtures thereof, in particular mixtures of imazamox with imazapyr and/or imazethapyr and mixtures of imazapic with imazapyr and/or imazethapyr.

In the preferred compositions of the embodiment 9 the PSII-inhibitor is preferably selected from atrazine, terbuthylazin, ametryn, hexazinone, metribuzin, diuron, isoproturon.

In the embodiment 9 the relative weight ratio of pyroxasulfone and herbicide C.1.1+C.6 is preferably from 500:1 to 1:500 and more preferably from 250:1 to 1:250. The relative weight ratio of herbicide A to herbicide B+herbicide C.1.1+herbicide C.6 is preferably in the range from 1000:1 to 1:50 and more preferably from 500:1 to 1:30.

In further preferred compositions of the invention, the herbicide C comprises or in particular is a mixture of an HPPD-inhibitor herbicide or a salt thereof and at least one PSII inhibitor, in particular selected from the groups C.6.1, C.6.2, C.6.3 and C.6.8 (embodiment 10).

In the preferred compositions of the embodiment 10 the HPPD-inhibitor herbicide is preferably selected from isoxaflutole, mesotrione, tembotrione, sulcotrione and tropamezone, their salts, as well as mixtures thereof.

In the preferred compositions of the embodiment 9 the PSII-inhibitor is preferably selected from atrazine, terbuthylazin, ametryn, hexazinone, metribuzin, diuron, isoproturon.

In the embodiment 10 the relative weight ratio of pyroxasulfone and herbicide C.4+C.6 is preferably from 500:1 to 1:500 and more preferably from 250:1 to 1:250. The relative weight ratio of herbicide A to herbicide B+herbicide C.4+herbicide C.8 is preferably in the range from 1000:1 to 1:50 and more preferably from 500:1 to 1:30.

In further preferred compositions of the invention, the herbicide C comprises or in particular is a mixture of an ALS-inhibitor herbicide, in particular an imidazolinone herbicide or a salt thereof and at least one protoporphyrinogen oxidase inhibitor, in particular selected from the groups C.2.1 and C.2.2, C.2.5, C.2.6 and C.2.7 (embodiment 11).

In the preferred compositions of the embodiment 11 the imidazolinone herbicide is preferably selected from imazamox, imazapic, imazapyr, imazaquin, imazethapyr, their salts and their esters, as well as mixtures thereof, in particular imazamox, imazapic, imazapyr and imazethapyr, their salts and their esters, as well as mixtures thereof, in particular mixtures of imazamox with imazapyr and/or imazethapyr and mixtures of imazapic with imazapyr and/or imazethapyr.

In the preferred compositions of the embodiment 11 the PPO inhibitor herbicide is select from the group of pyrimidinedione herbicides, in particular saflufenacil or a salt thereof.

In other preferred compositions of the embodiment 11 the PPO inhibitor herbicide is select from the group of pyrimidinedione herbicides of the formulae C.2.1b or C.2.1c, in particular the compound of the formula C.2.1b, wherein $R^2$ is fluorine, $R^4$ is chlorine, $R^5$ is methyl and $R^{3a}$ is cyclopropylmethyl, and the compound of the formula C.2.1c, wherein $R^2$ is fluorine, $R^4$ is chlorine, $R^5$ is methyl and $R^{3a}$ is trifluoromethyl In other preferred compositions of the embodiment 11 the PPO inhibitor herbicide is select from the group of pyrazole herbicides of the formulae C.2.5, in particular compounds of the formula C2.5a, and more preferably the compounds of the formula C.2.5a, wherein $R^2$ is fluorine, $R^4$ is chlorine, $R^5$ is methyl, $R^6$ is difluoromethoxy, $R^7$ is chlorine and $R^{3a}$ is ethyl,
$R^2$ is chlorine, $R^4$ is chlorine, $R^5$ is methyl, $R^6$ is difluoromethoxy, $R^7$ is chlorine and $R^{3a}$ is ethyl,
$R^2$ is fluorine, $R^4$ is chlorine, $R^5$ is methyl, $R^6$ is difluoromethoxy, $R^7$ is bromine and $R^{3a}$ is ethyl, or
$R^2$ is chlorine, $R^4$ is chlorine, $R^5$ is methyl, $R^6$ is difluoromethoxy, $R^7$ is bromine and $R^{3a}$ is ethyl.

In other preferred compositions of the embodiment 11 the PPO inhibitor herbicide is select from the group of triazindione herbicides of the formulae C.2.6, in particular the compound of the formula C.2.6, wherein the variable Y is S, $R^{23}$ is fluorine, $R^{24}$ is propargyl, $R^{25}$ is methyl and $R^{26}$ is methyl.

In other preferred compositions of the embodiment 11 the PPO inhibitor herbicide is select from the group of dicarboxamide herbicides of the formulae C.2.7, in particular the compound of the formula C.2.7a.

In the embodiment 11 the relative weight ratio of pyroxasulfone and herbicide C.1.1+C.2 is preferably from 500:1 to 1:500 and more preferably from 250:1 to 1:250. The relative weight ratio of herbicide A to herbicide B+herbicide C.1.1+herbicide C.2 is preferably in the range from 1000:1 to 1:50 and more preferably from 500:1 to 1:30.

In further preferred compositions of the invention, the herbicide C comprises or in particular is a mixture of an auxin herbicide or a salt thereof (herbicide C.3) and at least one protoporphyrinogen oxidase inhibitor, in particular selected from the groups C.2.1, C.2.2, C.2.5, C.2.6 and C.2.7 (embodiment 12).

In the preferred compositions of the embodiment 12 the auxin herbicide is a benzoic acid herbicide of the group C.3.1 such as dicamba or a salt thereof, or of the group C.3.2 such as quinmerac or a salt thereof.

In the preferred compositions of the embodiment 12 the PPO inhibitor herbicide is select from the group of pyrimidinedione herbicides, in particular saflufenacil or a salt thereof.

In other preferred compositions of the embodiment 12 the PPO inhibitor herbicide is select from the group of pyrimidinedione herbicides of the formulae C.2.1b or C.2.1c, in particular the compound of the formula C.2.1b, wherein $R^2$ is fluorine, $R^4$ is chlorine, $R^5$ is methyl and $R^{3a}$ is cyclopropylmethyl, and the compound of the formula C.2.1c, wherein $R^2$ is fluorine, $R^4$ is chlorine, $R^5$ is methyl and $R^{3a}$ is trifluoromethyl In other preferred compositions of the embodiment 12 the PPO inhibitor herbicide is select from the group of pyrazole herbicides of the formulae C.2.5, in particular compounds of the formula C2.5a, and more preferably the compounds of the formula C.2.5a, wherein $R^2$ is fluorine, $R^4$ is chlorine, $R^5$ is methyl, $R^6$ is difluoromethoxy, $R^7$ is chlorine and $R^{3a}$ is ethyl, $R^2$ is chlorine, $R^4$ is chlorine, $R^5$ is methyl, $R^6$ is difluoromethoxy, $R^7$ is chlorine and $R^{3a}$ is ethyl, $R^2$ is fluorine, $R^4$ is chlorine, $R^5$ is methyl, $R^6$ is difluoromethoxy, $R^7$ is bromine and $R^{3a}$ is ethyl, or $R^2$ is chlorine, $R^4$ is chlorine, $R^5$ is methyl, $R^6$ is difluoromethoxy, $R^7$ is bromine and $R^{3a}$ is ethyl.

In other preferred compositions of the embodiment 12 the PPO inhibitor herbicide is select from the group of triazindione herbicides of the formulae C.2.6, in particular the compound of the formula C.2.6, wherein the variable Y is S, $R^{23}$ is fluorine, $R^{24}$ is propargyl, $R^{25}$ is methyl and $R^{26}$ is methyl.

In other preferred compositions of the embodiment 12 the PPO inhibitor herbicide is select from the group of dicarboxamide herbicides of the formulae C.2.7, in particular the compound of the formula C.2.7a.

In the embodiment 12 the relative weight ratio of pyroxasulfone and herbicide C.1.1+C.2 is preferably from 500:1 to 1:500 and more preferably from 250:1 to 1:250. The relative weight ratio of herbicide A to herbicide B+herbicide C.1.1+ herbicide C.2 is preferably in the range from 1000:1 to 1:50 and more preferably from 500:1 to 1:30.

In further preferred compositions of the invention, the herbicide C comprises or in particular is a mixture of an PPO inhibitor, in particular of the groups C.2.1 and/or C.2.2 and/or C.2.5 and/or C.2.5 and/or C.2.7 and at least one PSII inhibitor, in particular selected from the groups C.6.1, C.6.2, C.6.3 and C.6.8 and optionally one or more auxin herbicides C.3, in particular a herbicide of the groups C.3.1, C.3.2 and/or C.3.4, (embodiment 13).

In the preferred compositions of the embodiment 13 the PPO inhibitor herbicide is select from the group of pyrimidinedione herbicides, in particular saflufenacil or a salt thereof.

In other preferred compositions of the embodiment 13 the PPO inhibitor herbicide is select from the group of pyrimidinedione herbicides of the formulae C.2.1b or C.2.1c, in particular the compound of the formula C.2.1b, wherein $R^2$ is fluorine, $R^4$ is chlorine, $R^5$ is methyl and $R^{3a}$ is cyclopropylmethyl, and the compound of the formula C.2.1c, wherein $R^2$ is fluorine, $R^4$ is chlorine, $R^5$ is methyl and $R^{3a}$ is trifluoromethyl In other preferred compositions of the embodiment 13 the PPO inhibitor herbicide is select from the group of pyrazole herbicides of the formulae C.2.5, in particular compounds of the formula C2.5a, and more preferably the compounds of the formula C.2.5a, wherein $R^2$ is fluorine, $R^4$ is chlorine, $R^5$ is methyl, $R^6$ is difluoromethoxy, $R^7$ is chlorine and $R^{3a}$ is ethyl, $R^2$ is chlorine, $R^4$ is chlorine, $R^5$ is methyl, $R^6$ is difluoromethoxy, $R^7$ is chlorine and $R^{3a}$ is ethyl, $R^2$ is fluorine, $R^4$ is chlorine, $R^5$ is methyl, $R^6$ is difluoromethoxy, $R^7$ is bromine and $R^{3a}$ is ethyl, or $R^2$ is chlorine, $R^4$ is chlorine, $R^5$ is methyl, $R^6$ is difluoromethoxy, $R^7$ is bromine and $R^{3a}$ is ethyl.

In other preferred compositions of the embodiment 13 the PPO inhibitor herbicide is select from the group of triazindione herbicides of the formulae C.2.6, in particular the compound of the formula C.2.6, wherein the variable Y is S, $R^{23}$ is fluorine, $R^{24}$ is propargyl, $R^{25}$ is methyl and $R^{26}$ is methyl.

In other preferred compositions of the embodiment 13 the PPO inhibitor herbicide is select from the group of dicarboxamide herbicides of the formulae C.2.7, in particular the compound of the formula C.2.7a.

In the preferred compositions of the embodiment 13 the PSII-inhibitor is preferably selected from atrazine, terbuthylazin, ametryn, hexazinone, metribuzin, diuron, isoproturon.

In the preferred compositions of the embodiment 13 the optional auxin herbicide C.3 is at least one benzoic acid herbicide of the group C.3.1, such as dicamba or a salt thereof, or quinolinecarboxylic acid herbicide of the group C.3.2 such as quinmerac or a salt thereof.

In particular preferred compositions of this embodiment 13, the herbicide C comprises or in particular is a mixture of saflufenacil, at least one PSII inhibitor selected from atrazine, metribuzine and terbuthylazine, and an auxin herbicide, in particular a benzoic acid herbicide such as dicamba.

In the embodiment 13 the relative weight ratio of pyroxasulfone and herbicide C.2+C.6 or C.2+C.6+C.3 is preferably from 500:1 to 1:500 and more preferably from 250:1 to 1:250. The relative weight ratio of herbicide A to herbicide B+herbicide C.2+herbicide C.6 or herbicide C.2+herbicide C.3+herbicide C.6 is preferably in the range from 1000:1 to 1:50 and more preferably from 500:1 to 1:30.

In further preferred compositions of the invention, the herbicide C comprises or in particular is a mixture of an PDS inhibitor, in particular an pyridinecarboxamide herbicide, and at least one herbicide of the group of microtubulin inhibitors (embodiment 14).

In the preferred compositions of the embodiment 14 the MTA inhibitor herbicide (herbicide C.7) is select from the group of dinitroanilines, in particular pendimethalin.

In the preferred compositions of the embodiment 14 the PDS herbicide is selected from the group of pyridinecarboxamide herbicides, in particular from flufenican, diflufenican and picolinafen, more preferably picolinafen.

In the embodiment 14 the relative weight ratio of pyroxasulfone and herbicide C.5+C.7 is preferably from 200:1 to 1:200 and more preferably from 100:1 to 1:100. The relative weight ratio of herbicide A to herbicide B+herbicide C.7+ herbicide C.5 is preferably in the range from 1000:1 to 1:50 and more preferably from 500:1 to 1:30.

In further preferred compositions of the invention, the herbicide C comprises or in particular is a mixture of HPPD-inhibitor herbicide and at least one protoporphyrinogen oxidase inhibitor, in particular selected from the groups C.2.1 and C.2.2, C.2.5, C.2.6 and C.2.7 (embodiment 15).

In the preferred compositions of the embodiment 15 the HPPD-inhibitor herbicide is selected from the group of topramezone, tembotrione, isoxaflutole, mesotrione and sulcotrione and the salts thereof.

In the preferred compositions of the embodiment 15 the PPO inhibitor herbicide is select from the group of pyrimidinedione herbicides, in particular saflufenacil or a salt thereof.

In other preferred compositions of the embodiment 15 the PPO inhibitor herbicide is select from the group of pyrimidinedione herbicides of the formulae C.2.1b or C.2.1c, in particular the compound of the formula C.2.1b, wherein $R^2$ is fluorine, $R^4$ is chlorine, $R^5$ is methyl and $R^{3a}$ is cyclopropylmethyl, and the compound of the formula C.2.1c, wherein $R^2$ is fluorine, $R^4$ is chlorine, $R^5$ is methyl and $R^{3a}$ is trifluoromethyl In other preferred compositions of the embodiment 15 the PPO inhibitor herbicide is select from the group of pyrazole herbicides of the formulae C.2.5, in particular compounds of the formula C2.5a, and more preferably the compounds of the formula C.2.5a, wherein $R^2$ is fluorine, $R^4$ is chlorine, $R^5$ is methyl, $R^6$ is difluoromethoxy, $R^7$ is chlorine and $R^{3a}$ is ethyl, $R^2$ is chlorine, $R^4$ is chlorine, $R^5$ is methyl, $R^6$ is difluoromethoxy, $R^7$ is chlorine and $R^{3a}$ is ethyl, $R^2$ is fluorine, $R^4$ is chlorine, $R^5$ is methyl, $R^6$ is difluoromethoxy, $R^7$ is bromine and $R^{3a}$ is ethyl, or $R^2$ is chlorine, $R^4$ is chlorine, $R^5$ is methyl, $R^6$ is difluoromethoxy, $R^7$ is bromine and $R^{3a}$ is ethyl.

In other preferred compositions of the embodiment 15 the PPO inhibitor herbicide is select from the group of triazindione herbicides of the formulae C.2.6, in particular the compound of the formula C.2.6, wherein the variable Y is S, $R^{23}$ is fluorine, $R^{24}$ is propargyl, $R^{25}$ is methyl and $R^{26}$ is methyl.

In other preferred compositions of the embodiment 15 the PPO inhibitor herbicide is select from the group of dicarboxamide herbicides of the formulae C.2.7, in particular the compound of the formula C.2.7a.

In the embodiment 15 the relative weight ratio of pyroxasulfone and herbicide C.4+C.2 is preferably from 500:1 to 1:500 and more preferably from 250:1 to 1:250. The relative weight ratio of herbicide A to herbicide B+herbicide C.1.1+herbicide C.2 is preferably in the range from 1000:1 to 1:50 and more preferably from 500:1 to 1:30.

In further preferred compositions of the invention, the herbicide C comprises or in particular is a mixture of microtubulin-inhibitor herbicide and at least one protoporphyrinogen oxidase inhibitor, in particular selected from the groups C.2.1 and C.2.2, C.2.5, C.2.6 and C.2.7 (embodiment 16).

In the preferred compositions of the embodiment 16 the microtubulin-inhibitor herbicide is selected from the group of dinitroaniline herbicides, in particular selected from the group of benfluralin, butralin, dinitramine, ethalfluralin, fluchloralin, isopropalin, methalpropalin, nitralin, oryzalin, pendimethalin, prodiamine, profluralin and trifluralin, more preferably selected from the group of oryzalin, pendimethalin and trifluralin.

In the preferred compositions of the embodiment 16 the PPO inhibitor herbicide is select from the group of pyrimidinedione herbicides, in particular saflufenacil or a salt thereof.

In other preferred compositions of the embodiment 16 the PPO inhibitor herbicide is select from the group of pyrimidinedione herbicides of the formulae C.2.1b or C.2.1c, in particular the compound of the formula C.2.1b, wherein $R^2$ is fluorine, $R^4$ is chlorine, $R^5$ is methyl and $R^{3a}$ is cyclopropylmethyl, and the compound of the formula C.2.1c, wherein $R^2$ is fluorine, $R^4$ is chlorine, $R^5$ is methyl and $R^{3a}$ is trifluoromethyl.

In other preferred compositions of the embodiment 16 the PPO inhibitor herbicide is select from the group of pyrazole herbicides of the formulae C.2.5, in particular compounds of the formula C2.5a, and more preferably the compounds of the formula C.2.5a, wherein $R^2$ is fluorine, $R^4$ is chlorine, $R^5$ is methyl, $R^6$ is difluoromethoxy, $R^7$ is chlorine and $R^{3a}$ is ethyl, $R^2$ is chlorine, $R^4$ is chlorine, $R^5$ is methyl, $R^6$ is difluoromethoxy, $R^7$ is chlorine and $R^{3a}$ is ethyl, $R^2$ is fluorine, $R^4$ is chlorine, $R^5$ is methyl, $R^6$ is difluoromethoxy, $R^7$ is bromine and $R^{3a}$ is ethyl, or $R^2$ is chlorine, $R^4$ is chlorine, $R^5$ is methyl, $R^6$ is difluoromethoxy, $R^7$ is bromine and $R^{3a}$ is ethyl.

In other preferred compositions of the embodiment 16 the PPO inhibitor herbicide is select from the group of triazindione herbicides of the formulae C.2.6, in particular the compound of the formula C.2.6, wherein the variable Y is S, $R^{23}$ is fluorine, $R^{24}$ is propargyl, $R^{25}$ is methyl and $R^{26}$ is methyl.

In other preferred compositions of the embodiment 16 the PPO inhibitor herbicide is select from the group of dicarboxamide herbicides of the formulae C.2.7, in particular the compound of the formula C.2.7a.

In the embodiment 16 the relative weight ratio of pyroxasulfone and herbicide C.7+C.2 is preferably from 500:1 to 1:500 and more preferably from 250:1 to 1:250. The relative weight ratio of herbicide A to herbicide B+herbicide C.1.1+herbicide C.2 is preferably in the range from 1000:1 to 1:50 and more preferably from 500:1 to 1:30.

In further preferred compositions of the invention, the herbicide C comprises or in particular is a mixture of VLCFA inhibitor herbicide and at least one protoporphyrinogen oxidase inhibitor, in particular selected from the groups C.2.1 and C.2.2, C.2.5, C.2.6 and C.2.7 (embodiment 16).

In the preferred compositions of the embodiment 17 are selected from the group consisting of chloroacetamide herbicides (embodiment 17.1), in particular acetochlor, dimethachlor, dimethenamid, dimethenamid-P, metazachlor, propisochlor, pethoxamide, metolachlor, and metolachlor-S and oxyacetamide herbicides (embodiment 17.2), in particular flufenacet.

In the compositions of the embodiment 17 (and likewise in embodiments 17.1 and 17.2) the relative weight ratio of pyroxasulfone to herbicide C.8 is preferably in the range from 1:250 to 250:1, in particular in the range of 1:200 to 200:1 and more preferably from 150:1 to 1:150. The relative weight ratio of herbicide A to herbicide B+herbicide C.8 is preferably in the range from 1500:1 to 1:20 and more preferably from 1000:1 to 1:10.

In particular preferred compositions of this embodiment 17.1, the herbicide C comprises or in particular is acetochlor.

In other particular preferred compositions of this embodiment 17.1, the herbicide C comprises or in particular is dimethachlor.

In further particular preferred compositions of this embodiment 17.1, the herbicide C comprises or in particular is dimethenamid.

In further particular preferred compositions of this embodiment 17.1, the herbicide C comprises or in particular is dimethenamid-P.

In further particular preferred compositions of this embodiment 17.1, the herbicide C comprises or in particular is metazachlor.

In further particular preferred compositions of this embodiment 17.1, the herbicide C comprises or in particular is propisochlor.

In further particular preferred compositions of this embodiment 17.2, the herbicide C comprises or in particular is flufenacet.

In the preferred compositions of the embodiment 17 the PPO inhibitor herbicide is select from the group of pyrimidinedione herbicides, in particular saflufenacil or a salt thereof.

In other preferred compositions of the embodiment 17 the PPO inhibitor herbicide is select from the group of pyrimidinedione herbicides of the formulae C.2.1b or C.2.1c, in particular the compound of the formula C.2.1b, wherein $R^2$ is fluorine, $R^4$ is chlorine, $R^5$ is methyl and $R^{3a}$ is cyclopropylmethyl, and the compound of the formula C.2.1c, wherein $R^2$ is fluorine, $R^4$ is chlorine, $R^5$ is methyl and $R^{3a}$ is trifluoromethyl.

In other preferred compositions of the embodiment 17 the PPO inhibitor herbicide is select from the group of pyrazole herbicides of the formulae C.2.5, in particular compounds of the formula C2.5a, and more preferably the compounds of the formula C.2.5a, wherein $R^2$ is fluorine, $R^4$ is chlorine, $R^5$ is methyl, $R^6$ is difluoromethoxy, $R^7$ is chlorine and $R^{3a}$ is ethyl, $R^2$ is chlorine, $R^4$ is chlorine, $R^5$ is methyl, $R^6$ is difluoromethoxy, $R^7$ is chlorine and $R^{3a}$ is ethyl, $R^2$ is fluorine, $R^4$ is chlorine, $R^5$ is methyl, $R^6$ is difluoromethoxy, $R^7$ is bromine and $R^{3a}$ is ethyl, or $R^2$ is chlorine, $R^4$ is chlorine, $R^5$ is methyl, $R^6$ is difluoromethoxy, $R^7$ is bromine and $R^{3a}$ is ethyl.

In other preferred compositions of the embodiment 17 the PPO inhibitor herbicide is select from the group of triazindione herbicides of the formulae C.2.6, in particular the compound of the formula C.2.6, wherein the variable Y is S, $R^{23}$ is fluorine, $R^{24}$ is propargyl, $R^{25}$ is methyl and $R^{26}$ is methyl.

In other preferred compositions of the embodiment 17 the PPO inhibitor herbicide is select from the group of dicarboxamide herbicides of the formulae C.2.7, in particular the compound of the formula C.2.7a.

In the embodiment 17 the relative weight ratio of pyroxasulfone and herbicide C.7+C.2 is preferably from 500:1 to 1:500 and more preferably from 250:1 to 1:250. The relative weight ratio of herbicide A to herbicide B+herbicide C.1.1+ herbicide C.2 is preferably in the range from 1000:1 to 1:50 and more preferably from 500:1 to 1:30.

In further preferred compositions of this embodiment 17, the composition additionally contains at least one herbicides of the group C.3, in particular of the group C.3.1 such as dicamba or a salt thereof, or of the group C.3.2 such as quinmerac or a salt thereof (embodiment 17.3) and/or clomazone (embodiment 17.4). In these preferred compositions of the embodiments 17.3 and 17.4 the VLCFA-inhibitor is preferably selected from chloroacetamide herbicides, in particular selected from acetochlor, dimethachlor, dimethenamid, dimethenamid-P, metazachlor, metolachlor, S-metolachlor, pethoxamide and propisochlor. In these preferred compositions the oxyacetamide herbicide is preferably flufenacet.

In further particular preferred compositions of this embodiment 17.3, the herbicide C comprises or in particular is a mixture of PPO inhibitor, quinmerac or a salt thereof and metazachlor.

In further particular preferred compositions of this embodiment 17.3, the herbicide C comprises or in particular is a mixture of PPO inhibitor, dicamba or a salt thereof and metazachlor.

In further particular preferred compositions of this embodiment 17.3, the herbicide C comprises or in particular is a mixture of PPO inhibitor, dicamba or a salt thereof and flufenacet.

In further particular preferred compositions of this embodiment 17.3, the herbicide C comprises or in particular is a mixture of PPO inhibitor, dicamba or a salt thereof and dimethenamid-P, optionally comprising a PSII inhibitor herbicide such as atrazine or metribuzin.

In further particular preferred compositions of this embodiment 17.4, the herbicide C comprises or in particular is a mixture of PPO inhibitor, clomazone and metazachlor.

In further particular preferred compositions of this embodiment 8.4, the herbicide C comprises or in particular is a mixture of PPO inhibitor, clomazone and dimethenamid-P.

Examples of suitable compositions are given in the following table 1:

| No. | Herbicide A* | Herbicide B | Herbicide C* | B:C w/w | A:(B + C) w/w |
|---|---|---|---|---|---|
| 1 | glyphosate | pyroxasulfone | — | — | 2000:1-1:10 |
| 2 | glufosinate | pyroxasulfone | — | — | 2000:1-1:10 |
| 3 | glyphosate | pyroxasulfone | imazamox | 500:1-1:500 | 1500:1-1:20 |
| 4 | glufosinate | pyroxasulfone | imazamox | 500:1-1:500 | 1500:1-1:20 |
| 5 | glyphosate | pyroxasulfone | imazapyr | 500:1-1:500 | 1500:1-1:20 |
| 6 | glufosinate | pyroxasulfone | imazapyr | 500:1-1:500 | 1500:1-1:20 |
| 7 | glyphosate | pyroxasulfone | imazapic | 500:1-1:500 | 1500:1-1:20 |
| 8 | glufosinate | pyroxasulfone | imazapic | 500:1-1:500 | 1500:1-1:20 |
| 9 | glyphosate | pyroxasulfone | imazethapyr | 500:1-1:500 | 1500:1-1:20 |
| 10 | glufosinate | pyroxasulfone | imazethapyr | 500:1-1:500 | 1500:1-1:20 |
| 11 | glyphosate | pyroxasulfone | imazamox + imazethapyr | 500:1-1:500 | 1500:1-1:20 |
| 12 | glufosinate | pyroxasulfone | imazamox + imazethapyr | 500:1-1:500 | 1500:1-1:20 |
| 13 | glyphosate | pyroxasulfone | imazamox + imazapyr | 500:1-1:500 | 1500:1-1:20 |
| 14 | glufosinate | pyroxasulfone | imazamox + imazapyr | 500:1-1:500 | 1500:1-1:20 |
| 15 | glyphosate | pyroxasulfone | imazapic + imazethapyr | 500:1-1:500 | 1500:1-1:20 |
| 16 | glufosinate | pyroxasulfone | imazapic + imazethapyr | 500:1-1:500 | 1500:1-1:20 |
| 17 | glyphosate | pyroxasulfone | imazapic + imazapyr | 500:1-1:500 | 1500:1-1:20 |
| 18 | glufosinate | pyroxasulfone | imazapic + imazapyr | 500:1-1:500 | 1500:1-1:20 |
| 19 | glyphosate | pyroxasulfone | saflufenacil | 100:1-1:100 | 1000:1-1:10 |
| 20 | glufosinate | pyroxasulfone | saflufenacil | 100:1-1:100 | 1000:1-1:10 |
| 21 | glyphosate | pyroxasulfone | butafenacil | 100:1-1:100 | 1000:1-1:10 |
| 22 | glufosinate | pyroxasulfone | butafenacil | 100:1-1:100 | 1000:1-1:10 |
| 23 | glyphosate | pyroxasulfone | flumioxazin | 100:1-1:100 | 1000:1-1:10 |
| 24 | glufosinate | pyroxasulfone | flumioxazin | 100:1-1:100 | 1000:1-1:10 |
| 25 | glyphosate | pyroxasulfone | flumiclorac | 100:1-1:100 | 1000:1-1:10 |
| 26 | glufosinate | pyroxasulfone | flumiclorac | 100:1-1:100 | 1000:1-1:10 |

-continued

| No. | Herbicide A* | Herbicide B | Herbicide C* | B:C w/w | A:(B + C) w/w |
|---|---|---|---|---|---|
| 27 | glyphosate | pyroxasulfone | flumipropyn | 100:1-1:100 | 1000:1-1:10 |
| 28 | glufosinate | pyroxasulfone | flumipropyn | 100:1-1:100 | 1000:1-1:10 |
| 29 | glyphosate | pyroxasulfone | dicamba | 250:1-1:250 | 1000:1-1:10 |
| 30 | glufosinate | pyroxasulfone | dicamba | 250:1-1:250 | 1000:1-1:10 |
| 31 | glyphosate | pyroxasulfone | 2,4-D | 500:1-1:500 | 1000:1-1:10 |
| 32 | glufosinate | pyroxasulfone | 2,4-D | 500:1-1:500 | 1000:1-1:10 |
| 33 | glyphosate | pyroxasulfone | topramezone | 100:1-1:100 | 1500:1-1:20 |
| 34 | glufosinate | pyroxasulfone | topramezone | 100:1-1:100 | 1500:1-1:20 |
| 35 | glyphosate | pyroxasulfone | isoxaflutole | 100:1-1:100 | 1500:1-1:20 |
| 36 | glufosinate | pyroxasulfone | isoxaflutole | 100:1-1:100 | 1500:1-1:20 |
| 37 | glyphosate | pyroxasulfone | mesotrione | 100:1-1:100 | 1500:1-1:20 |
| 38 | glufosinate | pyroxasulfone | mesotrione | 100:1-1:100 | 1500:1-1:20 |
| 39 | glyphosate | pyroxasulfone | sulcotrione | 100:1-1:100 | 1500:1-1:20 |
| 40 | glufosinate | pyroxasulfone | sulcotrione | 100:1-1:100 | 1500:1-1:20 |
| 41 | glyphosate | pyroxasulfone | flufenican | 100:1-1:100 | 1500:1-1:20 |
| 42 | glufosinate | pyroxasulfone | flufenican | 100:1-1:100 | 1500:1-1:20 |
| 43 | glyphosate | pyroxasulfone | diflufenican | 100:1-1:100 | 1500:1-1:20 |
| 44 | glufosinate | pyroxasulfone | diflufenican | 100:1-1:100 | 1500:1-1:20 |
| 45 | glyphosate | pyroxasulfone | picolinafen | 100:1-1:100 | 1500:1-1:20 |
| 46 | glufosinate | pyroxasulfone | picolinafen | 100:1-1:100 | 1500:1-1:20 |
| 47 | glyphosate | pyroxasulfone | atrazine | 500:1-1:500 | 1500:1-1:20 |
| 48 | glufosinate | pyroxasulfone | atrazine | 500:1-1:500 | 1500:1-1:20 |
| 49 | glyphosate | pyroxasulfone | metribuzin | 500:1-1:500 | 1500:1-1:20 |
| 50 | glufosinate | pyroxasulfone | metribuzin | 500:1-1:500 | 1500:1-1:20 |
| 51 | glyphosate | pyroxasulfone | terbuthylazine | 500:1-1:500 | 1500:1-1:20 |
| 52 | glufosinate | pyroxasulfone | terbuthylazine | 500:1-1:500 | 1500:1-1:20 |
| 53 | glyphosate | pyroxasulfone | ametryn | 500:1-1:500 | 1500:1-1:20 |
| 54 | glufosinate | pyroxasulfone | ametryn | 500:1-1:500 | 1500:1-1:20 |
| 55 | glyphosate | pyroxasulfone | hexazinone | 500:1-1:500 | 1500:1-1:20 |
| 56 | glufosinate | pyroxasulfone | hexazinone | 500:1-1:500 | 1500:1-1:20 |
| 57 | glyphosate | pyroxasulfone | diuron | 500:1-1:500 | 1500:1-1:20 |
| 58 | glufosinate | pyroxasulfone | diuron | 500:1-1:500 | 1500:1-1:20 |
| 59 | glyphosate | pyroxasulfone | isoproturon | 500:1-1:500 | 1500:1-1:20 |
| 60 | glufosinate | pyroxasulfone | isoproturon | 500:1-1:500 | 1500:1-1:20 |
| 61 | glyphosate | pyroxasulfone | atrazine + ametryn | 500:1-1:500 | 1500:1-1:20 |
| 62 | glufosinate | pyroxasulfone | atrazine + ametryn | 500:1-1:500 | 1500:1-1:20 |
| 63 | glyphosate | pyroxasulfone | atrazine + metribuzin | 500:1-1:500 | 1500:1-1:20 |
| 64 | glufosinate | pyroxasulfone | atrazine + metribuzin | 500:1-1:500 | 1500:1-1:20 |
| 65 | glyphosate | pyroxasulfone | pendimethalin | 100:1-1:500 | 1500:1-1:100 |
| 66 | glufosinate | pyroxasulfone | pendimethalin | 100:1-1:500 | 1500:1-1:100 |
| 67 | glyphosate | pyroxasulfone | oryzalin | 100:1-1:500 | 1500:1-1:100 |
| 68 | glufosinate | pyroxasulfone | oryzalin | 100:1-1:500 | 1500:1-1:100 |
| 69 | glyphosate | pyroxasulfone | acetochlor | 250:1-1:250 | 1500:1-1:20 |
| 70 | glufosinate | pyroxasulfone | acetochlor | 250:1-1:250 | 1500:1-1:20 |
| 71 | glyphosate | pyroxasulfone | dimethenamid | 250:1-1:250 | 1500:1-1:20 |
| 72 | glufosinate | pyroxasulfone | dimethenamid | 250:1-1:250 | 1500:1-1:20 |
| 73 | glyphosate | pyroxasulfone | dimethenamid-P | 250:1-1:250 | 1500:1-1:20 |
| 74 | glufosinate | pyroxasulfone | dimethenamid-P | 250:1-1:250 | 1500:1-1:20 |
| 75 | glyphosate | pyroxasulfone | dimethachlor | 250:1-1:250 | 1500:1-1:20 |
| 76 | glufosinate | pyroxasulfone | dimethachlor | 250:1-1:250 | 1500:1-1:20 |
| 77 | glyphosate | pyroxasulfone | metazachlor | 250:1-1:250 | 1500:1-1:20 |
| 78 | glufosinate | pyroxasulfone | metazachlor | 250:1-1:250 | 1500:1-1:20 |
| 79 | glyphosate | pyroxasulfone | propisochlor | 250:1-1:250 | 1500:1-1:20 |
| 80 | glufosinate | pyroxasulfone | propisochlor | 250:1-1:250 | 1500:1-1:20 |
| 81 | glyphosate | pyroxasulfone | flufenacet | 250:1-1:250 | 1500:1-1:20 |
| 82 | glufosinate | pyroxasulfone | flufenacet | 250:1-1:250 | 1500:1-1:20 |
| 83 | glyphosate | pyroxasulfone | quinmerac + metazachlor | 500:1-1:500 | 1000:1-1:50 |
| 84 | glufosinate | pyroxasulfone | quinmerac + metazachlor | 500:1-1:500 | 1000:1-1:50 |
| 85 | glyphosate | pyroxasulfone | quinmerac + flufenacet | 500:1-1:500 | 1000:1-1:50 |
| 86 | glufosinate | pyroxasulfone | quinmerac + flufenacet | 500:1-1:500 | 1000:1-1:50 |
| 87 | glyphosate | pyroxasulfone | dicamba + flufenacet | 500:1-1:500 | 1000:1-1:50 |
| 88 | glufosinate | pyroxasulfone | dicamba + flufenacet | 500:1-1:500 | 1000:1-1:50 |
| 89 | glyphosate | pyroxasulfone | metribuzin + flufenacet | 500:1-1:500 | 1000:1-1:50 |
| 90 | glufosinate | pyroxasulfone | metribuzin + flufenacet | 500:1-1:500 | 1000:1-1:50 |
| 91 | glyphosate | pyroxasulfone | atrazine + flufenacet | 500:1-1:500 | 1000:1-1:50 |
| 92 | glufosinate | pyroxasulfone | atrazine + flufenacet | 500:1-1:500 | 1000:1-1:50 |

-continued

| No. | Herbicide A* | Herbicide B | Herbicide C* | B:C w/w | A:(B + C) w/w |
|---|---|---|---|---|---|
| 93 | glyphosate | pyroxasulfone | metribuzin + metazachlor | 500:1-1:500 | 1000:1-1:50 |
| 94 | glufosinate | pyroxasulfone | metribuzin + metazachlor | 500:1-1:500 | 1000:1-1:50 |
| 95 | glyphosate | pyroxasulfone | atrazine + metazachlor | 500:1-1:500 | 1000:1-1:50 |
| 96 | glufosinate | pyroxasulfone | atrazine + metazachlor | 500:1-1:500 | 1000:1-1:50 |
| 97 | glyphosate | pyroxasulfone | metribuzin + alachlor | 500:1-1:500 | 1000:1-1:50 |
| 98 | glufosinate | pyroxasulfone | metribuzin + alachlor | 500:1-1:500 | 1000:1-1:50 |
| 99 | glyphosate | pyroxasulfone | atrazine + alachlor | 500:1-1:500 | 1000:1-1:50 |
| 100 | glufosinate | pyroxasulfone | atrazine + alachlor | 500:1-1:500 | 1000:1-1:50 |
| 101 | glyphosate | pyroxasulfone | metribuzin + atrazine + flufenacet | 500:1-1:500 | 1000:1-1:50 |
| 102 | glufosinate | pyroxasulfone | metribuzin + atrazine + flufenacet | 500:1-1:500 | 1000:1-1:50 |
| 103 | glyphosate | pyroxasulfone | metribuzin + flufenacet + dicamba | 500:1-1:500 | 1000:1-1:50 |
| 104 | glufosinate | pyroxasulfone | metribuzin + flufenacet + dicamba | 500:1-1:500 | 1000:1-1:50 |
| 105 | glyphosate | pyroxasulfone | atrazine + flufenacet + dicamba | 500:1-1:500 | 1000:1-1:50 |
| 106 | glufosinate | pyroxasulfone | atrazine + flufenacet + dicamba | 500:1-1:500 | 1000:1-1:50 |
| 107 | glyphosate | pyroxasulfone | metribuzin + atrazine + metazachlor | 500:1-1:500 | 1000:1-1:50 |
| 108 | glufosinate | pyroxasulfone | metribuzin + atrazine + metazachlor | 500:1-1:500 | 1000:1-1:50 |
| 109 | glyphosate | pyroxasulfone | metribuzin + metazachlor + dicamba | 500:1-1:500 | 1000:1-1:50 |
| 110 | glufosinate | pyroxasulfone | metribuzin + metazachlor + dicamba | 500:1-1:500 | 1000:1-1:50 |
| 111 | glyphosate | pyroxasulfone | atrazine + metazachlor + dicamba | 500:1-1:500 | 1000:1-1:50 |
| 112 | glufosinate | pyroxasulfone | atrazine + metazachlor + dicamba | 500:1-1:500 | 1000:1-1:50 |
| 113 | glyphosate | pyroxasulfone | metribuzin + alachlor + dicamba | 500:1-1:500 | 1000:1-1:50 |
| 114 | glufosinate | pyroxasulfone | metribuzin + alachlor + dicamba | 500:1-1:500 | 1000:1-1:50 |
| 115 | glyphosate | pyroxasulfone | atrazine + alachlor + dicamba | 500:1-1:500 | 1000:1-1:50 |
| 116 | glufosinate | pyroxasulfone | atrazine + alachlor + dicamba | 500:1-1:500 | 1000:1-1:50 |
| 117 | glyphosate | pyroxasulfone | metribuzin + atrazine + flufenacet + dicamba | 500:1-1:500 | 1000:1-1:50 |
| 118 | glufosinate | pyroxasulfone | metribuzin + atrazine + flufenacet + dicamba | 500:1-1:500 | 1000:1-1:50 |
| 119 | glyphosate | pyroxasulfone | flufenacet + metribuzin + dicamba | 500:1-1:500 | 1000:1-1:50 |

-continued

| No. | Herbicide A* | Herbicide B | Herbicide C* | B:C w/w | A:(B + C) w/w |
|---|---|---|---|---|---|
| 120 | glufosinate | pyroxasulfone | flufenacet + metribuzin + dicamba | 500:1-1:500 | 1000:1-1:50 |
| 121 | glyphosate | pyroxasulfone | dimethenamid + dicamba | 500:1-1:500 | 1000:1-1:50 |
| 122 | glufosinate | pyroxasulfone | dimethenamid + dicamba | 500:1-1:500 | 1000:1-1:50 |
| 123 | glyphosate | pyroxasulfone | dimethenamid + atrazine | 500:1-1:500 | 1000:1-1:50 |
| 124 | glufosinate | pyroxasulfone | dimethenamid + atrazine | 500:1-1:500 | 1000:1-1:50 |
| 125 | glyphosate | pyroxasulfone | dimethenamid + dicamba + atrazine | 500:1-1:500 | 1000:1-1:50 |
| 126 | glufosinate | pyroxasulfone | dimethenamid + dicamba + atrazine | 500:1-1:500 | 1000:1-1:50 |
| 127 | glyphosate | pyroxasulfone | imazamox + atrazine | 500:1-1:500 | 1000:1-1:50 |
| 128 | glufosinate | pyroxasulfone | imazamox + atrazine | 500:1-1:500 | 1000:1-1:50 |
| 129 | glyphosate | pyroxasulfone | imazapyr + atrazine | 500:1-1:500 | 1000:1-1:50 |
| 130 | glufosinate | pyroxasulfone | imazapyr + atrazine | 500:1-1:500 | 1000:1-1:50 |
| 131 | glyphosate | pyroxasulfone | imazapic + atrazine | 500:1-1:500 | 1000:1-1:50 |
| 132 | glufosinate | pyroxasulfone | imazapic + atrazine | 500:1-1:500 | 1000:1-1:50 |
| 133 | glyphosate | pyroxasulfone | imazethapyr + atrazine | 500:1-1:500 | 1000:1-1:50 |
| 134 | glufosinate | pyroxasulfone | imazethapyr + atrazine | 500:1-1:500 | 1000:1-1:50 |
| 135 | glyphosate | pyroxasulfone | imazamox + imazethapyr + atrazine | 500:1-1:500 | 1000:1-1:50 |
| 136 | glufosinate | pyroxasulfone | imazamox + imazethapyr + atrazine | 500:1-1:500 | 1000:1-1:50 |
| 137 | glyphosate | pyroxasulfone | imazamox + imazapyr + atrazine | 500:1-1:500 | 1000:1-1:50 |
| 138 | glufosinate | pyroxasulfone | imazamox + imazapyr + atrazine | 500:1-1:500 | 1000:1-1:50 |
| 139 | glyphosate | pyroxasulfone | imazapic + imazethapyr + atrazine | 500:1-1:500 | 1000:1-1:50 |
| 140 | glufosinate | pyroxasulfone | imazapic + imazethapyr + atrazine | 500:1-1:500 | 1000:1-1:50 |
| 141 | glyphosate | pyroxasulfone | imazapic + imazapyr + atrazine | 500:1-1:500 | 1000:1-1:50 |
| 142 | glufosinate | pyroxasulfone | imazapic + imazapyr + atrazine | 500:1-1:500 | 1000:1-1:50 |
| 143 | glyphosate | pyroxasulfone | imazamox + ametryne | 500:1-1:500 | 1000:1-1:50 |
| 144 | glufosinate | pyroxasulfone | imazamox + ametryne | 500:1-1:500 | 1000:1-1:50 |
| 145 | glyphosate | pyroxasulfone | imazapyr + ametryne | 500:1-1:500 | 1000:1-1:50 |
| 146 | glufosinate | pyroxasulfone | imazapyr + ametryne | 500:1-1:500 | 1000:1-1:50 |
| 147 | glyphosate | pyroxasulfone | imazapic + ametryne | 500:1-1:500 | 1000:1-1:50 |
| 148 | glufosinate | pyroxasulfone | imazapic + ametryne | 500:1-1:500 | 1000:1-1:50 |
| 149 | glyphosate | pyroxasulfone | imazethapyr + ametryne | 500:1-1:500 | 1000:1-1:50 |
| 150 | glufosinate | pyroxasulfone | imazethapyr + ametryne | 500:1-1:500 | 1000:1-1:50 |
| 151 | glyphosate | pyroxasulfone | imazamox + imazethapyr + ametryne | 500:1-1:500 | 1000:1-1:50 |

-continued

| No. | Herbicide A* | Herbicide B | Herbicide C* | B:C w/w | A:(B + C) w/w |
|---|---|---|---|---|---|
| 152 | glufosinate | pyroxasulfone | imazamox + imazethapyr + ametryne | 500:1-1:500 | 1000:1-1:50 |
| 153 | glyphosate | pyroxasulfone | imazamox + imazapyr + ametryne | 500:1-1:500 | 1000:1-1:50 |
| 154 | glufosinate | pyroxasulfone | imazamox + imazapyr + ametryne | 500:1-1:500 | 1000:1-1:50 |
| 155 | glyphosate | pyroxasulfone | imazapic + imazethapyr + ametryne | 500:1-1:500 | 1000:1-1:50 |
| 156 | glufosinate | pyroxasulfone | imazapic + imazethapyr + ametryne | 500:1-1:500 | 1000:1-1:50 |
| 157 | glyphosate | pyroxasulfone | imazapic + imazapyr + ametryne | 500:1-1:500 | 1000:1-1:50 |
| 158 | glufosinate | pyroxasulfone | imazapic + imazapyr + ametryne | 500:1-1:500 | 1000:1-1:50 |
| 159 | glyphosate | pyroxasulfone | imazamox + metribuzin | 500:1-1:500 | 1000:1-1:50 |
| 160 | glufosinate | pyroxasulfone | imazamox + metribuzin | 500:1-1:500 | 1000:1-1:50 |
| 161 | glyphosate | pyroxasulfone | imazapyr + metribuzin | 500:1-1:500 | 1000:1-1:50 |
| 162 | glufosinate | pyroxasulfone | imazapyr + metribuzin | 500:1-1:500 | 1000:1-1:50 |
| 163 | glyphosate | pyroxasulfone | imazapic + metribuzin | 500:1-1:500 | 1000:1-1:50 |
| 164 | glufosinate | pyroxasulfone | imazapic + metribuzin | 500:1-1:500 | 1000:1-1:50 |
| 165 | glyphosate | pyroxasulfone | imazethapyr + metribuzin | 500:1-1:500 | 1000:1-1:50 |
| 166 | glufosinate | pyroxasulfone | imazethapyr + metribuzin | 500:1-1:500 | 1000:1-1:50 |
| 167 | glyphosate | pyroxasulfone | imazamox + iazethapyr + metribuzin | 500:1-1:500 | 1000:1-1:50 |
| 168 | glufosinate | pyroxasulfone | imazamox + imazethapyr + metribuzin | 500:1-1:500 | 1000:1-1:50 |
| 169 | glyphosate | pyroxasulfone | imazamox + imazapyr + metribuzin | 500:1-1:500 | 1000:1-1:50 |
| 170 | glufosinate | pyroxasulfone | imazamox + imazapyr + metribuzin | 500:1-1:500 | 1000:1-1:50 |
| 171 | glyphosate | pyroxasulfone | imazapic + imazethapyr + metribuzin | 500:1-1:500 | 1000:1-1:50 |
| 172 | glufosinate | pyroxasulfone | imazapic + imazethapyr + metribuzin | 500:1-1:500 | 1000:1-1:50 |
| 173 | glyphosate | pyroxasulfone | imazapic + imazapyr + metribuzin | 500:1-1:500 | 1000:1-1:50 |
| 174 | glufosinate | pyroxasulfone | imazapic + imazapyr + metribuzin | 500:1-1:500 | 1000:1-1:50 |
| 175 | glyphosate | pyroxasulfone | imazamox + diuron | 500:1-1:500 | 1000:1-1:50 |
| 176 | glufosinate | pyroxasulfone | imazamox + diuron | 500:1-1:500 | 1000:1-1:50 |
| 177 | glyphosate | pyroxasulfone | imazapyr + diuron | 500:1-1:500 | 1000:1-1:50 |
| 178 | glufosinate | pyroxasulfone | imazapyr + diuron | 500:1-1:500 | 1000:1-1:50 |
| 179 | glyphosate | pyroxasulfone | imazapic + diuron | 500:1-1:500 | 1000:1-1:50 |
| 180 | glufosinate | pyroxasulfone | imazapic + diuron | 500:1-1:500 | 1000:1-1:50 |
| 181 | glyphosate | pyroxasulfone | imazethapyr + diuron | 500:1-1:500 | 1000:1-1:50 |
| 182 | glufosinate | pyroxasulfone | imazethapyr + diuron | 500:1-1:500 | 1000:1-1:50 |

-continued

| No. | Herbicide A* | Herbicide B | Herbicide C* | B:C w/w | A:(B + C) w/w |
|---|---|---|---|---|---|
| 183 | glyphosate | pyroxasulfone | imazamox + imazethapyr + diuron | 500:1-1:500 | 1000:1-1:50 |
| 184 | glufosinate | pyroxasulfone | imazamox + imazethapyr + diuron | 500:1-1:500 | 1000:1-1:50 |
| 185 | glyphosate | pyroxasulfone | imazamox + imazapyr + diuron | 500:1-1:500 | 1000:1-1:50 |
| 186 | glufosinate | pyroxasulfone | imazamox + imazapyr + diuron | 500:1-1:500 | 1000:1-1:50 |
| 187 | glyphosate | pyroxasulfone | imazapic + imazethapyr + diuron | 500:1-1:500 | 1000:1-1:50 |
| 188 | glufosinate | pyroxasulfone | imazapic + imazethapyr + diuron | 500:1-1:500 | 1000:1-1:50 |
| 189 | glyphosate | pyroxasulfone | imazapic + imazapyr + diuron | 500:1-1:500 | 1000:1-1:50 |
| 190 | glufosinate | pyroxasulfone | imazapic + imazapyr + diuron | 500:1-1:500 | 1000:1-1:50 |
| 191 | glyphosate | pyroxasulfone | imazamox + terbuthylazine | 500:1-1:500 | 1000:1-1:50 |
| 192 | glufosinate | pyroxasulfone | imazamox + terbuthylazine | 500:1-1:500 | 1000:1-1:50 |
| 193 | glyphosate | pyroxasulfone | imazapyr + terbuthylazine | 500:1-1:500 | 1000:1-1:50 |
| 194 | glufosinate | pyroxasulfone | imazapyr + terbuthylazine | 500:1-1:500 | 1000:1-1:50 |
| 195 | glyphosate | pyroxasulfone | imazapic + terbuthylazine | 500:1-1:500 | 1000:1-1:50 |
| 196 | glufosinate | pyroxasulfone | imazapic + terbuthylazine | 500:1-1:500 | 1000:1-1:50 |
| 197 | glyphosate | pyroxasulfone | imazethapyr + terbuthylazine | 500:1-1:500 | 1000:1-1:50 |
| 198 | glufosinate | pyroxasulfone | imazethapyr + terbuthylazine | 500:1-1:500 | 1000:1-1:50 |
| 199 | glyphosate | pyroxasulfone | imazamox + imazethapyr + terbuthylazine | 500:1-1:500 | 1000:1-1:50 |
| 200 | glufosinate | pyroxasulfone | imazamox + imazethapyr + terbuthylazine | 500:1-1:500 | 1000:1-1:50 |
| 201 | glyphosate | pyroxasulfone | imazamox + imazapyr + terbuthylazine | 500:1-1:500 | 1000:1-1:50 |
| 202 | glufosinate | pyroxasulfone | imazamox + imazapyr + terbuthylazine | 500:1-1:500 | 1000:1-1:50 |
| 203 | glyphosate | pyroxasulfone | imazapic + imazethapyr + terbuthylazine | 500:1-1:500 | 1000:1-1:50 |
| 204 | glufosinate | pyroxasulfone | imazapic + imazethapyr + terbuthylazine | 500:1-1:500 | 1000:1-1:50 |
| 205 | glyphosate | pyroxasulfone | imazapic + imazapyr + terbuthylazine | 500:1-1:500 | 1000:1-1:50 |
| 206 | glufosinate | pyroxasulfone | imazapic + imazapyr + terbuthylazine | 500:1-1:500 | 1000:1-1:50 |
| 207 | glyphosate | pyroxasulfone | isoxaflutole + atrazine | 500:1-1:500 | 1000:1-1:50 |
| 208 | glufosinate | pyroxasulfone | isoxaflutole + atrazine | 500:1-1:500 | 1000:1-1:50 |
| 209 | glyphosate | pyroxasulfone | sulcotrione + atrazine | 500:1-1:500 | 1000:1-1:50 |
| 210 | glufosinate | pyroxasulfone | sulcotrione + atrazine | 500:1-1:500 | 1000:1-1:50 |
| 211 | glyphosate | pyroxasulfone | topramezone + atrazine | 500:1-1:500 | 1000:1-1:50 |
| 212 | glufosinate | pyroxasulfone | topramezone + atrazine | 500:1-1:500 | 1000:1-1:50 |

-continued

| No. | Herbicide A* | Herbicide B | Herbicide C* | B:C w/w | A:(B + C) w/w |
|---|---|---|---|---|---|
| 213 | glyphosate | pyroxasulfone | mesotrione + atrazine | 500:1-1:500 | 1000:1-1:50 |
| 214 | glufosinate | pyroxasulfone | mesotrione + atrazine | 500:1-1:500 | 1000:1-1:50 |
| 215 | glyphosate | pyroxasulfone | tembotrione + atrazine | 500:1-1:500 | 1000:1-1:50 |
| 216 | glufosinate | pyroxasulfone | tembotrione + atrazine | 500:1-1:500 | 1000:1-1:50 |
| 217 | glyphosate | pyroxasulfone | isoxaflutole + metribuzin | 500:1-1:500 | 1000:1-1:50 |
| 218 | glufosinate | pyroxasulfone | isoxaflutole + metribuzin | 500:1-1:500 | 1000:1-1:50 |
| 219 | glyphosate | pyroxasulfone | sulcotrione + metribuzin | 500:1-1:500 | 1000:1-1:50 |
| 220 | glufosinate | pyroxasulfone | sulcotrione + metribuzin | 500:1-1:500 | 1000:1-1:50 |
| 221 | glyphosate | pyroxasulfone | topramezone + metribuzin | 500:1-1:500 | 1000:1-1:50 |
| 222 | glufosinate | pyroxasulfone | topramezone + metribuzin | 500:1-1:500 | 1000:1-1:50 |
| 223 | glyphosate | pyroxasulfone | mesotrione + metribuzin | 500:1-1:500 | 1000:1-1:50 |
| 224 | glufosinate | pyroxasulfone | mesotrione + metribuzin | 500:1-1:500 | 1000:1-1:50 |
| 225 | glyphosate | pyroxasulfone | tembotrione + metribuzin | 500:1-1:500 | 1000:1-1:50 |
| 226 | glufosinate | pyroxasulfone | tembotrione + metribuzin | 500:1-1:500 | 1000:1-1:50 |
| 227 | glyphosate | pyroxasulfone | isoxaflutole + ametryn | 500:1-1:500 | 1000:1-1:50 |
| 228 | glufosinate | pyroxasulfone | isoxaflutole + ametryn | 500:1-1:500 | 1000:1-1:50 |
| 229 | glyphosate | pyroxasulfone | sulcotrione + ametryn | 500:1-1:500 | 1000:1-1:50 |
| 230 | glufosinate | pyroxasulfone | sulcotrione + ametryn | 500:1-1:500 | 1000:1-1:50 |
| 231 | glyphosate | pyroxasulfone | topramezone + ametryn | 500:1-1:500 | 1000:1-1:50 |
| 232 | glufosinate | pyroxasulfone | topramezone + ametryn | 500:1-1:500 | 1000:1-1:50 |
| 233 | glyphosate | pyroxasulfone | mesotrione + ametryn | 500:1-1:500 | 1000:1-1:50 |
| 234 | glufosinate | pyroxasulfone | mesotrione + ametryn | 500:1-1:500 | 1000:1-1:50 |
| 235 | glyphosate | pyroxasulfone | tembotrione + ametryn | 500:1-1:500 | 1000:1-1:50 |
| 236 | glufosinate | pyroxasulfone | tembotrione + ametryn | 500:1-1:500 | 1000:1-1:50 |
| 237 | glyphosate | pyroxasulfone | dimethenamid-P + terbuthylazine | 500:1-1:500 | 1000:1-1:50 |
| 238 | glufosinate | pyroxasulfone | dimethenamid-P + terbuthylazine | 500:1-1:500 | 1000:1-1:50 |
| 239 | glyphosate | pyroxasulfone | dimethenamid-P + pendimethaline | 500:1-1:500 | 1000:1-1:50 |
| 240 | glufosinate | pyroxasulfone | dimethenamid-P + pendimethalin | 500:1-1:500 | 1000:1-1:50 |
| 241 | glyphosate | pyroxasulfone | dimethenamid-P + dicamba | 500:1-1:500 | 1000:1-1:50 |
| 242 | glufosinate | pyroxasulfone | dimethenamid-P + dicamba | 500:1-1:500 | 1000:1-1:50 |
| 243 | glyphosate | pyroxasulfone | dimethenamid-P + atrazine | 500:1-1:500 | 1000:1-1:50 |
| 244 | glufosinate | pyroxasulfone | dimethenamid-P + atrazine | 500:1-1:500 | 1000:1-1:50 |
| 245 | glyphosate | pyroxasulfone | dimethenamid-P + saflufenacil | 200:1-1:200 | 1000:1-1:10 |
| 246 | glufosinate | pyroxasulfone | dimethenamid-P + saflufenacil | 200:1-1:200 | 1000:1-1:10 |
| 247 | glyphosate | pyroxasulfone | dimethenamid-P + atrazine + dicamba | 500:1-1:500 | 1000:1-1:50 |
| 248 | glufosinate | pyroxasulfone | dimethenamid-P + atrazine + dicamba | 500:1-1:500 | 1000:1-1:50 |
| 249 | glyphosate | pyroxasulfone | dimethenamid-P + topramezone | 200:1-1:200 | 1500:1-1:20 |
| 250 | glufosinate | pyroxasulfone | dimethenamid-P + topramezone | 200:1-1:200 | 1500:1-1:20 |

-continued

| No. | Herbicide A* | Herbicide B | Herbicide C* | B:C w/w | A:(B + C) w/w |
|---|---|---|---|---|---|
| 251 | glyphosate | pyroxasulfone | dimethenamid-P + topramezone + dicamba | 200:1-1:500 | 1500:1-1:50 |
| 252 | glufosinate | pyroxasulfone | dimethenamid-P + topramezone + dicamba | 200:1-1:500 | 1500:1-1:50 |
| 253 | glyphosate | pyroxasulfone | dimethenamid-P + atrazine + topramezone | 200:1-1:500 | 1500:1-1:50 |
| 254 | glufosinate | pyroxasulfone | dimethenamid-P + atrazine + topramezone | 200:1-1:500 | 1500:1-1:50 |
| 255 | glyphosate | pyroxasulfone | dimethenamid-P + topramezone + terbuthylazine | 200:1-1:500 | 1500:1-1:50 |
| 256 | glufosinate | pyroxasulfone | dimethenamid-P + topramezone + terbuthylazine | 200:1-1:500 | 1500:1-1:50 |
| 257 | glyphosate | pyroxasulfone | saflufenacil + imazethapyr | 500:1-1:500 | 1000:1-1:50 |
| 258 | glufosinate | pyroxasulfone | saflufenacil + imazethapyr | 500:1-1:500 | 1000:1-1:50 |
| 259 | glyphosate | pyroxasulfone | saflufenacil + dicamba | 500:1-1:500 | 1000:1-1:50 |
| 260 | glufosinate | pyroxasulfone | saflufenacil + dicamba | 500:1-1:500 | 1000:1-1:50 |
| 261 | glyphosate | pyroxasulfone | terbuthylazin + isoxaflutole | 500:1-1:500 | 1000:1-1:50 |
| 262 | glufosinate | pyroxasulfone | terbuthylazin + isoxaflutole | 500:1-1:500 | 1000:1-1:50 |
| 263 | glyphosate | pyroxasulfone | terbuthylazin + sulcotrione | 500:1-1:500 | 1000:1-1:50 |
| 264 | glufosinate | pyroxasulfone | terbuthylazin + sulcotrione | 500:1-1:500 | 1000:1-1:50 |
| 265 | glyphosate | pyroxasulfone | terbuthylazin + topramezone | 500:1-1:500 | 1000:1-1:50 |
| 266 | glufosinate | pyroxasulfone | terbuthylazin + topramezone | 500:1-1:500 | 1000:1-1:50 |
| 267 | glyphosate | pyroxasulfone | terbuthylazin + mesotrione | 500:1-1:500 | 1000:1-1:50 |
| 268 | glufosinate | pyroxasulfone | terbuthylazin + mesotrione | 500:1-1:500 | 1000:1-1:50 |
| 269 | glyphosate | pyroxasulfone | terbuthylazin + tembotrione | 500:1-1:500 | 1000:1-1:50 |
| 270 | glufosinate | pyroxasulfone | terbuthylazin + tembotrione | 500:1-1:500 | 1000:1-1:50 |
| 271 | glyphosate | pyroxasulfone | pendimethalin + picolinafen | 200:1-1:200 | 1000:1-1:50 |
| 272 | glufosinate | pyroxasulfone | pendimethalin + picolinafen | 200:1-1:200 | 1000:1-1:50 |

*may be applied in the form of its salt continuation of table 1 (herbicide A is glyphosate, herbicide B is pyroxasulfone)

| No. | Herbicide C1 | Herbicide C2 | Herbicide C3 | Herbicide C4 | B:C* w/w | B:C1 | B:C2 | B:C3 | B:C4 | A:(B + C)* w/w |
|---|---|---|---|---|---|---|---|---|---|---|
| 273 | saflufenacil | — | — | — | 500:1-1:500 | 500:1-1:500 | — | — | — | 1000:1-1:10 |
| 274 | saflufenacil | dmta-P | — | — | 500:1-1:500 | 450:1-1:450 | 450:1-1:450 | — | — | 1000:1-1:50 |
| 275 | saflufenacil | dmta-P | atrazine | dicamba | 500:1-1:500 | 450:1-1:450 | 450:1-1:450 | 450:1-1:450 | 450:1-1:450 | 1000:1-1:50 |
| 276 | saflufenacil | imazethapyr | — | — | 500:1-1:500 | 450:1-1:450 | 450:1-1:450 | — | — | 1000:1-1:50 |
| 277 | saflufenacil | dicamba | — | — | 500:1-1:500 | 450:1-1:450 | 450:1-1:450 | — | — | 1000:1-1:50 |
| 278 | saflufenacil | atrazine | — | — | 500:1-1:500 | 450:1-1:450 | 450:1-1:450 | — | — | 1000:1-1:50 |
| 279 | saflufenacil | pendimethalin | — | — | 500:1-1:500 | 450:1-1:450 | 450:1-1:450 | — | — | 1000:1-1:50 |
| 280 | saflufenacil | flumioxazin | — | — | 500:1-1:500 | 450:1-1:450 | 450:1-1:450 | — | — | 1000:1-1:50 |
| 281 | saflufenacil | sulfentrazone | — | — | 500:1-1:500 | 450:1-1:450 | 450:1-1:450 | — | — | 1000:1-1:50 |
| 282 | saflufenacil | imazaquin | — | — | 500:1-1:500 | 450:1-1:450 | 450:1-1:450 | — | — | 1000:1-1:50 |
| 283 | saflufenacil | imazapic | — | — | 500:1-1:500 | 450:1-1:450 | 450:1-1:450 | — | — | 1000:1-1:50 |
| 284 | saflufenacil | imazapic | imazapyr | — | 500:1-1:500 | 450:1-1:450 | 450:1-1:450 | 450:1-1:450 | — | 1000:1-1:50 |
| 285 | saflufenacil | flufenaceet | — | — | 500:1-1:500 | 450:1-1:450 | 450:1-1:450 | — | — | 1000:1-1:50 |
| 286 | saflufenacil | chloransulam | — | — | 500:1-1:500 | 450:1-1:450 | 450:1-1:450 | — | — | 1000:1-1:50 |
| 287 | saflufenacil | diclosulam | — | — | 500:1-1:500 | 450:1-1:450 | 450:1-1:450 | — | — | 1000:1-1:50 |
| 288 | saflufenacil | flumetsulam | — | — | 500:1-1:500 | 450:1-1:450 | 450:1-1:450 | — | — | 1000:1-1:50 |

| No. | Herbicide C1 | Herbicide C2 | Herbicide C3 | Herbicide C4 | B:C* w/w | B:C1 | B:C2 | B:C3 | B:C4 | A:(B + C)* w/w |
|---|---|---|---|---|---|---|---|---|---|---|
| 289 | saflufenacil | diuron | — | — | 500:1-1:500 | 450:1-1:450 | 450:1-1:450 | — | — | 1000:1-1:50 |
| 290 | saflufenacil | metribuzin | — | — | 500:1-1:500 | 450:1-1:450 | 450:1-1:450 | — | — | 1000:1-1:50 |
| 291 | saflufenacil | hexazinone | — | — | 500:1-1:500 | 450:1-1:450 | 450:1-1:450 | — | — | 1000:1-1:50 |
| 292 | saflufenacil | mesotrione | — | — | 500:1-1:500 | 450:1-1:450 | 450:1-1:450 | — | — | 1000:1-1:50 |
| 293 | saflufenacil | ametryn | — | — | 500:1-1:500 | 450:1-1:450 | 450:1-1:450 | — | — | 1000:1-1:50 |
| 294 | saflufenacil | terbuthylazine | — | — | 500:1-1:500 | 450:1-1:450 | 450:1-1:450 | — | — | 1000:1-1:50 |
| 295 | saflufenacil | metazachlor | — | — | 500:1-1:500 | 450:1-1:450 | 450:1-1:450 | — | — | 1000:1-1:50 |
| 296 | saflufenacil | terbuthiuron | — | — | 500:1-1:500 | 450:1-1:450 | 450:1-1:450 | — | — | 1000:1-1:50 |
| 297 | saflufenacil | clomazone | — | — | 500:1-1:500 | 450:1-1:450 | 450:1-1:450 | — | — | 1000:1-1:50 |
| 298 | saflufenacil | hexazinone | diuron | — | 500:1-1:500 | 450:1-1:450 | 450:1-1:450 | 450:1-1:450 | — | 1000:1-1:50 |
| 299 | saflufenacil | isoxaflutole | — | — | 500:1-1:500 | 450:1-1:450 | 450:1-1:450 | — | — | 1000:1-1:50 |
| 300 | saflufenacil | atrazine | dicamba | — | 500:1-1:500 | 450:1-1:450 | 450:1-1:450 | 450:1-1:450 | — | 1000:1-1:50 |
| 301 | saflufenacil | pendimethalin | dicamba | — | 500:1-1:500 | 450:1-1:450 | 450:1-1:450 | 450:1-1:450 | — | 1000:1-1:50 |
| 302 | saflufenacil | flumioxazin | dicamba | — | 500:1-1:500 | 450:1-1:450 | 450:1-1:450 | 450:1-1:450 | — | 1000:1-1:50 |
| 303 | saflufenacil | sulfentrazone | dicamba | — | 500:1-1:500 | 450:1-1:450 | 450:1-1:450 | 450:1-1:450 | — | 1000:1-1:50 |
| 304 | saflufenacil | imazaquin | dicamba | — | 500:1-1:500 | 450:1-1:450 | 450:1-1:450 | 450:1-1:450 | — | 1000:1-1:50 |
| 305 | saflufenacil | imazapic | dicamba | — | 500:1-1:500 | 450:1-1:450 | 450:1-1:450 | 450:1-1:450 | — | 1000:1-1:50 |
| 306 | saflufenacil | imazapic | imazapyr | dicamba | 500:1-1:500 | 450:1-1:450 | 450:1-1:450 | 450:1-1:450 | 450:1-1:450 | 1000:1-1:50 |
| 307 | saflufenacil | flufenaceet | dicamba | — | 500:1-1:500 | 450:1-1:450 | 450:1-1:450 | 450:1-1:450 | — | 1000:1-1:50 |
| 308 | saflufenacil | chloransulam | dicamba | — | 500:1-1:500 | 450:1-1:450 | 450:1-1:450 | 450:1-1:450 | — | 1000:1-1:50 |
| 309 | saflufenacil | diclosulam | dicamba | — | 500:1-1:500 | 450:1-1:450 | 450:1-1:450 | 450:1-1:450 | — | 1000:1-1:50 |
| 310 | saflufenacil | flumetsulam | dicamba | — | 500:1-1:500 | 450:1-1:450 | 450:1-1:450 | 450:1-1:450 | — | 1000:1-1:50 |
| 311 | saflufenacil | diuron | dicamba | — | 500:1-1:500 | 450:1-1:450 | 450:1-1:450 | 450:1-1:450 | — | 1000:1-1:50 |
| 312 | saflufenacil | metribuzin | dicamba | — | 500:1-1:500 | 450:1-1:450 | 450:1-1:450 | 450:1-1:450 | — | 1000:1-1:50 |
| 313 | saflufenacil | hexazinone | dicamba | — | 500:1-1:500 | 450:1-1:450 | 450:1-1:450 | 450:1-1:450 | — | 1000:1-1:50 |
| 314 | saflufenacil | mesotrione | dicamba | — | 500:1-1:500 | 450:1-1:450 | 450:1-1:450 | 450:1-1:450 | — | 1000:1-1:50 |
| 315 | saflufenacil | ametryn | dicamba | — | 500:1-1:500 | 450:1-1:450 | 450:1-1:450 | 450:1-1:450 | — | 1000:1-1:50 |
| 316 | saflufenacil | terbuthylazine | dicamba | — | 500:1-1:500 | 450:1-1:450 | 450:1-1:450 | 450:1-1:450 | — | 1000:1-1:50 |
| 317 | saflufenacil | metazachlor | dicamba | — | 500:1-1:500 | 450:1-1:450 | 450:1-1:450 | 450:1-1:450 | — | 1000:1-1:50 |
| 318 | saflufenacil | terbuthiuron | dicamba | — | 500:1-1:500 | 450:1-1:450 | 450:1-1:450 | 450:1-1:450 | — | 1000:1-1:50 |
| 319 | saflufenacil | clomazone | dicamba | — | 500:1-1:500 | 450:1-1:450 | 450:1-1:450 | 450:1-1:450 | — | 1000:1-1:50 |
| 320 | saflufenacil | hexazinone | diuron | dicamba | 500:1-1:500 | 450:1-1:450 | 450:1-1:450 | 450:1-1:450 | 450:1-1:450 | 1000:1-1:50 |
| 321 | saflufenacil | isoxaflutole | dicamba | — | 500:1-1:500 | 450:1-1:450 | 450:1-1:450 | 450:1-1:450 | — | 1000:1-1:50 |
| 322 | compound A | — | — | — | 500:1-1:500 | 500:1-1:500 | — | — | — | 1000:1-1:10 |
| 323 | compound A | dmta-P | — | — | 500:1-1:500 | 450:1-1:450 | 450:1-1:450 | — | — | 1000:1-1:50 |
| 324 | compound A | dmta-P | atrazine | dicamba | 500:1-1:500 | 450:1-1:450 | 450:1-1:450 | 450:1-1:450 | 450:1-1:450 | 1000:1-1:50 |
| 325 | compound A | imazethapyr | — | — | 500:1-1:500 | 450:1-1:450 | 450:1-1:450 | — | — | 1000:1-1:50 |
| 326 | compound A | dicamba | — | — | 500:1-1:500 | 450:1-1:450 | 450:1-1:450 | — | — | 1000:1-1:50 |
| 327 | compound A | atrazine | — | — | 500:1-1:500 | 450:1-1:450 | 450:1-1:450 | — | — | 1000:1-1:50 |
| 328 | compound A | pendimethalin | — | — | 500:1-1:500 | 450:1-1:450 | 450:1-1:450 | — | — | 1000:1-1:50 |
| 329 | compound A | flumioxazin | — | — | 500:1-1:500 | 450:1-1:450 | 450:1-1:450 | — | — | 1000:1-1:50 |
| 330 | compound A | sulfentrazone | — | — | 500:1-1:500 | 450:1-1:450 | 450:1-1:450 | — | — | 1000:1-1:50 |
| 331 | compound A | imazaquin | — | — | 500:1-1:500 | 450:1-1:450 | 450:1-1:450 | — | — | 1000:1-1:50 |
| 332 | compound A | imazapic | — | — | 500:1-1:500 | 450:1-1:450 | 450:1-1:450 | — | — | 1000:1-1:50 |
| 333 | compound A | imazapic | imazapyr | — | 500:1-1:500 | 450:1-1:450 | 450:1-1:450 | 450:1-1:450 | — | 1000:1-1:50 |
| 334 | compound A | flufenaceet | — | — | 500:1-1:500 | 450:1-1:450 | 450:1-1:450 | — | — | 1000:1-1:50 |
| 335 | compound A | chloransulam | — | — | 500:1-1:500 | 450:1-1:450 | 450:1-1:450 | — | — | 1000:1-1:50 |
| 336 | compound A | diclosulam | — | — | 500:1-1:500 | 450:1-1:450 | 450:1-1:450 | — | — | 1000:1-1:50 |
| 337 | compound A | flumetsulam | — | — | 500:1-1:500 | 450:1-1:450 | 450:1-1:450 | — | — | 1000:1-1:50 |
| 338 | compound A | diuron | — | — | 500:1-1:500 | 450:1-1:450 | 450:1-1:450 | — | — | 1000:1-1:50 |
| 339 | compound A | metribuzin | — | — | 500:1-1:500 | 450:1-1:450 | 450:1-1:450 | — | — | 1000:1-1:50 |
| 340 | compound A | hexazinone | — | — | 500:1-1:500 | 450:1-1:450 | 450:1-1:450 | — | — | 1000:1-1:50 |
| 341 | compound A | mesotrione | — | — | 500:1-1:500 | 450:1-1:450 | 450:1-1:450 | — | — | 1000:1-1:50 |
| 342 | compound A | ametryn | — | — | 500:1-1:500 | 450:1-1:450 | 450:1-1:450 | — | — | 1000:1-1:50 |
| 343 | compound A | terbuthylazine | — | — | 500:1-1:500 | 450:1-1:450 | 450:1-1:450 | — | — | 1000:1-1:50 |
| 344 | compound A | metazachlor | — | — | 500:1-1:500 | 450:1-1:450 | 450:1-1:450 | — | — | 1000:1-1:50 |
| 345 | compound A | terbuthiuron | — | — | 500:1-1:500 | 450:1-1:450 | 450:1-1:450 | — | — | 1000:1-1:50 |
| 346 | compound A | clomazone | — | — | 500:1-1:500 | 450:1-1:450 | 450:1-1:450 | — | — | 1000:1-1:50 |
| 347 | compound A | hexazinone | diuron | — | 500:1-1:500 | 450:1-1:450 | 450:1-1:450 | 450:1-1:450 | — | 1000:1-1:50 |
| 348 | compound A | isoxaflutole | — | — | 500:1-1:500 | 450:1-1:450 | 450:1-1:450 | — | — | 1000:1-1:50 |
| 349 | compound A | atrazine | dicamba | — | 500:1-1:500 | 450:1-1:450 | 450:1-1:450 | 450:1-1:450 | — | 1000:1-1:50 |
| 350 | compound A | pendimethalin | dicamba | — | 500:1-1:500 | 450:1-1:450 | 450:1-1:450 | 450:1-1:450 | — | 1000:1-1:50 |
| 351 | compound A | flumioxazin | dicamba | — | 500:1-1:500 | 450:1-1:450 | 450:1-1:450 | 450:1-1:450 | — | 1000:1-1:50 |
| 352 | compound A | sulfentrazone | dicamba | — | 500:1-1:500 | 450:1-1:450 | 450:1-1:450 | 450:1-1:450 | — | 1000:1-1:50 |
| 353 | compound A | imazaquin | dicamba | — | 500:1-1:500 | 450:1-1:450 | 450:1-1:450 | 450:1-1:450 | — | 1000:1-1:50 |
| 354 | compound A | imazapic | dicamba | — | 500:1-1:500 | 450:1-1:450 | 450:1-1:450 | 450:1-1:450 | — | 1000:1-1:50 |
| 355 | compound A | imazapic | imazapyr | dicamba | 500:1-1:500 | 450:1-1:450 | 450:1-1:450 | 450:1-1:450 | 450:1-1:450 | 1000:1-1:50 |
| 356 | compound A | flufenaceet | dicamba | — | 500:1-1:500 | 450:1-1:450 | 450:1-1:450 | 450:1-1:450 | — | 1000:1-1:50 |
| 357 | compound A | chloransulam | dicamba | — | 500:1-1:500 | 450:1-1:450 | 450:1-1:450 | 450:1-1:450 | — | 1000:1-1:50 |
| 358 | compound A | diclosulam | dicamba | — | 500:1-1:500 | 450:1-1:450 | 450:1-1:450 | 450:1-1:450 | — | 1000:1-1:50 |
| 359 | compound A | flumetsulam | dicamba | — | 500:1-1:500 | 450:1-1:450 | 450:1-1:450 | 450:1-1:450 | — | 1000:1-1:50 |
| 360 | compound A | diuron | dicamba | — | 500:1-1:500 | 450:1-1:450 | 450:1-1:450 | 450:1-1:450 | — | 1000:1-1:50 |
| 361 | compound A | metribuzin | dicamba | — | 500:1-1:500 | 450:1-1:450 | 450:1-1:450 | 450:1-1:450 | — | 1000:1-1:50 |
| 362 | compound A | hexazinone | dicamba | — | 500:1-1:500 | 450:1-1:450 | 450:1-1:450 | 450:1-1:450 | — | 1000:1-1:50 |
| 363 | compound A | mesotrione | dicamba | — | 500:1-1:500 | 450:1-1:450 | 450:1-1:450 | 450:1-1:450 | — | 1000:1-1:50 |
| 364 | compound A | ametryn | dicamba | — | 500:1-1:500 | 450:1-1:450 | 450:1-1:450 | 450:1-1:450 | — | 1000:1-1:50 |

| No. | Herbicide C1 | Herbicide C2 | Herbicide C3 | Herbicide C4 | B:C* w/w | B:C1 | B:C2 | B:C3 | B:C4 | A:(B + C)* w/w |
|---|---|---|---|---|---|---|---|---|---|---|
| 365 | compound A | terbuthylazine | dicamba | — | 500:1-1:500 | 450:1-1:450 | 450:1-1:450 | 450:1-1:450 | — | 1000:1-1:50 |
| 366 | compound A | metazachlor | dicamba | — | 500:1-1:500 | 450:1-1:450 | 450:1-1:450 | 450:1-1:450 | — | 1000:1-1:50 |
| 367 | compound A | terbuthiuron | dicamba | — | 500:1-1:500 | 450:1-1:450 | 450:1-1:450 | 450:1-1:450 | — | 1000:1-1:50 |
| 368 | compound A | clomazone | dicamba | — | 500:1-1:500 | 450:1-1:450 | 450:1-1:450 | 450:1-1:450 | — | 1000:1-1:50 |
| 369 | compound A | hexazinone | diuron | dicamba | 500:1-1:500 | 450:1-1:450 | 450:1-1:450 | 450:1-1:450 | 450:1-1:450 | 1000:1-1:50 |
| 370 | compound A | isoxaflutole | dicamba | — | 500:1-1:500 | 450:1-1:450 | 450:1-1:450 | 450:1-1:450 | — | 1000:1-1:50 |
| 371 | compound B | — | — | — | 500:1-1:500 | 500:1-1:500 | — | — | — | 1000:1-1:10 |
| 372 | compound B | dmta-P | — | — | 500:1-1:500 | 450:1-1:450 | 450:1-1:450 | — | — | 1000:1-1:50 |
| 373 | compound B | dmta-P | atrazine | dicamba | 500:1-1:500 | 450:1-1:450 | 450:1-1:450 | 450:1-1:450 | 450:1-1:450 | 1000:1-1:50 |
| 374 | compound B | imazethapyr | — | — | 500:1-1:500 | 450:1-1:450 | 450:1-1:450 | — | — | 1000:1-1:50 |
| 375 | compound B | dicamba | — | — | 500:1-1:500 | 450:1-1:450 | 450:1-1:450 | — | — | 1000:1-1:50 |
| 376 | compound B | atrazine | — | — | 500:1-1:500 | 450:1-1:450 | 450:1-1:450 | — | — | 1000:1-1:50 |
| 377 | compound B | pendimethalin | — | — | 500:1-1:500 | 450:1-1:450 | 450:1-1:450 | — | — | 1000:1-1:50 |
| 378 | compound B | flumioxazin | — | — | 500:1-1:500 | 450:1-1:450 | 450:1-1:450 | — | — | 1000:1-1:50 |
| 379 | compound B | sulfentrazone | — | — | 500:1-1:500 | 450:1-1:450 | 450:1-1:450 | — | — | 1000:1-1:50 |
| 380 | compound B | imazaquin | — | — | 500:1-1:500 | 450:1-1:450 | 450:1-1:450 | — | — | 1000:1-1:50 |
| 381 | compound B | imazapic | — | — | 500:1-1:500 | 450:1-1:450 | 450:1-1:450 | — | — | 1000:1-1:50 |
| 382 | compound B | imazapic | imazapyr | — | 500:1-1:500 | 450:1-1:450 | 450:1-1:450 | 450:1-1:450 | — | 1000:1-1:50 |
| 383 | compound B | flufenaceet | — | — | 500:1-1:500 | 450:1-1:450 | 450:1-1:450 | — | — | 1000:1-1:50 |
| 384 | compound B | chloransulam | — | — | 500:1-1:500 | 450:1-1:450 | 450:1-1:450 | — | — | 1000:1-1:50 |
| 385 | compound B | diclosulam | — | — | 500:1-1:500 | 450:1-1:450 | 450:1-1:450 | — | — | 1000:1-1:50 |
| 386 | compound B | flumetsulam | — | — | 500:1-1:500 | 450:1-1:450 | 450:1-1:450 | — | — | 1000:1-1:50 |
| 387 | compound B | diuron | — | — | 500:1-1:500 | 450:1-1:450 | 450:1-1:450 | — | — | 1000:1-1:50 |
| 388 | compound B | metribuzin | — | — | 500:1-1:500 | 450:1-1:450 | 450:1-1:450 | — | — | 1000:1-1:50 |
| 389 | compound B | hexazinone | — | — | 500:1-1:500 | 450:1-1:450 | 450:1-1:450 | — | — | 1000:1-1:50 |
| 390 | compound B | mesotrione | — | — | 500:1-1:500 | 450:1-1:450 | 450:1-1:450 | — | — | 1000:1-1:50 |
| 391 | compound B | ametryn | — | — | 500:1-1:500 | 450:1-1:450 | 450:1-1:450 | — | — | 1000:1-1:50 |
| 392 | compound B | terbuthylazine | — | — | 500:1-1:500 | 450:1-1:450 | 450:1-1:450 | — | — | 1000:1-1:50 |
| 393 | compound B | metazachlor | — | — | 500:1-1:500 | 450:1-1:450 | 450:1-1:450 | — | — | 1000:1-1:50 |
| 394 | compound B | terbuthiuron | — | — | 500:1-1:500 | 450:1-1:450 | 450:1-1:450 | — | — | 1000:1-1:50 |
| 395 | compound B | clomazone | — | — | 500:1-1:500 | 450:1-1:450 | 450:1-1:450 | — | — | 1000:1-1:50 |
| 396 | compound B | hexazinone | diuron | — | 500:1-1:500 | 450:1-1:450 | 450:1-1:450 | 450:1-1:450 | — | 1000:1-1:50 |
| 397 | compound B | isoxaflutole | — | — | 500:1-1:500 | 450:1-1:450 | 450:1-1:450 | — | — | 1000:1-1:50 |
| 398 | compound B | atrazine | dicamba | — | 500:1-1:500 | 450:1-1:450 | 450:1-1:450 | 450:1-1:450 | — | 1000:1-1:50 |
| 399 | compound B | pendimethalin | dicamba | — | 500:1-1:500 | 450:1-1:450 | 450:1-1:450 | 450:1-1:450 | — | 1000:1-1:50 |
| 400 | compound B | flumioxazin | dicamba | — | 500:1-1:500 | 450:1-1:450 | 450:1-1:450 | 450:1-1:450 | — | 1000:1-1:50 |
| 401 | compound B | sulfentrazone | dicamba | — | 500:1-1:500 | 450:1-1:450 | 450:1-1:450 | 450:1-1:450 | — | 1000:1-1:50 |
| 402 | compound B | imazaquin | dicamba | — | 500:1-1:500 | 450:1-1:450 | 450:1-1:450 | 450:1-1:450 | — | 1000:1-1:50 |
| 403 | compound B | imazapic | dicamba | — | 500:1-1:500 | 450:1-1:450 | 450:1-1:450 | 450:1-1:450 | — | 1000:1-1:50 |
| 404 | compound B | imazapic | imazapyr | dicamba | 500:1-1:500 | 450:1-1:450 | 450:1-1:450 | 450:1-1:450 | 450:1-1:450 | 1000:1-1:50 |
| 405 | compound B | flufenaceet | dicamba | — | 500:1-1:500 | 450:1-1:450 | 450:1-1:450 | 450:1-1:450 | — | 1000:1-1:50 |
| 406 | compound B | chloransulam | dicamba | — | 500:1-1:500 | 450:1-1:450 | 450:1-1:450 | 450:1-1:450 | — | 1000:1-1:50 |
| 407 | compound B | diclosulam | dicamba | — | 500:1-1:500 | 450:1-1:450 | 450:1-1:450 | 450:1-1:450 | — | 1000:1-1:50 |
| 408 | compound B | flumetsulam | dicamba | — | 500:1-1:500 | 450:1-1:450 | 450:1-1:450 | 450:1-1:450 | — | 1000:1-1:50 |
| 409 | compound B | diuron | dicamba | — | 500:1-1:500 | 450:1-1:450 | 450:1-1:450 | 450:1-1:450 | — | 1000:1-1:50 |
| 410 | compound B | metribuzin | dicamba | — | 500:1-1:500 | 450:1-1:450 | 450:1-1:450 | 450:1-1:450 | — | 1000:1-1:50 |
| 411 | compound B | hexazinone | dicamba | — | 500:1-1:500 | 450:1-1:450 | 450:1-1:450 | 450:1-1:450 | — | 1000:1-1:50 |
| 412 | compound B | mesotrione | dicamba | — | 500:1-1:500 | 450:1-1:450 | 450:1-1:450 | 450:1-1:450 | — | 1000:1-1:50 |
| 413 | compound B | ametryn | dicamba | — | 500:1-1:500 | 450:1-1:450 | 450:1-1:450 | 450:1-1:450 | — | 1000:1-1:50 |
| 414 | compound B | terbuthylazine | dicamba | — | 500:1-1:500 | 450:1-1:450 | 450:1-1:450 | 450:1-1:450 | — | 1000:1-1:50 |
| 415 | compound B | metazachlor | dicamba | — | 500:1-1:500 | 450:1-1:450 | 450:1-1:450 | 450:1-1:450 | — | 1000:1-1:50 |
| 416 | compound B | terbuthiuron | dicamba | — | 500:1-1:500 | 450:1-1:450 | 450:1-1:450 | 450:1-1:450 | — | 1000:1-1:50 |
| 417 | compound B | clomazone | dicamba | — | 500:1-1:500 | 450:1-1:450 | 450:1-1:450 | 450:1-1:450 | — | 1000:1-1:50 |
| 418 | compound B | hexazinone | diuron | dicamba | 500:1-1:500 | 450:1-1:450 | 450:1-1:450 | 450:1-1:450 | 450:1-1:450 | 1000:1-1:50 |
| 419 | compound B | isoxaflutole | dicamba | — | 500:1-1:500 | 450:1-1:450 | 450:1-1:450 | 450:1-1:450 | — | 1000:1-1:50 |
| 420 | compound C | — | — | — | 500:1-1:500 | 500:1-1:500 | — | — | — | 1000:1-1:10 |
| 421 | compound C | dmta-P | — | — | 500:1-1:500 | 450:1-1:450 | 450:1-1:450 | — | — | 1000:1-1:50 |
| 422 | compound C | dmta-P | atrazine | dicamba | 500:1-1:500 | 450:1-1:450 | 450:1-1:450 | 450:1-1:450 | 450:1-1:450 | 1000:1-1:50 |
| 423 | compound C | imazethapyr | — | — | 500:1-1:500 | 450:1-1:450 | 450:1-1:450 | — | — | 1000:1-1:50 |
| 424 | compound C | dicamba | — | — | 500:1-1:500 | 450:1-1:450 | 450:1-1:450 | — | — | 1000:1-1:50 |
| 425 | compound C | atrazine | — | — | 500:1-1:500 | 450:1-1:450 | 450:1-1:450 | — | — | 1000:1-1:50 |
| 426 | compound C | pendimethalin | — | — | 500:1-1:500 | 450:1-1:450 | 450:1-1:450 | — | — | 1000:1-1:50 |
| 427 | compound C | flumioxazin | — | — | 500:1-1:500 | 450:1-1:450 | 450:1-1:450 | — | — | 1000:1-1:50 |
| 428 | compound C | sulfentrazone | — | — | 500:1-1:500 | 450:1-1:450 | 450:1-1:450 | — | — | 1000:1-1:50 |
| 429 | compound C | imazaquin | — | — | 500:1-1:500 | 450:1-1:450 | 450:1-1:450 | — | — | 1000:1-1:50 |
| 430 | compound C | imazapic | — | — | 500:1-1:500 | 450:1-1:450 | 450:1-1:450 | — | — | 1000:1-1:50 |
| 431 | compound C | imazapic | imazapyr | — | 500:1-1:500 | 450:1-1:450 | 450:1-1:450 | 450:1-1:450 | — | 1000:1-1:50 |
| 432 | compound C | flufenaceet | — | — | 500:1-1:500 | 450:1-1:450 | 450:1-1:450 | — | — | 1000:1-1:50 |
| 433 | compound C | chloransulam | — | — | 500:1-1:500 | 450:1-1:450 | 450:1-1:450 | — | — | 1000:1-1:50 |
| 434 | compound C | diclosulam | — | — | 500:1-1:500 | 450:1-1:450 | 450:1-1:450 | — | — | 1000:1-1:50 |
| 435 | compound C | flumetsulam | — | — | 500:1-1:500 | 450:1-1:450 | 450:1-1:450 | — | — | 1000:1-1:50 |
| 436 | compound C | diuron | — | — | 500:1-1:500 | 450:1-1:450 | 450:1-1:450 | — | — | 1000:1-1:50 |
| 437 | compound C | metribuzin | — | — | 500:1-1:500 | 450:1-1:450 | 450:1-1:450 | — | — | 1000:1-1:50 |
| 438 | compound C | hexazinone | — | — | 500:1-1:500 | 450:1-1:450 | 450:1-1:450 | — | — | 1000:1-1:50 |
| 439 | compound C | mesotrione | — | — | 500:1-1:500 | 450:1-1:450 | 450:1-1:450 | — | — | 1000:1-1:50 |
| 440 | compound C | ametryn | — | — | 500:1-1:500 | 450:1-1:450 | 450:1-1:450 | — | — | 1000:1-1:50 |

-continued

| No. | Herbicide C1 | Herbicide C2 | Herbicide C3 | Herbicide C4 | B:C* w/w | B:C1 | B:C2 | B:C3 | B:C4 | A:(B + C)* w/w |
|---|---|---|---|---|---|---|---|---|---|---|
| 441 | compound C | terbuthylazine | — | — | 500:1-1:500 | 450:1-1:450 | 450:1-1:450 | — | — | 1000:1-1:50 |
| 442 | compound C | metazachlor | — | — | 500:1-1:500 | 450:1-1:450 | 450:1-1:450 | — | — | 1000:1-1:50 |
| 443 | compound C | terbuthiuron | — | — | 500:1-1:500 | 450:1-1:450 | 450:1-1:450 | — | — | 1000:1-1:50 |
| 444 | compound C | clomazone | — | — | 500:1-1:500 | 450:1-1:450 | 450:1-1:450 | — | — | 1000:1-1:50 |
| 445 | compound C | hexazinone | diuron | — | 500:1-1:500 | 450:1-1:450 | 450:1-1:450 | 450:1-1:450 | — | 1000:1-1:50 |
| 446 | compound C | isoxaflutole | — | — | 500:1-1:500 | 450:1-1:450 | 450:1-1:450 | — | — | 1000:1-1:50 |
| 447 | compound C | atrazine | dicamba | — | 500:1-1:500 | 450:1-1:450 | 450:1-1:450 | 450:1-1:450 | — | 1000:1-1:50 |
| 448 | compound C | pendimethalin | dicamba | — | 500:1-1:500 | 450:1-1:450 | 450:1-1:450 | 450:1-1:450 | — | 1000:1-1:50 |
| 449 | compound C | flumioxazin | dicamba | — | 500:1-1:500 | 450:1-1:450 | 450:1-1:450 | 450:1-1:450 | — | 1000:1-1:50 |
| 450 | compound C | sulfentrazone | dicamba | — | 500:1-1:500 | 450:1-1:450 | 450:1-1:450 | 450:1-1:450 | — | 1000:1-1:50 |
| 451 | compound C | imazaquin | dicamba | — | 500:1-1:500 | 450:1-1:450 | 450:1-1:450 | 450:1-1:450 | — | 1000:1-1:50 |
| 452 | compound C | imazapic | dicamba | — | 500:1-1:500 | 450:1-1:450 | 450:1-1:450 | 450:1-1:450 | — | 1000:1-1:50 |
| 453 | compound C | imazapic | imazapyr | dicamba | 500:1-1:500 | 450:1-1:450 | 450:1-1:450 | 450:1-1:450 | 450:1-1:450 | 1000:1-1:50 |
| 454 | compound C | flufenaceet | dicamba | — | 500:1-1:500 | 450:1-1:450 | 450:1-1:450 | 450:1-1:450 | — | 1000:1-1:50 |
| 455 | compound C | chloransulam | dicamba | — | 500:1-1:500 | 450:1-1:450 | 450:1-1:450 | 450:1-1:450 | — | 1000:1-1:50 |
| 456 | compound C | diclosulam | dicamba | — | 500:1-1:500 | 450:1-1:450 | 450:1-1:450 | 450:1-1:450 | — | 1000:1-1:50 |
| 457 | compound C | flumetsulam | dicamba | — | 500:1-1:500 | 450:1-1:450 | 450:1-1:450 | 450:1-1:450 | — | 1000:1-1:50 |
| 458 | compound C | diuron | dicamba | — | 500:1-1:500 | 450:1-1:450 | 450:1-1:450 | 450:1-1:450 | — | 1000:1-1:50 |
| 459 | compound C | metribuzin | dicamba | — | 500:1-1:500 | 450:1-1:450 | 450:1-1:450 | 450:1-1:450 | — | 1000:1-1:50 |
| 460 | compound C | hexazinone | dicamba | — | 500:1-1:500 | 450:1-1:450 | 450:1-1:450 | 450:1-1:450 | — | 1000:1-1:50 |
| 461 | compound C | mesotrione | dicamba | — | 500:1-1:500 | 450:1-1:450 | 450:1-1:450 | 450:1-1:450 | — | 1000:1-1:50 |
| 462 | compound C | ametryn | dicamba | — | 500:1-1:500 | 450:1-1:450 | 450:1-1:450 | 450:1-1:450 | — | 1000:1-1:50 |
| 463 | compound C | terbuthylazine | dicamba | — | 500:1-1:500 | 450:1-1:450 | 450:1-1:450 | 450:1-1:450 | — | 1000:1-1:50 |
| 464 | compound C | metazachlor | dicamba | — | 500:1-1:500 | 450:1-1:450 | 450:1-1:450 | 450:1-1:450 | — | 1000:1-1:50 |
| 465 | compound C | terbuthiuron | dicamba | — | 500:1-1:500 | 450:1-1:450 | 450:1-1:450 | 450:1-1:450 | — | 1000:1-1:50 |
| 466 | compound C | clomazone | dicamba | — | 500:1-1:500 | 450:1-1:450 | 450:1-1:450 | 450:1-1:450 | — | 1000:1-1:50 |
| 467 | compound C | hexazinone | diuron | dicamba | 500:1-1:500 | 450:1-1:450 | 450:1-1:450 | 450:1-1:450 | 450:1-1:450 | 1000:1-1:50 |
| 468 | compound C | isoxaflutole | dicamba | — | 500:1-1:500 | 450:1-1:450 | 450:1-1:450 | — | — | 1000:1-1:50 |
| 469 | compound D | — | — | — | 500:1-1:500 | 500:1-1:500 | — | — | — | 1000:1-1:10 |
| 470 | compound D | dmta-P | — | — | 500:1-1:500 | 450:1-1:450 | 450:1-1:450 | — | — | 1000:1-1:50 |
| 471 | compound D | dmta-P | atrazine | dicamba | 500:1-1:500 | 450:1-1:450 | 450:1-1:450 | 450:1-1:450 | 450:1-1:450 | 1000:1-1:50 |
| 472 | compound D | imazethapyr | — | — | 500:1-1:500 | 450:1-1:450 | 450:1-1:450 | — | — | 1000:1-1:50 |
| 473 | compound D | dicamba | — | — | 500:1-1:500 | 450:1-1:450 | 450:1-1:450 | — | — | 1000:1-1:50 |
| 474 | compound D | atrazine | — | — | 500:1-1:500 | 450:1-1:450 | 450:1-1:450 | — | — | 1000:1-1:50 |
| 475 | compound D | pendimethalin | — | — | 500:1-1:500 | 450:1-1:450 | 450:1-1:450 | — | — | 1000:1-1:50 |
| 476 | compound D | flumioxazin | — | — | 500:1-1:500 | 450:1-1:450 | 450:1-1:450 | — | — | 1000:1-1:50 |
| 477 | compound D | sulfentrazone | — | — | 500:1-1:500 | 450:1-1:450 | 450:1-1:450 | — | — | 1000:1-1:50 |
| 478 | compound D | imazaquin | — | — | 500:1-1:500 | 450:1-1:450 | 450:1-1:450 | — | — | 1000:1-1:50 |
| 479 | compound D | imazapic | — | — | 500:1-1:500 | 450:1-1:450 | 450:1-1:450 | — | — | 1000:1-1:50 |
| 480 | compound D | imazapic | imazapyr | — | 500:1-1:500 | 450:1-1:450 | 450:1-1:450 | 450:1-1:450 | — | 1000:1-1:50 |
| 481 | compound D | flufenaceet | — | — | 500:1-1:500 | 450:1-1:450 | 450:1-1:450 | — | — | 1000:1-1:50 |
| 482 | compound D | chloransulam | — | — | 500:1-1:500 | 450:1-1:450 | 450:1-1:450 | — | — | 1000:1-1:50 |
| 483 | compound D | diclosulam | — | — | 500:1-1:500 | 450:1-1:450 | 450:1-1:450 | — | — | 1000:1-1:50 |
| 484 | compound D | flumetsulam | — | — | 500:1-1:500 | 450:1-1:450 | 450:1-1:450 | — | — | 1000:1-1:50 |
| 485 | compound D | diuron | — | — | 500:1-1:500 | 450:1-1:450 | 450:1-1:450 | — | — | 1000:1-1:50 |
| 486 | compound D | metribuzin | — | — | 500:1-1:500 | 450:1-1:450 | 450:1-1:450 | — | — | 1000:1-1:50 |
| 487 | compound D | hexazinone | — | — | 500:1-1:500 | 450:1-1:450 | 450:1-1:450 | — | — | 1000:1-1:50 |
| 488 | compound D | mesotrione | — | — | 500:1-1:500 | 450:1-1:450 | 450:1-1:450 | — | — | 1000:1-1:50 |
| 489 | compound D | ametryn | — | — | 500:1-1:500 | 450:1-1:450 | 450:1-1:450 | — | — | 1000:1-1:50 |
| 490 | compound D | terbuthylazine | — | — | 500:1-1:500 | 450:1-1:450 | 450:1-1:450 | — | — | 1000:1-1:50 |
| 491 | compound D | metazachlor | — | — | 500:1-1:500 | 450:1-1:450 | 450:1-1:450 | — | — | 1000:1-1:50 |
| 492 | compound D | terbuthiuron | — | — | 500:1-1:500 | 450:1-1:450 | 450:1-1:450 | — | — | 1000:1-1:50 |
| 493 | compound D | clomazone | — | — | 500:1-1:500 | 450:1-1:450 | 450:1-1:450 | — | — | 1000:1-1:50 |
| 494 | compound D | hexazinone | diuron | — | 500:1-1:500 | 450:1-1:450 | 450:1-1:450 | 450:1-1:450 | — | 1000:1-1:50 |
| 495 | compound D | isoxaflutole | — | — | 500:1-1:500 | 450:1-1:450 | 450:1-1:450 | — | — | 1000:1-1:50 |
| 496 | compound D | atrazine | dicamba | — | 500:1-1:500 | 450:1-1:450 | 450:1-1:450 | 450:1-1:450 | — | 1000:1-1:50 |
| 497 | compound D | pendimethalin | dicamba | — | 500:1-1:500 | 450:1-1:450 | 450:1-1:450 | 450:1-1:450 | — | 1000:1-1:50 |
| 498 | compound D | flumioxazin | dicamba | — | 500:1-1:500 | 450:1-1:450 | 450:1-1:450 | 450:1-1:450 | — | 1000:1-1:50 |
| 499 | compound D | sulfentrazone | dicamba | — | 500:1-1:500 | 450:1-1:450 | 450:1-1:450 | 450:1-1:450 | — | 1000:1-1:50 |
| 500 | compound D | imazaquin | dicamba | — | 500:1-1:500 | 450:1-1:450 | 450:1-1:450 | 450:1-1:450 | — | 1000:1-1:50 |
| 501 | compound D | imazapic | dicamba | — | 500:1-1:500 | 450:1-1:450 | 450:1-1:450 | 450:1-1:450 | — | 1000:1-1:50 |
| 502 | compound D | imazapic | imazapyr | dicamba | 500:1-1:500 | 450:1-1:450 | 450:1-1:450 | 450:1-1:450 | 450:1-1:450 | 1000:1-1:50 |
| 503 | compound D | flufenaceet | dicamba | — | 500:1-1:500 | 450:1-1:450 | 450:1-1:450 | 450:1-1:450 | — | 1000:1-1:50 |
| 504 | compound D | chloransulam | dicamba | — | 500:1-1:500 | 450:1-1:450 | 450:1-1:450 | 450:1-1:450 | — | 1000:1-1:50 |
| 505 | compound D | diclosulam | dicamba | — | 500:1-1:500 | 450:1-1:450 | 450:1-1:450 | 450:1-1:450 | — | 1000:1-1:50 |
| 506 | compound D | flumetsulam | dicamba | — | 500:1-1:500 | 450:1-1:450 | 450:1-1:450 | 450:1-1:450 | — | 1000:1-1:50 |
| 507 | compound D | diuron | dicamba | — | 500:1-1:500 | 450:1-1:450 | 450:1-1:450 | 450:1-1:450 | — | 1000:1-1:50 |
| 508 | compound D | metribuzin | dicamba | — | 500:1-1:500 | 450:1-1:450 | 450:1-1:450 | 450:1-1:450 | — | 1000:1-1:50 |
| 509 | compound D | hexazinone | dicamba | — | 500:1-1:500 | 450:1-1:450 | 450:1-1:450 | 450:1-1:450 | — | 1000:1-1:50 |
| 510 | compound D | mesotrione | dicamba | — | 500:1-1:500 | 450:1-1:450 | 450:1-1:450 | 450:1-1:450 | — | 1000:1-1:50 |
| 511 | compound D | ametryn | dicamba | — | 500:1-1:500 | 450:1-1:450 | 450:1-1:450 | 450:1-1:450 | — | 1000:1-1:50 |
| 512 | compound D | terbuthylazine | dicamba | — | 500:1-1:500 | 450:1-1:450 | 450:1-1:450 | 450:1-1:450 | — | 1000:1-1:50 |
| 513 | compound D | metazachlor | dicamba | — | 500:1-1:500 | 450:1-1:450 | 450:1-1:450 | 450:1-1:450 | — | 1000:1-1:50 |
| 514 | compound D | terbuthiuron | dicamba | — | 500:1-1:500 | 450:1-1:450 | 450:1-1:450 | 450:1-1:450 | — | 1000:1-1:50 |
| 515 | compound D | clomazone | dicamba | — | 500:1-1:500 | 450:1-1:450 | 450:1-1:450 | 450:1-1:450 | — | 1000:1-1:50 |
| 516 | compound D | hexazinone | diuron | dicamba | 500:1-1:500 | 450:1-1:450 | 450:1-1:450 | 450:1-1:450 | 450:1-1:450 | 1000:1-1:50 |

| No. | Herbicide C1 | Herbicide C2 | Herbicide C3 | Herbicide C4 | B:C* w/w | B:C1 | B:C2 | B:C3 | B:C4 | A:(B + C)* w/w |
|---|---|---|---|---|---|---|---|---|---|---|
| 517 | compound D | isoxaflutole | dicamba | — | 500:1-1:500 | 450:1-1:450 | 450:1-1:450 | 450:1-1:450 | — | 1000:1-1:50 |
| 518 | compound E | — | — | — | 500:1-1:500 | 500:1-1:500 | — | — | — | 1000:1-1:50 |
| 519 | compound E | dmta-P | — | — | 500:1-1:500 | 450:1-1:450 | 450:1-1:450 | — | — | 1000:1-1:50 |
| 520 | compound E | dmta-P | atrazine | dicamba | 500:1-1:500 | 450:1-1:450 | 450:1-1:450 | 450:1-1:450 | 450:1-1:450 | 1000:1-1:50 |
| 521 | compound E | imazethapyr | — | — | 500:1-1:500 | 450:1-1:450 | 450:1-1:450 | — | — | 1000:1-1:50 |
| 522 | compound E | dicamba | — | — | 500:1-1:500 | 450:1-1:450 | 450:1-1:450 | — | — | 1000:1-1:50 |
| 523 | compound E | atrazine | — | — | 500:1-1:500 | 450:1-1:450 | 450:1-1:450 | — | — | 1000:1-1:50 |
| 524 | compound E | pendimethalin | — | — | 500:1-1:500 | 450:1-1:450 | 450:1-1:450 | — | — | 1000:1-1:50 |
| 525 | compound E | flumioxazin | — | — | 500:1-1:500 | 450:1-1:450 | 450:1-1:450 | — | — | 1000:1-1:50 |
| 526 | compound E | sulfentrazone | — | — | 500:1-1:500 | 450:1-1:450 | 450:1-1:450 | — | — | 1000:1-1:50 |
| 527 | compound E | imazaquin | — | — | 500:1-1:500 | 450:1-1:450 | 450:1-1:450 | — | — | 1000:1-1:50 |
| 528 | compound E | imazapic | — | — | 500:1-1:500 | 450:1-1:450 | 450:1-1:450 | — | — | 1000:1-1:50 |
| 529 | compound E | imazapic | imazapyr | — | 500:1-1:500 | 450:1-1:450 | 450:1-1:450 | 450:1-1:450 | — | 1000:1-1:50 |
| 530 | compound E | flufenaceet | — | — | 500:1-1:500 | 450:1-1:450 | 450:1-1:450 | — | — | 1000:1-1:50 |
| 531 | compound E | chloransulam | — | — | 500:1-1:500 | 450:1-1:450 | 450:1-1:450 | — | — | 1000:1-1:50 |
| 532 | compound E | diclosulam | — | — | 500:1-1:500 | 450:1-1:450 | 450:1-1:450 | — | — | 1000:1-1:50 |
| 533 | compound E | flumetsulam | — | — | 500:1-1:500 | 450:1-1:450 | 450:1-1:450 | — | — | 1000:1-1:50 |
| 534 | compound E | diuron | — | — | 500:1-1:500 | 450:1-1:450 | 450:1-1:450 | — | — | 1000:1-1:50 |
| 535 | compound E | metribuzin | — | — | 500:1-1:500 | 450:1-1:450 | 450:1-1:450 | — | — | 1000:1-1:50 |
| 536 | compound E | hexazinone | — | — | 500:1-1:500 | 450:1-1:450 | 450:1-1:450 | — | — | 1000:1-1:50 |
| 537 | compound E | mesotrione | — | — | 500:1-1:500 | 450:1-1:450 | 450:1-1:450 | — | — | 1000:1-1:50 |
| 538 | compound E | ametryn | — | — | 500:1-1:500 | 450:1-1:450 | 450:1-1:450 | — | — | 1000:1-1:50 |
| 539 | compound E | terbuthylazine | — | — | 500:1-1:500 | 450:1-1:450 | 450:1-1:450 | — | — | 1000:1-1:50 |
| 540 | compound E | metazachlor | — | — | 500:1-1:500 | 450:1-1:450 | 450:1-1:450 | — | — | 1000:1-1:50 |
| 541 | compound E | terbuthiuron | — | — | 500:1-1:500 | 450:1-1:450 | 450:1-1:450 | — | — | 1000:1-1:50 |
| 542 | compound E | clomazone | — | — | 500:1-1:500 | 450:1-1:450 | 450:1-1:450 | — | — | 1000:1-1:50 |
| 543 | compound E | hexazinone | diuron | — | 500:1-1:500 | 450:1-1:450 | 450:1-1:450 | 450:1-1:450 | — | 1000:1-1:50 |
| 544 | compound E | isoxaflutole | — | — | 500:1-1:500 | 450:1-1:450 | 450:1-1:450 | — | — | 1000:1-1:50 |
| 545 | compound E | atrazine | dicamba | — | 500:1-1:500 | 450:1-1:450 | 450:1-1:450 | 450:1-1:450 | — | 1000:1-1:50 |
| 546 | compound E | pendimethalin | dicamba | — | 500:1-1:500 | 450:1-1:450 | 450:1-1:450 | 450:1-1:450 | — | 1000:1-1:50 |
| 547 | compound E | flumioxazin | dicamba | — | 500:1-1:500 | 450:1-1:450 | 450:1-1:450 | 450:1-1:450 | — | 1000:1-1:50 |
| 548 | compound E | sulfentrazone | dicamba | — | 500:1-1:500 | 450:1-1:450 | 450:1-1:450 | 450:1-1:450 | — | 1000:1-1:50 |
| 549 | compound E | imazaquin | dicamba | — | 500:1-1:500 | 450:1-1:450 | 450:1-1:450 | 450:1-1:450 | — | 1000:1-1:50 |
| 550 | compound E | imazapic | dicamba | — | 500:1-1:500 | 450:1-1:450 | 450:1-1:450 | 450:1-1:450 | — | 1000:1-1:50 |
| 551 | compound E | imazapic | imazapyr | dicamba | 500:1-1:500 | 450:1-1:450 | 450:1-1:450 | 450:1-1:450 | 450:1-1:450 | 1000:1-1:50 |
| 552 | compound E | flufenaceet | dicamba | — | 500:1-1:500 | 450:1-1:450 | 450:1-1:450 | 450:1-1:450 | — | 1000:1-1:50 |
| 553 | compound E | chloransulam | dicamba | — | 500:1-1:500 | 450:1-1:450 | 450:1-1:450 | 450:1-1:450 | — | 1000:1-1:50 |
| 554 | compound E | diclosulam | dicamba | — | 500:1-1:500 | 450:1-1:450 | 450:1-1:450 | 450:1-1:450 | — | 1000:1-1:50 |
| 555 | compound E | flumetsulam | dicamba | — | 500:1-1:500 | 450:1-1:450 | 450:1-1:450 | 450:1-1:450 | — | 1000:1-1:50 |
| 556 | compound E | diuron | dicamba | — | 500:1-1:500 | 450:1-1:450 | 450:1-1:450 | 450:1-1:450 | — | 1000:1-1:50 |
| 557 | compound E | metribuzin | dicamba | — | 500:1-1:500 | 450:1-1:450 | 450:1-1:450 | 450:1-1:450 | — | 1000:1-1:50 |
| 558 | compound E | hexazinone | dicamba | — | 500:1-1:500 | 450:1-1:450 | 450:1-1:450 | 450:1-1:450 | — | 1000:1-1:50 |
| 559 | compound E | mesotrione | dicamba | — | 500:1-1:500 | 450:1-1:450 | 450:1-1:450 | 450:1-1:450 | — | 1000:1-1:50 |
| 560 | compound E | ametryn | dicamba | — | 500:1-1:500 | 450:1-1:450 | 450:1-1:450 | 450:1-1:450 | — | 1000:1-1:50 |
| 561 | compound E | terbuthylazine | dicamba | — | 500:1-1:500 | 450:1-1:450 | 450:1-1:450 | 450:1-1:450 | — | 1000:1-1:50 |
| 562 | compound E | metazachlor | dicamba | — | 500:1-1:500 | 450:1-1:450 | 450:1-1:450 | 450:1-1:450 | — | 1000:1-1:50 |
| 563 | compound E | terbuthiuron | dicamba | — | 500:1-1:500 | 450:1-1:450 | 450:1-1:450 | 450:1-1:450 | — | 1000:1-1:50 |
| 564 | compound E | clomazone | dicamba | — | 500:1-1:500 | 450:1-1:450 | 450:1-1:450 | 450:1-1:450 | — | 1000:1-1:50 |
| 565 | compound E | hexazinone | diuron | dicamba | 500:1-1:500 | 450:1-1:450 | 450:1-1:450 | 450:1-1:450 | 450:1-1:450 | 1000:1-1:50 |
| 566 | compound E | isoxaflutole | dicamba | — | 500:1-1:500 | 450:1-1:450 | 450:1-1:450 | 450:1-1:450 | — | 1000:1-1:50 |
| 567 | sulfentrazone | — | — | — | 500:1-1:500 | — | — | — | — | 1000:1-1:50 |
| 568 | sulfentrazone | dmta-P | — | — | 500:1-1:500 | 450:1-1:450 | 450:1-1:450 | — | — | 1000:1-1:50 |
| 569 | sulfentrazone | dmta-P | atrazine | dicamba | 500:1-1:500 | 450:1-1:450 | 450:1-1:450 | 450:1-1:450 | 450:1-1:450 | 1000:1-1:50 |
| 570 | sulfentrazone | imazethapyr | — | — | 500:1-1:500 | 450:1-1:450 | 450:1-1:450 | — | — | 1000:1-1:50 |
| 571 | sulfentrazone | dicamba | — | — | 500:1-1:500 | 450:1-1:450 | 450:1-1:450 | — | — | 1000:1-1:50 |
| 572 | sulfentrazone | atrazine | — | — | 500:1-1:500 | 450:1-1:450 | 450:1-1:450 | — | — | 1000:1-1:50 |
| 573 | sulfentrazone | pendimethalin | — | — | 500:1-1:500 | 450:1-1:450 | 450:1-1:450 | — | — | 1000:1-1:50 |
| 574 | sulfentrazone | flumioxazin | — | — | 500:1-1:500 | 450:1-1:450 | 450:1-1:450 | — | — | 1000:1-1:50 |
| 575 | sulfentrazone | imazaquin | — | — | 500:1-1:500 | 450:1-1:450 | 450:1-1:450 | — | — | 1000:1-1:50 |
| 576 | sulfentrazone | imazapic | — | — | 500:1-1:500 | 450:1-1:450 | 450:1-1:450 | — | — | 1000:1-1:50 |
| 577 | sulfentrazone | imazapic | imazapyr | — | 500:1-1:500 | 450:1-1:450 | 450:1-1:450 | 450:1-1:450 | — | 1000:1-1:50 |
| 578 | sulfentrazone | flufenaceet | — | — | 500:1-1:500 | 450:1-1:450 | 450:1-1:450 | — | — | 1000:1-1:50 |
| 579 | sulfentrazone | chloransulam | — | — | 500:1-1:500 | 450:1-1:450 | 450:1-1:450 | — | — | 1000:1-1:50 |
| 580 | sulfentrazone | diclosulam | — | — | 500:1-1:500 | 450:1-1:450 | 450:1-1:450 | — | — | 1000:1-1:50 |
| 581 | sulfentrazone | flumetsulam | — | — | 500:1-1:500 | 450:1-1:450 | 450:1-1:450 | — | — | 1000:1-1:50 |
| 582 | sulfentrazone | diuron | — | — | 500:1-1:500 | 450:1-1:450 | 450:1-1:450 | — | — | 1000:1-1:50 |
| 583 | sulfentrazone | metribuzin | — | — | 500:1-1:500 | 450:1-1:450 | 450:1-1:450 | — | — | 1000:1-1:50 |
| 584 | sulfentrazone | hexazinone | — | — | 500:1-1:500 | 450:1-1:450 | 450:1-1:450 | — | — | 1000:1-1:50 |
| 585 | sulfentrazone | mesotrione | — | — | 500:1-1:500 | 450:1-1:450 | 450:1-1:450 | — | — | 1000:1-1:50 |
| 586 | sulfentrazone | ametryn | — | — | 500:1-1:500 | 450:1-1:450 | 450:1-1:450 | — | — | 1000:1-1:50 |
| 587 | sulfentrazone | terbuthylazine | — | — | 500:1-1:500 | 450:1-1:450 | 450:1-1:450 | — | — | 1000:1-1:50 |
| 588 | sulfentrazone | metazachlor | — | — | 500:1-1:500 | 450:1-1:450 | 450:1-1:450 | — | — | 1000:1-1:50 |
| 589 | sulfentrazone | terbuthiuron | — | — | 500:1-1:500 | 450:1-1:450 | 450:1-1:450 | — | — | 1000:1-1:50 |
| 590 | sulfentrazone | clomazone | — | — | 500:1-1:500 | 450:1-1:450 | 450:1-1:450 | — | — | 1000:1-1:50 |
| 591 | sulfentrazone | hexazinone | diuron | — | 500:1-1:500 | 450:1-1:450 | 450:1-1:450 | 450:1-1:450 | — | 1000:1-1:50 |
| 592 | sulfentrazone | isoxaflutole | — | — | 500:1-1:500 | 450:1-1:450 | 450:1-1:450 | — | — | 1000:1-1:50 |

| No. | Herbicide C1 | Herbicide C2 | Herbicide C3 | Herbicide C4 | B:C* w/w | B:C1 | B:C2 | B:C3 | B:C4 | A:(B + C)* w/w |
|---|---|---|---|---|---|---|---|---|---|---|
| 593 | sulfentrazone | atrazine | dicamba | — | 500:1-1:500 | 450:1-1:450 | 450:1-1:450 | 450:1-1:450 | — | 1000:1-1:50 |
| 594 | sulfentrazone | pendimethalin | dicamba | — | 500:1-1:500 | 450:1-1:450 | 450:1-1:450 | 450:1-1:450 | — | 1000:1-1:50 |
| 595 | sulfentrazone | flumioxazin | dicamba | — | 500:1-1:500 | 450:1-1:450 | 450:1-1:450 | 450:1-1:450 | — | 1000:1-1:50 |
| 596 | sulfentrazone | imazaquin | dicamba | — | 500:1-1:500 | 450:1-1:450 | 450:1-1:450 | 450:1-1:450 | — | 1000:1-1:50 |
| 597 | sulfentrazone | imazapic | dicamba | — | 500:1-1:500 | 450:1-1:450 | 450:1-1:450 | 450:1-1:450 | — | 1000:1-1:50 |
| 598 | sulfentrazone | imazapic | imazapyr | dicamba | 500:1-1:500 | 450:1-1:450 | 450:1-1:450 | 450:1-1:450 | 450:1-1:450 | 1000:1-1:50 |
| 599 | sulfentrazone | flufenaceet | dicamba | — | 500:1-1:500 | 450:1-1:450 | 450:1-1:450 | 450:1-1:450 | — | 1000:1-1:50 |
| 600 | sulfentrazone | chloransulam | dicamba | — | 500:1-1:500 | 450:1-1:450 | 450:1-1:450 | 450:1-1:450 | — | 1000:1-1:50 |
| 601 | sulfentrazone | diclosulam | dicamba | — | 500:1-1:500 | 450:1-1:450 | 450:1-1:450 | 450:1-1:450 | — | 1000:1-1:50 |
| 602 | sulfentrazone | flumetsulam | dicamba | — | 500:1-1:500 | 450:1-1:450 | 450:1-1:450 | 450:1-1:450 | — | 1000:1-1:50 |
| 603 | sulfentrazone | diuron | dicamba | — | 500:1-1:500 | 450:1-1:450 | 450:1-1:450 | 450:1-1:450 | — | 1000:1-1:50 |
| 604 | sulfentrazone | metribuzin | dicamba | — | 500:1-1:500 | 450:1-1:450 | 450:1-1:450 | 450:1-1:450 | — | 1000:1-1:50 |
| 605 | sulfentrazone | hexazinone | dicamba | — | 500:1-1:500 | 450:1-1:450 | 450:1-1:450 | 450:1-1:450 | — | 1000:1-1:50 |
| 606 | sulfentrazone | mesotrione | dicamba | — | 500:1-1:500 | 450:1-1:450 | 450:1-1:450 | 450:1-1:450 | — | 1000:1-1:50 |
| 607 | sulfentrazone | ametryn | dicamba | — | 500:1-1:500 | 450:1-1:450 | 450:1-1:450 | 450:1-1:450 | — | 1000:1-1:50 |
| 608 | sulfentrazone | terbuthylazine | dicamba | — | 500:1-1:500 | 450:1-1:450 | 450:1-1:450 | 450:1-1:450 | — | 1000:1-1:50 |
| 609 | sulfentrazone | metazachlor | dicamba | — | 500:1-1:500 | 450:1-1:450 | 450:1-1:450 | 450:1-1:450 | — | 1000:1-1:50 |
| 610 | sulfentrazone | terbuthiuron | dicamba | — | 500:1-1:500 | 450:1-1:450 | 450:1-1:450 | 450:1-1:450 | — | 1000:1-1:50 |
| 611 | sulfentrazone | clomazone | dicamba | — | 500:1-1:500 | 450:1-1:450 | 450:1-1:450 | 450:1-1:450 | — | 1000:1-1:50 |
| 612 | sulfentrazone | hexazinone | diuron | dicamba | 500:1-1:500 | 450:1-1:450 | 450:1-1:450 | 450:1-1:450 | 450:1-1:450 | 1000:1-1:50 |
| 613 | sulfentrazone | isoxaflutole | dicamba | — | 500:1-1:500 | 450:1-1:450 | 450:1-1:450 | 450:1-1:450 | — | 1000:1-1:50 |
| 614 | flumioxazin | — | — | — | 500:1-1:500 | — | — | — | — | 1000:1-1:10 |
| 615 | flumioxazin | dmta-P | — | — | 500:1-1:500 | 450:1-1:450 | 450:1-1:450 | — | — | 1000:1-1:50 |
| 616 | flumioxazin | dmta-P | atrazine | dicamba | 500:1-1:500 | 450:1-1:450 | 450:1-1:450 | 450:1-1:450 | 450:1-1:450 | 1000:1-1:50 |
| 617 | flumioxazin | imazethapyr | — | — | 500:1-1:500 | 450:1-1:450 | 450:1-1:450 | — | — | 1000:1-1:50 |
| 618 | flumioxazin | dicamba | — | — | 500:1-1:500 | 450:1-1:450 | 450:1-1:450 | — | — | 1000:1-1:50 |
| 619 | flumioxazin | atrazine | — | — | 500:1-1:500 | 450:1-1:450 | 450:1-1:450 | — | — | 1000:1-1:50 |
| 620 | flumioxazin | pendimethalin | — | — | 500:1-1:500 | 450:1-1:450 | 450:1-1:450 | — | — | 1000:1-1:50 |
| 621 | flumioxazin | imazaquin | — | — | 500:1-1:500 | 450:1-1:450 | 450:1-1:450 | — | — | 1000:1-1:50 |
| 622 | flumioxazin | imazapic | — | — | 500:1-1:500 | 450:1-1:450 | 450:1-1:450 | — | — | 1000:1-1:50 |
| 623 | flumioxazin | imazapic | imazapyr | — | 500:1-1:500 | 450:1-1:450 | 450:1-1:450 | 450:1-1:450 | — | 1000:1-1:50 |
| 624 | flumioxazin | flufenaceet | — | — | 500:1-1:500 | 450:1-1:450 | 450:1-1:450 | — | — | 1000:1-1:50 |
| 625 | flumioxazin | chloransulam | — | — | 500:1-1:500 | 450:1-1:450 | 450:1-1:450 | — | — | 1000:1-1:50 |
| 626 | flumioxazin | diclosulam | — | — | 500:1-1:500 | 450:1-1:450 | 450:1-1:450 | — | — | 1000:1-1:50 |
| 627 | flumioxazin | flumetsulam | — | — | 500:1-1:500 | 450:1-1:450 | 450:1-1:450 | — | — | 1000:1-1:50 |
| 628 | flumioxazin | diuron | — | — | 500:1-1:500 | 450:1-1:450 | 450:1-1:450 | — | — | 1000:1-1:50 |
| 629 | flumioxazin | metribuzin | — | — | 500:1-1:500 | 450:1-1:450 | 450:1-1:450 | — | — | 1000:1-1:50 |
| 630 | flumioxazin | hexazinone | — | — | 500:1-1:500 | 450:1-1:450 | 450:1-1:450 | — | — | 1000:1-1:50 |
| 631 | flumioxazin | mesotrione | — | — | 500:1-1:500 | 450:1-1:450 | 450:1-1:450 | — | — | 1000:1-1:50 |
| 632 | flumioxazin | ametryn | — | — | 500:1-1:500 | 450:1-1:450 | 450:1-1:450 | — | — | 1000:1-1:50 |
| 633 | flumioxazin | terbuthylazine | — | — | 500:1-1:500 | 450:1-1:450 | 450:1-1:450 | — | — | 1000:1-1:50 |
| 634 | flumioxazin | metazachlor | — | — | 500:1-1:500 | 450:1-1:450 | 450:1-1:450 | — | — | 1000:1-1:50 |
| 635 | flumioxazin | terbuthiuron | — | — | 500:1-1:500 | 450:1-1:450 | 450:1-1:450 | — | — | 1000:1-1:50 |
| 636 | flumioxazin | clomazone | — | — | 500:1-1:500 | 450:1-1:450 | 450:1-1:450 | — | — | 1000:1-1:50 |
| 637 | flumioxazin | hexazinone | diuron | — | 500:1-1:500 | 450:1-1:450 | 450:1-1:450 | 450:1-1:450 | — | 1000:1-1:50 |
| 638 | flumioxazin | isoxaflutole | — | — | 500:1-1:500 | 450:1-1:450 | 450:1-1:450 | — | — | 1000:1-1:50 |
| 639 | flumioxazin | atrazine | dicamba | — | 500:1-1:500 | 450:1-1:450 | 450:1-1:450 | 450:1-1:450 | — | 1000:1-1:50 |
| 640 | flumioxazin | pendimethalin | dicamba | — | 500:1-1:500 | 450:1-1:450 | 450:1-1:450 | 450:1-1:450 | — | 1000:1-1:50 |
| 641 | flumioxazin | imazaquin | dicamba | — | 500:1-1:500 | 450:1-1:450 | 450:1-1:450 | 450:1-1:450 | — | 1000:1-1:50 |
| 642 | flumioxazin | imazapic | dicamba | — | 500:1-1:500 | 450:1-1:450 | 450:1-1:450 | 450:1-1:450 | — | 1000:1-1:50 |
| 643 | flumioxazin | imazapic | imazapyr | dicamba | 500:1-1:500 | 450:1-1:450 | 450:1-1:450 | 450:1-1:450 | 450:1-1:450 | 1000:1-1:50 |
| 644 | flumioxazin | flufenaceet | dicamba | — | 500:1-1:500 | 450:1-1:450 | 450:1-1:450 | 450:1-1:450 | — | 1000:1-1:50 |
| 645 | flumioxazin | chloransulam | dicamba | — | 500:1-1:500 | 450:1-1:450 | 450:1-1:450 | 450:1-1:450 | — | 1000:1-1:50 |
| 646 | flumioxazin | diclosulam | dicamba | — | 500:1-1:500 | 450:1-1:450 | 450:1-1:450 | 450:1-1:450 | — | 1000:1-1:50 |
| 647 | flumioxazin | flumetsulam | dicamba | — | 500:1-1:500 | 450:1-1:450 | 450:1-1:450 | 450:1-1:450 | — | 1000:1-1:50 |
| 648 | flumioxazin | diuron | dicamba | — | 500:1-1:500 | 450:1-1:450 | 450:1-1:450 | 450:1-1:450 | — | 1000:1-1:50 |
| 649 | flumioxazin | metribuzin | dicamba | — | 500:1-1:500 | 450:1-1:450 | 450:1-1:450 | 450:1-1:450 | — | 1000:1-1:50 |
| 650 | flumioxazin | hexazinone | dicamba | — | 500:1-1:500 | 450:1-1:450 | 450:1-1:450 | 450:1-1:450 | — | 1000:1-1:50 |
| 651 | flumioxazin | mesotrione | dicamba | — | 500:1-1:500 | 450:1-1:450 | 450:1-1:450 | 450:1-1:450 | — | 1000:1-1:50 |
| 652 | flumioxazin | ametryn | dicamba | — | 500:1-1:500 | 450:1-1:450 | 450:1-1:450 | 450:1-1:450 | — | 1000:1-1:50 |
| 653 | flumioxazin | terbuthylazine | dicamba | — | 500:1-1:500 | 450:1-1:450 | 450:1-1:450 | 450:1-1:450 | — | 1000:1-1:50 |
| 654 | flumioxazin | metazachlor | dicamba | — | 500:1-1:500 | 450:1-1:450 | 450:1-1:450 | 450:1-1:450 | — | 1000:1-1:50 |
| 655 | flumioxazin | terbuthiuron | dicamba | — | 500:1-1:500 | 450:1-1:450 | 450:1-1:450 | 450:1-1:450 | — | 1000:1-1:50 |
| 656 | flumioxazin | clomazone | dicamba | — | 500:1-1:500 | 450:1-1:450 | 450:1-1:450 | 450:1-1:450 | — | 1000:1-1:50 |

-continued

| No. | Herbicide C1 | Herbicide C2 | Herbicide C3 | Herbicide C4 | B:C* w/w | B:C1 | B:C2 | B:C3 | B:C4 | A:(B + C)* w/w |
|---|---|---|---|---|---|---|---|---|---|---|
| 657 | flumioxazin | hexazinone | diuron | dicamba | 500:1-1:500 | 450:1-1:450 | 450:1-1:450 | 450:1-1:450 | 450:1-1:450 | 1000:1-1:50 |
| 658 | flumioxazin | isoxaflutole | dicamba | — | 500:1-1:500 | 450:1-1:450 | 450:1-1:450 | 450:1-1:450 | — | 1000:1-1:50 |

C = C1 + C2 + C3 dmta-P = dimethenamid-P compound A:

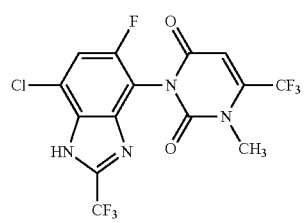

(A)

compound B:

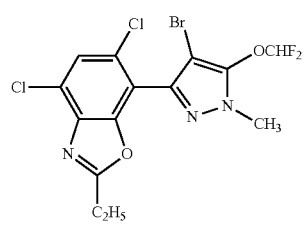

(B)

compound C:

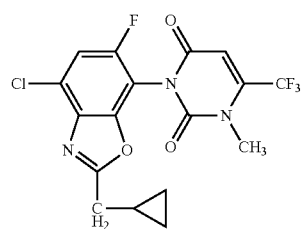

(C)

compound D:

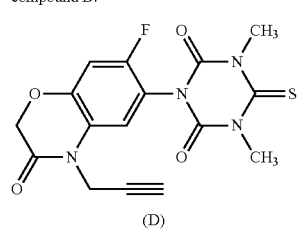

(D)

compound E:

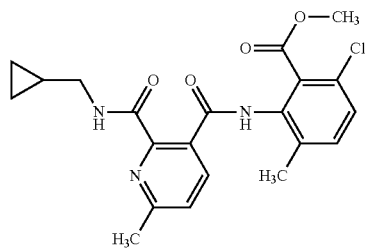

(E)

continuation 2 of table 1:

Mixtures 659 to 1044: These mixtures correspond to mixtures 273 to 658, wherein glyphosate has been replaced by gluphosinate or a salt thereof.

The compositions of the invention may also comprise, as a component d), one or more safeners. Safeners, also termed as herbicide safeners are organic compounds which in some cases lead to better crop plant compatibility when applied jointly with specifically acting herbicides. Some safeners are themselves herbicidally active. In these cases, the safeners act as antidote or antagonist in the crop plants and thus reduce or even prevent damage to the crop plants. However, in the compositions of the present invention, safeners are generally not required. Therefore, a preferred embodiment of the invention relates to compositions which contain no safener or virtually no safener (i.e. less than 1% by weight, based on the total amount of herbicide A and herbicide B).

Suitable safeners, which can be used in the compositions according to the present invention are known in the art, e.g. from The Compendium of Pesticide Common Names (http://www.alanwood.net/pesticides/);

Farm Chemicals Handbook 2000 Vol. 86, Meister Publishing Company, 2000;

B. Hock, C. Fedtke, R. R. Schmidt, Herbizide, Georg Thieme Verlag, Stuttgart 1995;

W. H. Ahrens, Herbicide Handbook, 7$^{th}$ Edition, Weed Science Society of America, 1994; and K. K. Hatzios, Herbicide Handbook, Supplement to 7$^{th}$ Edition, Weed Science Society of America, 1998.

Safeners include benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine, 4-(dichloroacetyl)-1-oxa-4-azaspiro[4.5]decane and oxabetrinil, as well as thereof agriculturally acceptable salts and, provided they have a carboxyl group, their agriculturally acceptable derivatives. 2,2,5-Trimethyl-3-(dichloroacetyl)-1,3-oxazolidine [CAS No. 52836-31-4] is also known under the name R-29148.4-(Dichloroacetyl)-1-oxa-4-azaspiro[4.5]decane [CAS No. 71526-07-03] is also known under the names AD-67 and MON 4660.

As safener, the compositions according to the invention particularly preferably comprise at least one of the compounds selected from the group of benoxacor, cloquintocet, cyprosulfamide, dichlormid, fenchlorazole, fenclorim, fluxofenim, furilazole, isoxadifen, mefenpyr, naphthalic anhydride, 2,2,5-trimethyl-3-(dichloroacetyl)-1,3-oxazolidine, and 4-(dichloroacetyl)-1-oxa-4-azaspiro[4.5]decane and oxabetrinil; and the agriculturally acceptable salt thereof and, in the case of compounds having a COOH group, an agriculturally acceptable derivative as defined below.

A preferred embodiment of the invention relates to compositions which contain no safener or virtually no safener (i.e. less than 1% by weight, based on the total amount of the at least one herbicide A and herbicide B and optionally herbicide C) is applied.

The compositions of the present invention are suitable for controlling a large number of harmful plants, including monocotyledonous weeds, in particular annual weeds such as gramineous weeds (grasses) including *Echinochloa* species such as barnyardgrass (*Echinochloa crusgalli* var. *crusgalli*), *Digitaria* species such as crabgrass (*Digitaria sanguinalis*), *Setaria* species such as green foxtail (*Setaria viridis*) and giant foxtail (*Setaria faberii*), *Sorghum* species such as johnsongrass (*Sorghum halepense* Pers.), *Avena* species such as wild oats (*Avena fatua*), *Cenchrus* species such as *Cenchrus echinatus*, *Bromus* species, *Lolium* species, *Phalaris* species, *Eriochloa* species, *Panicum* species, *Brachiaria* species, annual bluegrass (*Poa annua*), black-grass (*Alopecurus myosuroides*), *Aegilops cylindrica*, *Agropyron repens*, *Apera spica-venti*, *Eleusine indica*, *Cynodon dactylon* and the like.

The compositions of the present invention are also suitable for controlling a large number of dicotyledonous weeds, in particular broad leaf weeds including *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, *Cassia* species, *Commelina* species, *Datura* species, *Euphorbia* species, *Geranium* species, *Galinsoga* species, morningglory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp sesbania (*Sesbania exaltata* Cory), *Anoda cristata*, *Bidens pilosa*, *Brassica kaber*, *Capsella bursa-pastoris*, *Centaurea cyanus*, *Galeopsis tetrahit*, *Galium aparine*, *Helianthus annuus*, *Desmodium tortuosum*, *Kochia scoparia*, *Mercurialis annua*, *Myosotis arvensis*, *Papaver rhoeas*, *Raphanus raphanistrum*, *Salsola kali*, *Sinapis arvensis*, *Sonchus arvensis*, *Thlaspi arvense*, *Tagetes minuta*, *Richardia brasiliensis*, and the like.

The compositions of the present invention are also suitable for controlling a large number of annual and perennial sedge weeds including *cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

The compositions of the present invention are particularly useful in so-called burndown programs, in particular pre-plant burndown programs. i.e. the compositions of the invention are applied to a locus where crops will be planted before planting or emergence of the crop.

Therefore, the present invention also relates to a method for burndown treatment of undesirable vegetation in crops, comprising applying a) at least one herbicide A selected from glyphosate, glufosinate and their salts, and b) a herbicide B which is 3-[5-(difluoromethoxy)-1-methyl-3-(trifluoromethyl)pyrazol-4-ylmethylsulfonyl]-4,5-dihydro-5,5-dimethyl-1,2-oxazole, to a locus where crops will be planted before planting or emergence of the crop.

In the burndown treatment of the present invention, additionally at least one further herbicide C from the groups C.1 to C.8 as defined above can be applied together with the herbicides A and B. The term to apply together includes simultaneous and successive application. Likewise, applying the composition does not necessarily mean that the compounds A, B and optionally C must be applied as a single formulation or as a tank mix. Rather, the composition includes separate formulations of herbicides A and B and optionally C, which can be applied as a single tank-mix or via separate application means. In any case, the at least one herbicide A, the herbicide B and the one or more optional herbicides C can be applied simultaneously or in succession.

However, it is also possible to apply the herbicide C in the burndown treatment after seeding or even after emergence of the crop.

Though possible, it is not necessary to formulate the herbicides A, B and optionally C in a single formulation. Usually the herbicides A and B and optionally C are combined as a tank-mix prior to application. It is however also possible to provide a premix of the herbicide B and the optional herbicide C and to combine this premix with the at least one herbicide A.

The compositions of the present invention can be applied in conventional manner by using techniques as skilled person is familiar with. Suitable techniques include spraying, atomizing, dusting, spreading or watering. The type of application depends on the intended purpose in a well known manner; in any case, they should ensure the finest possible distribution of the active ingredients according to the invention.

The compositions are applied to locus mainly by spraying, in particular foliar spraying of an aqueous dilution of the active ingredients of the composition. Application can be carried out by customary spraying techniques using, for example, water as carrier and spray liquor rates of from about 10 to 2000 l/ha or 50 to 1000 l/ha (for example from 100 to 500 l/ha). Application of the herbicidal compositions by the low-volume and the ultra-low-volume method is possible, as is their application in the form of microgranules.

If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

The compositions can be applied pre- or post-emergence, i.e. before, during and/or after emergence of the undesirable plants.

When the compositions are used in burndown programs, they can be applied prior to seeding (planting) or after seeding (or planting) of the crop plants but before the emergence of the crop plants. The compositions are preferably applied prior to seeding of the crop plants. For burndown, the compositions will generally be applied a date up to 9 month, frequently up to 6 month, preferably up to 4 month prior to planting the crop. The burndown application can be done at a date up to 1 day prior to emergence of the crop plant and is preferably done at a date prior to seeding/planting of the crop plant, preferably at a date of at least one day, preferably at least 2 days and in particular at least one 4 days prior to planting or from 6 month to 1 day prior emergence, in particular from 4 month to 2 days prior emergence and more preferably from 4 month to 4 days prior emergence. It is, of course, possible to repeat the burndown application once or more, e.g. once, twice, three times, four times or five times within that time frame.

In the burndown treatment according to the present invention, the at least one herbicide A and the herbicide B are applied to the field of the crop plants prior to the emergence of the crop plants, in particular prior to seeding within the above time frame. In a specific embodiment of this burndown treatment, the one or more herbicides C are also applied within this time frame. In this specific embodiment is also possible to additionally apply the one or more herbicides C and optionally further pyroxasulfone after the planting or seeding or even after emergence of the crop, preferably at a date until 12 weeks after emergence of the crop. In another specific embodiment of this burndown treatment, the one or more herbicides C and optionally further pyroxasulfone are only applied after the planting or seeding or even after emergence of the crop, preferably at a date until 12 weeks after emergence of the crop.

It is a particular benefit of the compositions according to the invention that they have a very good post-emergence herbicide activity, i.e. they show a good herbicidal activity against emerged undesirable plants. Thus, in a preferred embodiment of invention, the compositions are applied post-emergence, i.e. during and/or after, the emergence of the undesirable plants. It is particularly advantageous to apply the mixtures according to the invention post emergent when the undesirable plant starts with leaf development up to flowering. The compositions are particularly useful for controlling undesirable vegetation which has already developed to a state, which is difficult to control with conventional burndown compositions, i.e. when the individual weed is taller than 10 cm (4 inches) or even taller than 15 cm (6 inches) and/or for heavy weed populations.

In the case of a post-emergence treatment of the plants, the herbicidal mixtures or compositions according to the invention are preferably applied by foliar application.

Application may be effected, for example, by usual spraying techniques with water as the carrier, using amounts of spray mixture of usually from 10 to 2000 l/ha, in particular 50 to 1000 l/ha.

The required application rate of the composition of the pure active compounds, i.e. of pyroxasulfone, herbicide A and optionally herbicide C depends on the density of the undesired vegetation, on the development stage of the plants, on the climatic conditions of the location where the composition is used and on the application method. In general, the application rate of the composition (total amount of pyroxasulfone, herbicide A and optional further actives) is from 55 to 6000 g/ha, preferably from 100 to 5000 g/ha, from 200 to 4000 g/ha, and more preferably from 300 to 3000 g/ha of active ingredient (a.i.).

The rate of application of herbicide A is usually from 50 g/ha to 3000 g/ha and preferably in the range from 100 g/ha to 2000 g/ha or from 200 g/ha to 1500 g/ha of active substance (a.i.).

The rate of application of pyroxasulfone is usually from 1 g/ha to 500 g/ha and preferably in the range from 5 g/ha to 400 g/ha or from 20 g/ha to 300 g/ha of active substance (a.i.).

The application rates of the herbicide C (total amount of herbicide C) are generally in the range from 0.5 g/ha to 5000 g/ha and preferably in the range from 1 g/ha to 4000 g/ha or from 2 g/ha to 3000 g/ha of active substance.

The application rates of the herbicide C.1 (total amount of herbicide C.1) are generally in the range from 0.5 g/ha to 1000 g/ha and preferably in the range from 1 g/ha to 500 g/ha or from 2 g/ha to 250 g/ha of active substance. The application rates of the herbicide C.1.1 (total amount of herbicide C.1.1) are preferably in the range from 1 g/ha to 1000 g/ha and more preferably in the range from 5 g/ha to 500 g/ha or from 10 g/ha to 250 g/ha of active substance.

The application rates of the herbicide C.2 (total amount of herbicide C.2) are generally in the range from 1 g/ha to 5000 g/ha and preferably in the range from 5 g/ha to 2500 g/ha or from 10 g/ha to 2000 g/ha of active substance. The application rates of the herbicide C.2.1 (total amount of herbicide C.2.1) are preferably in the range from 1 g/ha to 500 g/ha and more preferably in the range from 5 g/ha to 500 g/ha or from 10 g/ha to 250 g/ha of active substance. The application rates of the herbicides C.2.2 (total amount of herbicide C.2.2) is preferably 1 to 1000 g/ha, more preferably 10 to 750 g/ha, most preferably 20 to 500 g/ha, of active substance (a.s.).

The application rates of the herbicide C.3 (total amount of herbicide C.3) are generally in the range from 1 g/ha to 3000 g/ha and preferably in the range from 5 g/ha to 2000 g/ha or from 10 g/ha to 1500 g/ha of active substance.

The application rates of the herbicide C.5 (total amount of herbicide C.5) are generally in the range from 5 g/ha to 4000 g/ha and preferably in the range from 10 g/ha to 2500 g/ha or from 20 g/ha to 1000 g/ha of active substance. The rate of application of pyridinecarboxamide herbicides is preferably from 5 to 500 g/ha, more preferably 10 to 400 g/ha, in particular 20 to 250 g/ha, of active substance (a.s.).

The required application rates of the herbicide C.6 (total amount of herbicide C.6) are generally in the range from 10 g/ha to 5000 g/ha and preferably in the range from 20 g/ha to 4000 g/ha or from 50 g/ha to 3000 g/ha of active substance.

The application rates of the herbicide C.7 (total amount of herbicide C.7) are generally in the range from 10 g/ha to 4000 g/ha and preferably in the range from 50 g/ha to 3000 g/ha or from 100 g/ha to 2500 g/ha of active substance. The rate of application of the dinitroanilines is preferably from 10 g/ha to 4000 g/ha and more preferably in the range from 50 g/ha to 3000 g/ha or from 100 g/ha to 2500 g/ha of active substance (a.i.).

The application rates of the herbicide C.8 (total amount of herbicide C.8) are generally in the range from 10 g/ha to 5000 g/ha and preferably in the range from 20 g/ha to 4000 g/ha or from 50 g/ha to 3000 g/ha of active substance.

The application rates of the safener, if applied, are generally in the range from 1 g/ha to 5000 g/ha and preferably in the range from 2 g/ha to 5000 g/ha or from 5 g/ha to 5000 g/ha of active substance. Preferably no safener or virtually no safener is applied and thus the application rates are below 5 g/ha, in particular below 2 g/ha or below 1 g/ha.

The compositions according to the present invention are suitable for combating/controlling common harmful plants in fields, where useful plants shall be planted (i.e. in crops). The compositions of the present invention are generally suitable for burndown of undesired vegetation in fields of the following crops:

Grain crops, including e.g.
cereals (small grain crops) such as wheat (*Triticum aestivum*) and wheat like crops such as durum (*T. durum*), einkorn (*T. monococcum*), emmer (*T. dicoccon*) and spelt (*T. spelta*), rye (*Secale cereale*), triticale (*Tritiosecale*), barley (*Hordeum vulgare*);
maize (corn; *Zea mays*);
sorghum (e.g. *Sorghum bicolour*);
rice (*Olyza* spp. such as *Oryza sativa* and *Oryza glaberrima*); and
sugar cane;

Legumes (Fabaceae), including e.g. soybeans (*Glycine max*), peanuts (*Arachis hypogaea* and pulse crops such as peas including *Pisum sativum*, pigeon pea and cowpea, beans including broad beans (*Vicia faba*), *Vigna* spp., and *Phaseolus* spp. and lentils (lens culinaris var.);

brassicaceae, including e.g. canola (*Brassica napus*), oilseed rape (OSR, *Brassica napus*), cabbage (*B. oleracea* var.), mustard such as *B. juncea, B. campestris, B. narinosa, B. nigra* and *B. tournefortii*; and turnip (*Brassica rapa* var.);

other broadleaf crops including e.g. sunflower, cotton, flax, linseed, sugarbeet, potato and tomato;

TNV-crops (TNV: trees, nuts and vine) including e.g. grapes, citrus, pomefruit, e.g. apple and pear, coffee, pistachio and oilpalm, stonefruit, e.g. peach, almond, walnut, olive, cherry, plum and apricot;

turf, pasture and rangeland;

onion and garlic;

bulb ornamentals such as tulips and *narcissus;* conifers and deciduous trees such as *pinus*, fir, oak, maple, dogwood, hawthorne, crabapple, and *rhamnus* (buckthorn); and garden ornamentals such as roses, *petunia*, marigold and snapdragon.

The compositions of the present invention are in particular suitable for burndown of undesired vegetation in fields of the following crop plants: small grain crops such as wheat, barley, rye, triticale and durum, rice, maize (corn), sugarcane, *sorghum*, soybean, pulse crops such as pea, bean and lentils, peanut, sunflower, sugarbeet, potato, cotton, *brassica* crops, such as oilseed rape, canola, mustard, cabbage and turnip, turf, pasture, rangeland, grapes, pomefruit, such as apple and pear, stonefruit, such as peach, almond, walnut, pecans, olive, cherry, plum and apricot, citrus, coffee, pistachio, garden ornamentals, such as roses, *petunia*, marigold, snap dragon, bulb ornamentals such as tulips and *narcissus*, conifers and deciduous trees such as *pinus*, fir, oak, maple, dogwood, hawthorne, crabapple and *rhamnus.*

The compositions of the present invention are most suitable for burndown of undesired vegetation in fields of the following crop plants: small grain crops such as wheat, barley, rye, triticale and durum, rice, maize, sugarcane, soybean, pulse crops such as pea, bean and lentils, peanut, sunflower, cotton, *brassica* crops, such as oilseed rape, canola, turf, pasture, rangeland, grapes, stonefruit, such as peach, almond, walnut, pecans, olive, cherry, plum and apricot, citrus and pistachio.

If not stated otherwise, the compositions of the invention are suitable for application in fields of any variety of the aforementioned crop plants.

The compositions according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding. Suitable are for example crop plants, preferably corn, wheat, sunflower, rice, canola, oilseed rape, soybeans, cotton and sugarcane, which are resistant or tolerant to glyphosate and/or glufosinate, crop plants which are resistant or tolerant to auxins such as dicamba, crop plants which are resistant or tolerant to HPPD inhibitors, crop plants which are resistant or tolerant to ALS inhibitors such as crop plants which are resistant or tolerant to imidazolinones, crop plants which are resistant or tolerant to PPO inhibitors or crop plants which, owing to introduction of the gene for Bt toxin by genetic modification, are resistant to attack by certain insects.

In a particular a specific embodiment, the compositions of the present inventions are used for controlling undesirable vegetation to crop plants, which are tolerant to herbicides, in particular in crop plants that are resistant or tolerant to glyphosate and/or glufosinate and which are stacked with further resistance or tolerance against at least one further herbicide, in particular at least one of the following herbicides: auxins such as dicamba, HPPD inhibitors, ALS inhibitors, in particular imidazolinones, PPO inhibitors.

In these herbicide resistant or tolerant crops, the compositions of the present invention can be used both for burndown and for control of undesired vegetation after emergence of the crops. Therefor, a particular embodiment of the invention relates to a method for controlling undesirable vegetation in herbicide resistant or tolerant crops, in particular in crop plants which are resistant or tolerant to glyphosate and/or glufosinate and which are optionally stacked with further resistance or tolerance against at least one further herbicide, in particular at least one of the following herbicides: auxins such as dicamba, HPPD inhibitors, ALS inhibitors, in particular imidazolinones, PPO inhibitors. In this particular embodiment, the compositions can be used for burndown but also for the control of undesirable vegetation after the crop plants.

In this particular method of the invention, the composition of the invention can be applied at least once prior to planting or emergence of the herbicide resistant or tolerant crop plant to achieve effective burndown of the undesirable vegetation and the composition can also be applied after emergence of the herbicide resistant or tolerant crop plants.

If the compositions of the present invention are used in crop plants, i.e. if they are applied in fields of the crop plants after emergence of the crops, application methods and application rates as described for burndown can be applied. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by). However such methods are generally not necessary and the compositions can be simply applied over the top (OTT).

For example, a composition comprising glyphosate and/or glufosinate or an agriculturally acceptable salt thereof, pyroxasulfone and an imidazolinone herbicide is particularly useful for burndown in fields, where a glyphosate tolerant crop having imidazolinone tolerance shall be planted such as maize, canola, wheat, soybeans or sunflower, all of which having glyphosate and/or glufosinate tolerance and imidazolinone tolerance. Such compositions are also particularly useful for burndown in fields where sugarcane shall be planted, the sugarcane being conventional sugarcane or sugarcane being tolerant to glyphosate or glufosinate optionally stacked with tolerance against imidazolinones. These compositions can also used for controlling undesirable vegetation in crops having glyphosate and/or glufosinate resistance stacked with imidazolinone resistance after emergence of the crop.

For example, a composition comprising glyphosate and/or glufosinate or an agriculturally acceptable salt thereof, pyroxasulfone and an auxin herbicide is particularly useful for burndown in fields both of conventional crops such as maize, canola, wheat, soybeans, sunflower and sugarcane and crops having glyphosate and/or glufosinate tolerance, optionally stacked with auxin tolerance. These compositions can also used for controlling undesirable vegetation in crops having glyphosate tolerance optionally stacked with auxin resistance after emergence of the crop.

For example, a composition comprising glyphosate and/or glufosinate or an agriculturally acceptable salt thereof, pyroxasulfone and an PPO inhibitor herbicide is particularly useful for burndown in fields both of conventional crops such as maize, wheat, soybeans, sunflower and sugarcane and crops having glyphosate and/or glufosinate tolerance, optionally stacked with PPO inhibitor tolerance.

For example, a composition comprising glyphosate and/or glufosinate or an agriculturally acceptable salt thereof, pyroxasulfone and an PPO inhibitor herbicide is particularly useful for burndown in fields both of conventional crops of maize and sugarcane and such crops having glyphosate and/or glufosinate tolerance, optionally stacked with further herbicide tolerance. These compositions can also used for controlling undesirable vegetation in such crops after emergence of the crop.

For example, a composition comprising glyphosate and/or glufosinate or an agriculturally acceptable salt thereof, pyroxasulfone and an HPPD inhibitor herbicide is particularly useful for burndown in fields both of conventional crops of small grain cereals and crops of small grain cereals having glyphosate and/or glufosinate tolerance, optionally stacked with further herbicide tolerance. These compositions can also used for controlling undesirable vegetation in such crops after emergence of the crop.

For example, a composition comprising glyphosate and/or glufosinate or an agriculturally acceptable salt thereof, pyroxasulfone and an PSII inhibitor herbicide of the group C.6.2, C.6.3 or C.6.8 is particularly useful for burndown in fields both of conventional crops of maize or sugarcane and crops of maize or sugarcane having glyphosate and/or glufosinate tolerance, optionally stacked with further herbicide tolerance. These compositions can also used for controlling undesirable vegetation in such crops after emergence of the crop.

For example, a composition comprising glyphosate and/or glufosinate or an agriculturally acceptable salt thereof, pyroxasulfone and an PSII inhibitor herbicide of the group C.6.1 is particularly useful for burndown in fields both of conventional crops of small grain cereals or sugarcane and crops of small grain cereals or sugarcane having glyphosate and/or glufosinate tolerance, optionally stacked with further herbicide tolerance. These compositions can also used for controlling undesirable vegetation in such crops after emergence of the crop.

For example, a composition comprising glyphosate and/or glufosinate or an agriculturally acceptable salt thereof, pyroxasulfone and a microtubulin inhibitor herbicide is particularly useful for burndown in fields both of conventional crops of small grain cereals, maize, soybean, sunflower or sugarcane and crops of small grain cereals, maize, soybean, sunflower or sugarcane having glyphosate and/or glufosinate tolerance, optionally stacked with further herbicide tolerance. These compositions can also used for controlling undesirable vegetation in such crops after emergence of the crop.

For example, a composition comprising glyphosate and/or glufosinate or an agriculturally acceptable salt thereof, pyroxasulfone and a VLCFA inhibitor herbicide is particularly useful for burndown in fields both of conventional crops of small grain cereals, maize, soybean, sunflower or sugarcane and crops of small grain cereals, maize, soybean, sunflower or sugarcane having glyphosate and/or glufosinate tolerance, optionally stacked with further herbicide tolerance. These compositions can also used for controlling undesirable vegetation in such crops after emergence of the crop.

The active ingredients used in the compositions of the present invention are usually available as pure substances and as formulations.

The formulations contain, besides the active ingredient or the composition, at least one organic or inorganic carrier material. The formulations may also contain, if desired, one or more surfactants and, if desired, one or more further auxiliaries customary for crop protection compositions.

The formulation may be in the form of a single package formulation containing both the at least one herbicide A and the herbicide B and optionally the one or more herbicides C together with liquid and/or solid carrier materials, and, if desired, one or more surfactants and, if desired, one or more further auxiliaries customary for crop protection compositions. The formulation may be in the form of a two or multi (e.g. three, four or five) package formulation, wherein one package contains a formulation of pyroxasulfone while the other package contains a formulation of the at least one herbicide A and optionally one or more further formulations contains the at least one herbicide C, wherein all formulations contain at least one carrier material, if desired, one or more surfactants and, if desired, one or more further auxiliaries customary for crop protection compositions. In the case of two or multi package formulations the formulation containing pyroxasulfone and the formulation containing the herbicide A and optionally the one or more formulations containing the one or more herbicides C are mixed prior to application. Preferably the mixing is performed as a tank mix, i.e. the formulations are mixed immediately prior or upon dilution with water.

In the formulations the active ingredients and optional further actives are present in suspended, emulsified or dissolved form. The formulation can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

Depending on the formulation type, they comprise one or more liquid or solid carriers, if appropriate surfactants (such as dispersants, protective colloids, emulsifiers, wetting agents and tackifiers), and if appropriate further auxiliaries which are customary for formulating crop protection products. The person skilled in the art is sufficiently familiar with the recipes for such formulations. Further auxiliaries include e.g. organic and inorganic thickeners, bactericides, antifreeze agents, antifoams, colorants and, for seed formulations, adhesives.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutyl-naphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

To prepare emulsions, pastes or oil dispersions, the active the components, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Powders, materials for spreading and dusts can be prepared by mixing or concomitant grinding of the active the herbicides A, B, optionally C and D with a solid carrier.

Granules, e.g. coated granules, impregnated granules and homogeneous granules, can be prepared by binding the active ingredients to solid carriers.

The formulations of the invention comprise a herbicidally effective amount of the composition of the present invention. The concentrations of the active the active ingredients in the formulations can be varied within wide ranges. In general, the formulations comprise from 1 to 98% by weight, preferably 10 to 60% by weight, of active ingredients (sum of pyroxasulfone, herbicide A and optionally further actives).

The active ingredients are employed in a purity of from 90% to 100%, preferably 95% to 100% (according to NMR spectrum).

The active compounds A, B and optionally C as well as the compositions according to the invention can, for example, be formulated as follows:

1. Products for Dilution with Water

A Water-Soluble Concentrates 10 parts by weight of active compound (or composition) are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound (or composition) are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound (or composition) are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound (or composition) are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound (or composition) are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound (or composition) are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound (or composition) are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound (or composition), 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound (or composition) are ground finely and mixed intimately with 95 parts by weight of finely divided kaolin. This gives a dusting powder with an active compound content of 5% by weight.

J Granules (GR, FG, GG, MG)

0.5 parts by weight of active compound (or composition) are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound (or composition) are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

It may furthermore be beneficial to apply the compositions of the invention alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

USE EXAMPLES

The effect of the herbicidal compositions according to the invention of herbicides A and B and, if appropriate, safener on the growth of undesirable plants compared to the herbicidally active compounds alone was demonstrated by the following greenhouse experiments:

For the pre-emergence treatment, directly after sowing the active compounds, which had been suspended or emulsified in water, were applied by means of finely distributed nozzles. The containers were irrigated gently to promote germination and growth and subsequently covered with transparent plastic hoods until plant had rooted. This cover caused uniform germination of the tests plants, unless this was adversely affected by active compounds.

For the post-emergence treatment, the test plants were first grown to a height of 3 to 20 cm, depending on the plant habit, and only then treated. Here, the herbicidal compositions were suspended or emulsified in water as distribution medium and sprayed using finely distributing nozzles.

The respective herbicides B and/or safener were formulated as 10% by weight strength suspension concentrate and introduced to the spray liquor with the amount of solvent system used for applying the active compound. Herbicides A, C and/or safener were used as commercially available formulations and introduced to the spray liquor with the amount of solvent system used for applying the active compound. In the examples, the solvent used was water.

Glyphosate was used as a commercially available SL-formulation containing 360 g/l of glyphosate as its isopropylammonium salt.

Pyroxasulfone was used as an emulsifiable concentrate having an active ingredient concentration of 5% by weight.

Imazamox was used as a commercially available SL-formulation containing 120 g/l of imazamox.

Imazapic was used as a commercially available SL-formulation containing 120 g/l of imazapic.

Pendimethalin was used as an emulsifiable concentrate having an active ingredient concentration of 396 g/l.

Dimethenamid-P was used as an emulsifiable concentrate having an active ingredient concentration of 720 g/l.

Atrazin was used as an aqueous suspension concentrate having an active ingredient concentration of 500 g/l.

Dicamba was used as a commercially available SL-formulation having an active ingredient concentration of 480 g/l.

Picolinafen was used as a commercially available WG-formulation having an active ingredient concentration of 75% by weight.

Saflufenacil was used as an emulsifiable concentrate having an active ingredient concentration of 120 g/l.

Flumioxazin was used as a WG-formulation having an active ingredient concentration of 51% by weight.

Compound B was used as an emulsifiable concentrate having an active ingredient concentration of 5% by weight.

Compound D was used as an emulsifiable concentrate having an active ingredient concentration of 5% by weight.

Isoxaflutole was used as a WG-formulation having an active ingredient concentration of 75% by weight.

compound B

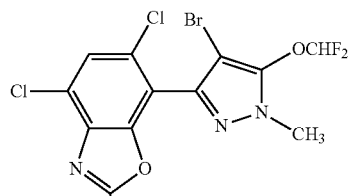

(B)

compound D

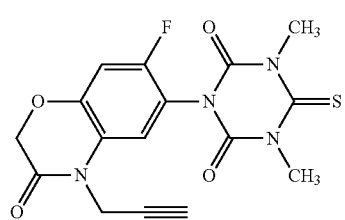

(D)

The test period extended over 21 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

The plants used in the greenhouse experiments belonged to the following species:

| Scientific Name | Code | Common Name |
|---|---|---|
| Abutilon theophrasti | ABUTH | velvetleaf |
| Agropyron repens | AGRRE | quackgrass |

-continued

| Scientific Name | Code | Common Name |
|---|---|---|
| Alopecurus myosuroides | ALOMY | blackgrass |
| Amaranthus retroflexus | AMARE | pig weed |
| Ambrosia artemisifolia | AMBEL | common ragweed |
| Apera spica-venti | APESV | windgrass |
| Avena fatua | AVEFA | wild oat |
| Brachiaria plantaginea | BRAPL | alexandergrass |
| Bromus inermis | BROIN | awnless brome |
| Bromus sterilis | BROST | sterile brome |
| Brassica napus spp. napus | BRSNW | winter oilseed-rape |
| Capsella bursa-pastoris | CAPBP | sheperd's-purse |
| Cenchrus echinatus | CCHEC | sandbur |
| Chenopodium album | CHEAL | lambsquarter |
| Commelina benghalensis | COMBE | tropical spiderwort |
| Digitaria sanguinalis | DIGSA | large crabgrass |
| Echinochloa crus-galli | ECHCG | barnyardgrass |
| Eleusine indica | ELEIN | goosegrass |
| Galium aparine | GALAP | cleaver |
| Glycine max | GLXMA | soybean |
| Gossypium hirsutum | GOSHI | cotton |
| Helianthus annuus | HELAN | sunflower |
| Hordeum vulgare | HORVW | winter barley |
| Kochia scoparia | KCHSC | kochia |
| Lamium purpureum | LAMPU | red deadnettle |
| Lolium multiflorum | LOLMU | italian ryegrass |
| Matricaria inermis | MATIN | scentless mayweed |
| Mercurialis annua | MERAN | annual mercury |
| Orysa sativa | ORYSA | rice |
| Panicum dichotomiflorum | PANDI | fall panicum |
| Panicum milliaceum | PANMI | proso millet |
| Phalaris canariensis | PHACA | canarygrass |
| Ipomoea purpurea | PHBPU | tall morningglory |
| Poa annua | POAAN | annual bluegrass |
| Polygonum convolvulus | POLCO | wild buckwheat |
| Secale cereale | SECCW | winter rye |
| Setaria faberii | SETFA | giant foxtail |
| Setaria italica | SETIT | foxtail millet |
| Setaria lutescens | SETLU | yellow foxtail |
| Setaria viridis | SETVI | green foxtail |
| Sinapis arvensis | SINAR | wild mustard |
| Solanum nigrum | SOLNI | black nightshade |
| Sorghum halepense | SORHA | johnsongrass |
| Stellaria media | STEME | chickweed |
| Thlaspi arvense | THLAR | field pennycress |
| Triticum aestivum | TRZAS | spring wheat |
| Triticum aestivum | TRZAW | winter wheat |
| Veronica persica | VERPE | field speedwell |
| Viola arvensis | VIOAR | field pansy |
| Xanthium strumarium | XANST | cocklebur |
| Zea mays | ZEAMX | corn |

Colby's formula was applied to determine whether the composition showed synergistic action. The value E, which is to be expected if the activity of the individual compounds is just additive, was calculated using the method of S. R. Colby (1967) "Calculating synergistic and antagonistic responses of herbicide combinations", Weeds 15, p. 22 ff. For two component mixtures the value E was calculated by the following formula $$E = X + Y - (X \cdot Y/100)$$

For three component mixtures the value E was calculated by the following formula $$E = X + Y + Z - (XY + XZ + YZ)/100 + (X \cdot Y \cdot Z/10000)$$

where

X=effect in percent using herbicide A at an application rate a;

Y=effect in percent using herbicide B at an application rate b;

Z=effect in percent using herbicide C at an application rate c;
E=expected effect (in %) of A+B at application rates a+b.
or
E=expected effect (in %) of A+B+C at application rates a+b+c.

If the value observed in this manner is higher than the value E calculated according to Colby, a synergistic effect is present.

Tables 1 to 12 relate to the herbicidal activity of the individual actives and of their combinations in post-emergence application assessed 20 DAT.

TABLE 1

Application in Post-Emergence of Glyphosate, Pyroxasulfone and Imazamox

| | solo application | | | | | | combination glyphosate + pyroxasulfone + imazamox | | |
| --- | --- | --- | --- | --- | --- | --- | --- | --- | --- |
| | glyphosate (A) | | pyroxasulfone (B) | | imazamox (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 100 | 40 | 25 | 50 | 10 | 30 | 100 + 25 + 10 | 98 | 79 | Y |
| DIGSA | 100 | 85 | 25 | 50 | 10 | 20 | 100 + 25 + 10 | 100 | 94 | Y |
| LOLMU | 100 | 75 | 25 | 50 | 10 | 60 | 100 + 25 + 10 | 98 | 95 | Y |
| LOLMU | 50 | 40 | 12.5 | 50 | 5 | 40 | 50 + 12.5 + 5 | 85 | 82 | Y |
| ABUTH | 50 | 0 | 12.5 | 40 | 5 | 50 | 50 + 12.5 + 5 | 90 | 70 | Y |
| CHEAL | 100 | 50 | 25 | 20 | 10 | 30 | 100 + 25 + 10 | 95 | 72 | Y |
| CHEAL | 50 | 40 | 12.5 | 20 | 5 | 15 | 50 + 12.5 + 5 | 90 | 59 | Y |
| GALAP | 100 | 15 | 25 | 80 | 10 | 30 | 100 + 25 + 10 | 95 | 88 | Y |
| GALAP | 50 | 10 | 12.5 | 70 | 5 | 20 | 50 + 12.5 + 5 | 90 | 78 | Y |
| MATIN | 50 | 65 | 12.5 | 0 | 5 | 25 | 50 + 12.5 + 5 | 80 | 74 | Y |

TABLE 2

Application in Post-Emergence of Glyphosate, Pyroxasulfone and Imazapic

| | solo application | | | | | | combination glyphosate + pyroxasulfone + imazapic | | |
| --- | --- | --- | --- | --- | --- | --- | --- | --- | --- |
| | glyphosate (A) | | pyroxasulfone (B) | | imazapic (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 200 | 85 | 50 | 50 | 20 | 45 | 200 + 50 + 20 | 98 | 96 | Y |
| DIGSA | 50 | 70 | 12.5 | 40 | 5 | 50 | 50 + 12.5 + 5 | 95 | 91 | Y |
| LOLMU | 50 | 40 | 12.5 | 50 | 5 | 60 | 50 + 12.5 + 5 | 90 | 88 | Y |
| ABUTH | 50 | 0 | 12.5 | 40 | 5 | 60 | 50 + 12.5 + 5 | 85 | 76 | Y |
| CHEAL | 200 | 80 | 50 | 20 | 20 | 40 | 200 + 50 + 20 | 95 | 90 | Y |
| GALAP | 50 | 10 | 12.5 | 70 | 5 | 55 | 50 + 12.5 + 5 | 95 | 88 | Y |

TABLE 3

Application in Post-Emergence of Glyphosate, Pyroxasulfone and Pendimethalin

| | solo application | | | | | | combination glyphosate + pyroxasulfone + pendimethalin | | |
| --- | --- | --- | --- | --- | --- | --- | --- | --- | --- |
| | glyphosate (A) | | pyroxasulfone (B) | | pendimethalin (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 200 | 85 | 50 | 50 | 400 | 40 | 200 + 50 + 400 | 98 | 96 | Y |
| LOLMU | 100 | 75 | 25 | 50 | 200 | 30 | 100 + 25 + 200 | 98 | 91 | Y |
| SETVI | 50 | 70 | 12.5 | 70 | 100 | 30 | 50 + 12.5 + 100 | 95 | 94 | Y |
| AMARE | 50 | 90 | 12.5 | 75 | 100 | 75 | 50 + 12.5 + 100 | 100 | 99 | Y |
| MATIN | 400 | 95 | 100 | 15 | 800 | 0 | 400 + 100 + 800 | 100 | 96 | Y |
| MATIN | 50 | 65 | 12.5 | 0 | 100 | 0 | 50 + 12.5 + 100 | 80 | 65 | Y |

TABLE 4

Application in Post-Emergence of Glyphosate, Pyroxasulfone and Dimethenamid-P

| | solo application | | | | | | combination glyphosate + pyroxasulfone + dimethenamid-P | | |
|---|---|---|---|---|---|---|---|---|---|
| | glyphosate (A) | | pyroxasulfone (B) | | dimethenamid-P (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 200 | 85 | 50 | 50 | 540 | 30 | 200 + 50 + 540 | 100 | 95 | Y |
| ALOMY | 100 | 40 | 25 | 50 | 270 | 20 | 100 + 25 + 270 | 90 | 76 | Y |
| DIGSA | 100 | 85 | 25 | 50 | 270 | 50 | 100 + 25 + 270 | 100 | 96 | Y |
| DIGSA | 50 | 70 | 12.5 | 40 | 135 | 50 | 50 + 12.5 + 135 | 98 | 91 | Y |
| LOLMU | 50 | 40 | 12.5 | 50 | 135 | 60 | 50 + 12.5 + 135 | 95 | 88 | Y |
| ABUTH | 200 | 70 | 50 | 70 | 540 | 15 | 200 + 50 + 540 | 95 | 92 | Y |
| ABUTH | 50 | 0 | 12.5 | 40 | 135 | 15 | 50 + 12.5 + 135 | 70 | 49 | Y |
| CHEAL | 100 | 50 | 25 | 20 | 270 | 20 | 100 + 25 + 270 | 95 | 68 | Y |
| MATIN | 100 | 90 | 25 | 0 | 270 | 0 | 100 + 25 + 270 | 98 | 90 | Y |
| MATIN | 50 | 65 | 12.5 | 0 | 135 | 0 | 50 + 12.5 + 135 | 90 | 65 | Y |
| SINAR | 50 | 80 | 12.5 | 65 | 135 | 45 | 50 + 12.5 + 135 | 100 | 96 | Y |

TABLE 5

Application in Post-Emergence of Glyphosate, Pyroxasulfone and Atrazin

| | solo application | | | | | | combination glyphosate + pyroxasulfone + atrazin | | |
|---|---|---|---|---|---|---|---|---|---|
| | glyphosate (A) | | pyroxasulfone (B) | | atrazin (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 200 | 85 | 50 | 50 | 250 | 50 | 200 + 50 + 250 | 100 | 96 | Y |
| DIGSA | 50 | 70 | 12.5 | 40 | 62.5 | 0 | 50 + 12.5 + 62.5 | 85 | 82 | Y |
| CHEAL | 100 | 50 | 25 | 20 | 125 | 60 | 100 + 25 + 125 | 98 | 84 | Y |
| CHEAL | 50 | 40 | 12.5 | 20 | 62.5 | 20 | 50 + 12.5 + 62.5 | 85 | 62 | Y |

TABLE 6

Application in Post-Emergence of Glyphosate, Pyroxasulfone and Dicamba

| | solo application | | | | | | combination glyphosate + pyroxasulfone + dicamba | | |
|---|---|---|---|---|---|---|---|---|---|
| | glyphosate (A) | | pyroxasulfone (B) | | dicamba (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 50 | 20 | 12.5 | 30 | 25 | 10 | 50 + 12.5 + 25 | 55 | 50 | Y |
| LOLMU | 100 | 75 | 25 | 50 | 50 | 0 | 100 + 25 + 50 | 95 | 88 | Y |
| ABUTH | 100 | 60 | 25 | 40 | 50 | 50 | 100 + 25 + 50 | 95 | 88 | Y |
| CHEAL | 100 | 50 | 25 | 20 | 50 | 50 | 100 + 25 + 50 | 90 | 80 | Y |
| MATIN | 50 | 65 | 12.5 | 0 | 25 | 45 | 50 + 12.5 + 25 | 95 | 81 | Y |

TABLE 7

Application in Post-Emergence of Glyphosate, Pyroxasulfone and Picolinafen

| | solo application | | | | | | combination glyphosate + pyroxasulfone + picolinafen | | |
|---|---|---|---|---|---|---|---|---|---|
| | glyphosate (A) | | pyroxasulfone (B) | | picolinafen (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 200 | 85 | 50 | 50 | 25 | 0 | 200 + 50 + 25 | 98 | 93 | Y |
| ALOMY | 50 | 20 | 12.5 | 30 | 6.25 | 0 | 50 + 12.5 + 6.25 | 55 | 44 | Y |
| DIGSA | 100 | 85 | 25 | 50 | 12.5 | 45 | 100 + 25 + 12.5 | 100 | 96 | Y |
| DIGSA | 50 | 70 | 12.5 | 40 | 6.25 | 30 | 50 + 12.5 + 6.25 | 95 | 87 | Y |
| LOLMU | 100 | 75 | 25 | 50 | 12.5 | 10 | 100 + 25 + 12.5 | 99 | 89 | Y |
| ABUTH | 200 | 70 | 50 | 70 | 25 | 60 | 200 + 50 + 25 | 98 | 96 | Y |
| ABUTH | 50 | 0 | 12.5 | 40 | 6.25 | 30 | 50 + 12.5 + 6.25 | 70 | 58 | Y |
| CHEAL | 100 | 50 | 25 | 20 | 12.5 | 30 | 100 + 25 + 12.5 | 90 | 72 | Y |

TABLE 7-continued

Application in Post-Emergence of Glyphosate, Pyroxasulfone and Picolinafen

| weed | solo application | | | | | | combination glyphosate + pyroxasulfone + picolinafen | | | |
|---|---|---|---|---|---|---|---|---|---|---|
| | glyphosate (A) | | pyroxasulfone (B) | | picolinafen (C) | | | Observed | expected | Synergism |
| | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| GALAP | 50 | 10 | 12.5 | 70 | 6.25 | 30 | 50 + 12.5 + 6.25 | 90 | 81 | Y |
| MATIN | 400 | 95 | 100 | 15 | 50 | 60 | 400 + 100 + 50 | 100 | 98 | Y |
| POLCO | 400 | 90 | 100 | 65 | 50 | 80 | 400 + 100 + 50 | 100 | 99 | Y |

TABLE 8

Application in Post-Emergence of Glyphosate, Pyroxasulfone and flumioxazin

| weed | solo application | | | | | | combination glyphosate + pyroxasulfone + flumioxazin | | | |
|---|---|---|---|---|---|---|---|---|---|---|
| | glyphosate (A) | | pyroxasulfone (B) | | flumioxazin (C) | | | Observed | expected | Synergism |
| | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 100 | 30 | 25 | 70 | 12.5 | 20 | 100 + 25 + 12.5 | 95 | 83 | Y |
| ALOMY | 50 | 15 | 12.5 | 40 | 6.25 | 20 | 50 + 12.5 + 6.25 | 85 | 59 | Y |
| AVEFA | 100 | 45 | 25 | 75 | 6.25 | 35 | 100 + 25 + 6.25 | 98 | 91 | Y |
| DIGSA | 50 | 70 | 12.5 | 50 | 6.25 | 15 | 50 + 12.5 + 6.25 | 95 | 87 | Y |
| CHEAL | 100 | 85 | 25 | 45 | 12.5 | 30 | 100 + 25 + 12.5 | 100 | 94 | Y |
| CHEAL | 50 | 30 | 12.5 | 35 | 6.25 | 0 | 50 + 12.5 + 6.25 | 98 | 55 | Y |
| GALAP | 100 | 45 | 25 | 85 | 12.5 | 30 | 100 + 25 + 12.5 | 100 | 94 | Y |
| GALAP | 50 | 40 | 12.5 | 40 | 6.25 | 30 | 50 + 12.5 + 6.25 | 98 | 75 | Y |
| MATIN | 50 | 90 | 12.5 | 0 | 6.25 | 65 | 50 + 12.5 + 6.25 | 100 | 97 | Y |

TABLE 9

Application in Post-Emergence of Glyphosate, Pyroxasulfone and Saflufenacil

| weed | solo application | | | | | | combination glyphosate + pyroxasulfone + saflufenacil | | | |
|---|---|---|---|---|---|---|---|---|---|---|
| | glyphosate (A) | | pyroxasulfone (B) | | saflufenacil (C) | | | Observed | expected | Synergism |
| | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 100 | 30 | 25 | 70 | 3.13 | 0 | 100 + 25 + 3.125 | 90 | 79 | Y |
| ALOMY | 50 | 15 | 12.5 | 40 | 1.56 | 0 | 50 + 12.5 + 1.56 | 70 | 49 | Y |
| DIGSA | 50 | 70 | 12.5 | 50 | 1.56 | 0 | 50 + 12.5 + 1.56 | 90 | 85 | Y |
| ECHCG | 50 | 30 | 12.5 | 75 | 1.56 | 0 | 50 + 12.5 + 1.56 | 85 | 83 | Y |
| ABUTH | 50 | 0 | 12.5 | 60 | 1.56 | 45 | 50 + 12.5 + 1.56 | 95 | 78 | Y |
| CHEAL | 50 | 30 | 12.5 | 35 | 1.56 | 40 | 50 + 12.5 + 1.56 | 90 | 73 | Y |
| GALAP | 100 | 45 | 25 | 85 | 3.13 | 30 | 100 + 25 + 3.125 | 98 | 94 | Y |
| MATIN | 100 | 95 | 25 | 0 | 3.13 | 55 | 100 + 25 + 3.125 | 100 | 98 | Y |
| MATIN | 50 | 90 | 12.5 | 0 | 1.56 | 20 | 50 + 12.5 + 1.56 | 100 | 92 | Y |
| POLCO | 100 | 50 | 25 | 50 | 3.13 | 55 | 100 + 25 + 3.125 | 98 | 89 | Y |
| POLCO | 50 | 30 | 12.5 | 35 | 1.56 | 45 | 50 + 12.5 + 1.56 | 98 | 75 | Y |

TABLE 10

Application in Post-Emergence of Glyphosate, Pyroxasulfone and Compound B

| weed | solo application | | | | | | combination glyphosate + pyroxasulfone + Compound B | | | |
|---|---|---|---|---|---|---|---|---|---|---|
| | glyphosate (A) | | pyroxasulfone (B) | | compound B (C) | | | Observed | expected | Synergism |
| | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 100 | 30 | 25 | 70 | 12.5 | 35 | 100 + 25 + 12.5 | 95 | 86 | Y |
| ALOMY | 50 | 15 | 12.5 | 40 | 6.25 | 20 | 50 + 12.5 + 6.25 | 85 | 59 | Y |
| DIGSA | 50 | 70 | 12.5 | 50 | 6.25 | 50 | 50 + 12.5 + 6.25 | 95 | 93 | Y |
| ABUTH | 100 | 0 | 25 | 65 | 6.25 | 98 | 100 + 25 + 6.25 | 100 | 99 | Y |

TABLE 10-continued

Application in Post-Emergence of Glyphosate, Pyroxasulfone and Compound B

| | solo application | | | | | | combination glyphosate + pyroxasulfone + Compound B | | |
|---|---|---|---|---|---|---|---|---|---|
| | glyphosate (A) | | pyroxasulfone (B) | | compound B (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| CHEAL | 50 | 30 | 12.5 | 35 | 6.25 | 85 | 50 + 12.5 + 6.25 | 100 | 93 | Y |
| POLCO | 50 | 30 | 12.5 | 35 | 6.25 | 90 | 50 + 12.5 + 6.25 | 100 | 95 | Y |

TABLE 11

Application in Post-Emergence of Glyphosate, Pyroxasulfone and Compound D

| | solo application | | | | | | combination glyphosate + pyroxasulfone + compound D | | |
|---|---|---|---|---|---|---|---|---|---|
| | glyphosate (A) | | pyroxasulfone (B) | | compound D (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 100 | 30 | 25 | 70 | 6.25 | 40 | 100 + 25 + 6.25 | 98 | 87 | Y |
| ALOMY | 50 | 15 | 12.5 | 40 | 3.13 | 30 | 50 + 12.5 + 3.125 | 75 | 64 | Y |
| AVEFA | 100 | 45 | 25 | 75 | 6.25 | 75 | 100 + 25 + 6.25 | 98 | 97 | Y |
| DIGSA | 50 | 70 | 12.5 | 50 | 3.13 | 35 | 50 + 12.5 + 3.125 | 95 | 90 | Y |
| LOLMU | 50 | 45 | 12.5 | 55 | 3.13 | 40 | 50 + 12.5 + 3.125 | 95 | 85 | Y |
| CHEAL | 50 | 30 | 12.5 | 35 | 3.13 | 45 | 50 + 12.5 + 3.125 | 90 | 75 | Y |
| GALAP | 100 | 45 | 25 | 85 | 6.25 | 30 | 100 + 25 + 6.25 | 98 | 94 | Y |
| GALAP | 50 | 40 | 12.5 | 40 | 3.13 | 30 | 50 + 12.5 + 3.125 | 98 | 75 | Y |
| POLCO | 50 | 30 | 12.5 | 35 | 3.13 | 95 | 50 + 12.5 + 3.125 | 100 | 98 | Y |

TABLE 12

Application in Post-Emergence of Glyphosate, Pyroxasulfone and Isoxaflutole

| | solo application | | | | | | combination glyphosate + pyroxasulfone + isoxaflutole | | |
|---|---|---|---|---|---|---|---|---|---|
| | glyphosate (A) | | pyroxasulfone (B) | | isoxaflutole (C) | | | Observed | expected | Synergism |
| weed | g ai/ha | % activity 20 DAT | g ai/ha | % activity 20 DAT | g ai/ha | % activity 20 DAT | g ai/ha | % activity 20 DAT | % activity 20 DAT | Y/N 20 DAT |
| ALOMY | 50 | 15 | 12.5 | 40 | 6.25 | 0 | 50 + 12.5 + 6.25 | 80 | 49 | Y |
| DIGSA | 50 | 70 | 12.5 | 50 | 6.25 | 15 | 50 + 12.5 + 6.25 | 90 | 87 | Y |
| ABUTH | 50 | 0 | 12.5 | 60 | 6.25 | 55 | 50 + 12.5 + 6.25 | 90 | 82 | Y |
| CHEAL | 50 | 30 | 12.5 | 35 | 6.25 | 75 | 50 + 12.5 + 6.25 | 95 | 89 | Y |
| POLCO | 200 | 50 | 50 | 50 | 25 | 45 | 200 + 50 + 25 | 98 | 86 | Y |

The invention claimed is:

1. A herbicidal composition comprising
a) at least one herbicide A selected from the group consisting of glyphosate, glufosinate and their salts, and
b) a herbicide B which is 3-[5-(difluoromethoxy)-1-methyl-3-(trifluoromethyl)pyrazol-4-ylmethylsulfonyl]-4,5-dihydro-5,5-dimethyl-1,2-oxazole, and
c) at least one further herbicide C selected from the group consisting of picolinafen, dimethenamid-P, Compound B, and Compound D.

2. The herbicidal composition as claimed in claim 1, wherein herbicide C is picolinafen, its agriculturally acceptable salts and mixtures thereof.

3. The herbicidal composition as claimed in claim 1, which comprises as a further herbicide at least one photosystem II inhibitor C6 selected from the group consisting of terbuthylazin, ametryn, hexazinone, metribuzin, diuron, isoproturon, tebuthiuron and their agriculturally acceptable salts and mixtures thereof.

4. The herbicidal composition as claimed in claim 1, wherein the weight ratio of herbicide A to herbicide B is from 2000:1 to 1:10.

* * * * *